United States Patent
Ciulli et al.

(10) Patent No.: US 11,234,988 B2
(45) Date of Patent: Feb. 1, 2022

(54) FLUOROHYDROXYPROLINE DERIVATIVES USEFUL IN THE PREPARATION OF PROTEOLYSIS TARGETED CHIMERAS

(71) Applicant: UNIVERSITY OF DUNDEE, Dundee (GB)

(72) Inventors: Alessio Ciulli, Dundee (GB); Andrea Testa, Dundee (GB)

(73) Assignee: University of Dundee, Dundee (GB)

( * ) Notice: Subject to any disclaimer, the term of this patent is extended or adjusted under 35 U.S.C. 154(b) by 0 days.

(21) Appl. No.: 16/333,454

(22) PCT Filed: Sep. 14, 2017

(86) PCT No.: PCT/GB2017/052726
§ 371 (c)(1),
(2) Date: Mar. 14, 2019

(87) PCT Pub. No.: WO2018/051107
PCT Pub. Date: Mar. 22, 2018

(65) Prior Publication Data
US 2019/0255066 A1 Aug. 22, 2019

(30) Foreign Application Priority Data
Sep. 14, 2016 (GB) ..................................... 1615617

(51) Int. Cl.
| | | |
|---|---|---|
| *C07D 207/00* | (2006.01) | |
| *A61K 31/551* | (2006.01) | |
| *A61K 47/54* | (2017.01) | |
| *A61K 47/55* | (2017.01) | |
| *A61K 31/4709* | (2006.01) | |
| *A61K 45/06* | (2006.01) | |
| *C07D 207/46* | (2006.01) | |
| *C07D 417/12* | (2006.01) | |
| *C07D 417/14* | (2006.01) | |
| *C07D 495/14* | (2006.01) | |
| *C07D 207/16* | (2006.01) | |
| *C07K 5/062* | (2006.01) | |
| *C07K 5/087* | (2006.01) | |
| *A61K 31/427* | (2006.01) | |

(52) U.S. Cl.
CPC .......... *A61K 31/551* (2013.01); *A61K 31/427* (2013.01); *A61K 31/4709* (2013.01); *A61K 45/06* (2013.01); *A61K 47/545* (2017.08); *A61K 47/55* (2017.08); *A61K 47/555* (2017.08); *C07D 207/16* (2013.01); *C07D 207/46* (2013.01); *C07D 417/12* (2013.01); *C07D 417/14* (2013.01); *C07D 495/14* (2013.01); *C07K 5/06034* (2013.01); *C07K 5/0812* (2013.01); *C07B 2200/07* (2013.01)

(58) Field of Classification Search
CPC ........................... A61K 31/395; C07D 207/00
See application file for complete search history.

(56) References Cited

FOREIGN PATENT DOCUMENTS

| EP | 2985285 A1 | 2/2016 | |
|---|---|---|---|
| WO | WO-2009014730 A1 * | 1/2009 | .............. A61P 31/14 |
| WO | WO-2012093101 A1 * | 7/2012 | ................ A61P 7/00 |
| WO | WO-2012093101 A1 | 7/2012 | |
| WO | WO-2013106643 A2 | 7/2013 | |
| WO | WO-2013106646 A2 | 7/2013 | |
| WO | WO-2014002057 | 1/2014 | |
| WO | WO-2014002057 A1 * | 1/2014 | ................ A61P 1/04 |
| WO | WO-2015000867 A1 | 1/2015 | |
| WO | WO-2015000868 A1 | 1/2015 | |
| WO | WO 2015/160845 A2 | 10/2015 | |
| WO | WO-2016118666 A1 | 7/2016 | |
| WO | WO-2016146985 A1 | 9/2016 | |
| WO | WO-2016149668 A1 | 9/2016 | |

OTHER PUBLICATIONS

Hofman, Gert-Jan, et al. "Synthesis and Conformational Properties of 3,4-Difluoro-L-prolines." J. Org. Chem. (2019), vol. 84, pp. 3100-3120. (Year: 2019).*
American Chemical Society. Chemical Abstract Service. RN 1446438-72-7. First made available to the public/entered into STN on Jul. 29, 2013. (Year: 2013).*
Testa, Andrea, et al. "3-Fluoro-4-hydroxyprolines: Synthesis, Conformational Analysis, and Stereoselective Recognition by the VHL E3 Ubiquitin Ligase for Targeted Protein Degradation." Journal of American Chemical Society. (2018), vol. 140, pp. 9299-9313. (Year: 2018).*
A. Testa et al., "3-Flouro-4-hydroxyprolines: Synthesis, Conformational Analysis, and Stereoselective Recognition by the VHL E3 Ubiquitin Ligase for Targeted Protein Degradation", J. Am. Chem. Soc. 2018, 140, pp. 9299-9313.
A. Testa et al., "3-Flouro-4-hydroxyprolines: Synthesis, Conformational Analysis, and Stereoselective Recognition by the VHL E3 Ubiquitin Ligase for Targeted Protein Degradation", Supporting Information, 108 pgs.
Database Reistry[Online] Chemical Abstracts Service, Columbus, Ohio, US; Jul. 29, 2013, XP002775790, Database accession No. 1446438-72-7 the compound with registry No. 1446438-72-7.
Liu et al. "3-Fluoroazetidinecarboxylic Acid and trans, trans-3,4-Difluoroproline as Peptide Scaffolds: Inhibition of Pancreatic Cancer Cell Growth by a Fluoroazetidine Iminosugar" The Journal of Organic Chemistry, vol. 80, No. 9, May 17, 2015, p. 4244-4258, XP055421991,US.

(Continued)

*Primary Examiner* — John S Kenyon
(74) *Attorney, Agent, or Firm* — Moser Taboada

(57) ABSTRACT

There is provided novel small molecule E3 ubiquitin ligase protein binding ligand compounds, and to their utility in PROteolysis Targeted Chimeras (PROTACs), as well as processes for their preparation thereof, and use in medicine. There is particularly provided novel small molecule E3 ubiquitin ligase protein binding inhibitor compounds based on a fluorohydroxyproline scaffold, to their utility as ligands in synthesizing novel PROTACs, and to synthetic methods therefor.

19 Claims, 8 Drawing Sheets

(56) References Cited

OTHER PUBLICATIONS

Zengerle et al."Selective Small Molecule Induced Degradation of the BET Bromodomain Protein BRD4" ACS Chemical Biology, vol. 10, No. 8, Aug. 21, 2015, p. 1170-1777, XP055333869, US.
Raina et al. "PROTAC-induced BET protein degradation as a therapy for castration-resistant prostrate cancer" Proceedings National Academy of Sciences PNAS, vol. 113, No .26, Jun. 6, 2016, p. 7124-7129, XP055422055, US.
International Search Report dated Jan. 12, 2017 for PCT Application No. PCT/GB2017/052726.

* cited by examiner

| entry | compound | protein | $K_d$ [nM] | $\Delta H$ [kcal/mol] |
|---|---|---|---|---|
| 1 | MZ1 | BRD2 BD1 | 307±27.9 | -10.0±0.1 |
| 2 | MZ1 | BRD2 BD2 | 228±17.7 | -6.08±0.04 |
| 3 | MZ1 | BRD3 BD1 | 119±4.81 | -10.0±0.06 |
| 4 | MZ1 | BRD3 BD2 | 115±10.9 | -8.32±0.05 |
| 5 | MZ1 | BRD4 BD1 | 382±13.5 | -8.59±0.03 |
| 6 | MZ1 | BRD4 BD2 | 120±7.16 | -6.86±0.03 |
| 7 | JQ1 | BRD4 BD1 | 49.0±2.40 | -8.42±0.02' |
| 8 | JQ1 | BRD4 BD2 | 90.1±4.60 | -3.22±0.01' |
| 9 | MZ1 | VBC | 149±13.1 | -6.87±0.05 |
| 10 | MZ3 | VBC | 311±51.2 | -4.90±0.11 |
| 11 | VHL-1 | VBC | 118±6.42 | -5.53±0.01" |
| 12 | cisMZ1 | VBC | no binding | | cisMZ1

MZ1

FLUOROHYDROXYPROLINE DERIVATIVES USEFUL IN THE PREPARATION OF PROTEOLYSIS TARGETED CHIMERAS

FIELD OF THE INVENTION

This invention relates to novel small molecule E3 ubiquitin ligase protein binding ligand compounds and inhibitors, and to their utility in PROteolysis Targeted Chimeras (PROTACs), as well as processes for their preparation thereof, and use in medicine. This invention particularly relates to novel small molecule E3 ubiquitin ligase protein binding ligand compounds based on a fluorohydroxyproline scaffold, to their utility in synthesizing novel PROTACs, and to synthetic methods therefor.

BACKGROUND OF THE INVENTION

Hydroxyproline (Hyp) is a naturally occurring proline derivative, principally found in collagen in two isomeric forms, 4-hydroxyproline and 3-hydroxyproline (70:1 ratio). It is synthesized in-vivo as a posttranslational modification of peptide bound proline, catalyzed by prolyl-hydroxylase enzymes. Hyp is an interesting fragment for drug development due to its exceptional conformational rigidity and is found in a number of natural compounds and clinically used drugs, for example: Pasireotide, Paritaprevir and Caspofungin.

More recently, as reported by Galdeano et al., J. Med. Chem. 2014, 57, 8657-8663, small molecules incorporating Hyp have been developed which target the von Hippel-Lindau protein (VHL) Cullin RING ligase. The primary substrate of pVHL is the hypoxia inducible factor 1α (HIF-1α), a transcription factor that regulates over 2% of human genes, particularly those related to oxygen sensing and the hypoxic response. Under normal oxygen levels, HIF-1α is constitutively expressed and targeted for proteasomal degradation upon hydroxylation by prolyl hydroxylases domain (PHD) enzymes at Pro402 and Pro564 within its N-terminal oxygen-degradation domain (NODD) and C-terminal oxygen-degradation domain (CODD), respectively, leading to specific recruitment by pVHL and subsequent pVHL-mediated polyubiquitination. Small-molecule inhibition of this pathway would be expected to mimic the physiological response to low oxygen levels by increasing the expression of genes involved with the hypoxic response. To this end, small-molecule PHD inhibitors are already under examination in clinical trials for the treatment of chronic anemia associated with chronic kidney disease and cancer chemotherapy.

VHL mediated proteosomal degradation has also been exploited in the construction of so-called Proteolysis Targeted Chimeras (PROTACs). A PROTAC compound is a hetero-bi-functional compound containing two ligands connected by a linker unit. A first ligand binds to an E3 ubiquitin ligase protein (for example, VHL) and the other ligand binds to the target protein of interest, thereby bringing the ligase and the target into close proximity. Whilst not wishing to be bound to any particular theory it is proposed herein that this close proximity triggers the poly-ubiquitination and subsequent proteasome-dependent degradation of the target protein of interest.

For at least the above reasons, it is additionally proposed herein that there is an ongoing need in the art to expand the chemical space of hydroxyproline and to develop novel hydroxyproline derivatives suitable for use in drug development.

The Bromo- and Extra-terminal (BET) family of proteins, including the ubiquitously expressed BRD2, BRD3, BRD4 and the testis-specific BRDT, are known to recruit transcriptional regulatory complexes to acetylated chromatin and thereby control specific networks of genes involved in cellular proliferation and in cell cycle progression. Deregulation of BET protein activity, in particular BRD4, has been strongly linked to cancer and inflammatory diseases, making BET proteins attractive drug targets. As well as their potential roles in transcriptional regulation, epigenetics and cancer the Bromo- and Extra-terminal (BET) family of proteins BRD2, BRD3 and BRD4 are thought to play an important role in epigenetics and are the targets of the pan-BET selective bromodomain inhibitor JQ1.

RNAi screens have identified BRD4 as a therapeutic target in acute myeloid leukaemia and ovarian carcinoma. In addition siRNA knock-down of BRD4, but not of BRD2 or BRD3, has been shown to induce upregulation of apolipoprotein A1 (ApoA1), which is thought to protect from atherosclerosis progression and other inflammatory processes. This knock-down, or silencing, of BRD4 has identified BRD4 as a potential target in the search for treatments of chronic obstructive pulmonary disease (COPD).

In target validation, the use of small molecule chemical probes or inhibitors, acting at the posttranslational level, holds several advantages over genetic techniques such as dominant-negative mutants or knockouts and RNAi knockdowns. These advantages include the provision of spatial and temporal control in a reversible fashion. Crucial to the function of BET proteins are two highly homologous bromodomains, which are present in the amino-terminal regions of the BET proteins, and which direct recruitment to nucleosomes by binding to specific acetylated lysines ($K_{Ac}$) within histone tails. Small molecule BET inhibitors, including amongst others the triazolodiazepine-based JQ1, I-BET762 and the tetrahydroquinoline-based I-BET726 are known to bind to the $K_{Ac}$-binding pocket of these bromodomains and to disrupt interaction with histones, and thereby displace BET proteins and their associated transcriptional regulatory complexes from chromatin. These BET inhibitors are highly potent ($K_d$~100 nM), cell-penetrant and active in vitro and in vivo against a range of solid, haematological and other tumours, which has prompted BET inhibitor compounds entering Phase I clinical trials for cancer.

Therapeutically, the effects of the known BET inhibitors on multiple transcriptional pathways have raised concerns about the safety and tolerability of BET inhibitors in humans. Crucially none of the BET inhibitors described to date has selective effects on the BRD4 bromodomains over those of its paralogs BRD2 and BRD3. Thus there is a need for new BET inhibitors which have selective effects on BRD4 bromodomains over those of its paralogs BRD2 and BRD3. Thus it would be desirable to develop compounds which provide intra-BED selective impact, and in particular for new BET inhibitor compounds which are selective for BRD4 bromodomains over those of its paralogs BRD2 and BRD3.

To date, no BET inhibitors have shown intra-BET selectivity for individual BET family members. Not only has this prevented the development of BET-inhibitor-based therapies per se, it significantly limits their scope as chemical probes for validating the roles of individual BET targets in physiology and disease. In an attempt to address this issue, chemical genetic strategies have been recently developed to engineer orthogonal selective BET bromodomain-ligand pairs, such as that described in Baud, M. G. J. et al. "A bump-and-hole approach to engineer controlled selectivity of BET bromodomain chemical probes", Science 346, 638-41 (2014). Whilst the Baud approach has the advantage of enabling disruption at will of a single or more bromodomains, it requires a mutation to be introduced into the target protein, and as a result cannot be developed into a drug of itself.

This lack of intra-BET selectivity has limited the scope for the potential utility of current inhibitors as probes for target validation, particularly due to concerns about potential unwanted side effects or toxicity in a therapeutic setting. Thus it would be desirable to provide BET inhibitor compounds which are both selective for one or more bromodomains within the BET family of proteins and which are suitable for use as drugs i.e. pharmaceutically, bio-pharmaceutically, veterinarily active compounds.

A general limitation associated with conventional occupancy-driven target inhibition approaches is that they often demands systemic target engagement, requiring sustained high concentration of a potent small molecule inhibitor over a prolonged time. This in turn enhances off-target effects and can lead to unwanted side effects or toxicity in a therapeutic setting.

The Applicant has developed an alternative small molecule approach which delivers against the long-felt want for a selective BET inhibitor, and which also overcomes the prior-issues associated with systemic target engagement. In particular, the Applicant has now developed new compounds that can remove BET proteins entirely from cells as opposed to just inhibiting them. Not only does this provide novel BET inhibitor compounds for use in the development of new medicines, it also provides new tools for studying BET bromodomain proteins and validating them as drug targets.

The Applicant has also developed a process for the preparation of 3-fluoro-hydroxyproline intermediate compounds for use in the preparation of compounds of formula A.

SUMMARY OF THE INVENTION

The Applicant has now developed novel fluorinated PROteolysis Targeted Chimeric compounds (PROTACs) having the structure A-L-B that can tether a protein binding ligand, for example a bromodomain inhibitor, such as for example JQ1, via a moiety which binds to a protein within the bromo- and Extra-terminal (BET) family of proteins (B) to a small molecule E3 ubiquitin ligase protein binding ligand compound (A) of formula I, such as for example a VHL-E3 ubiquitin ligase binding ligand compound of formula I, via suitable linker (L). Some PROTACs of the present invention are capable of binding to a protein within the bromo- and Extra-terminal (BET) family of proteins independently selected from: BRD2, BRD3 and BRD4, and selectively inducing degradation of the BRD4 protein within the bromo- and Extra-terminal (BET) family of proteins.

According to a first aspect the present invention provides compounds having the structure A-L-B wherein A is an E3 ubiquitin ligase protein binding ligand compound of formula I:

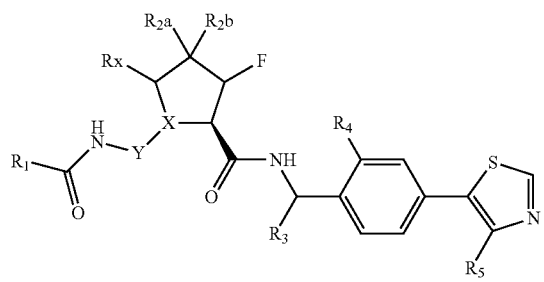

wherein L is a group which is directly bonded to the compound of formula I and wherein L is $-(CH_2)_n L^1 (CH_2O)_p-$, wherein $L^1$ is a covalent bond, a 5 or 6 membered heterocyclic or heteroaromatic ring containing 1, 2 or 3 nitrogen atoms, phenyl, $-(C_2-C_4)$alkyne, $-SO_2-$, or $-NH-$, wherein n and p are independently 0 to 10, wherein X is C or N, wherein $R^1$ is a covalent C-linked bond to L, $-(CH_2)_m Q_v$ group with a covalent C-linked bond to L, a $(C_1-C_4)$ alkyl group, or a C-linked $(C_3-C_4)$ heterocyclic group, wherein m is 0, 1 or 2 and v is 0 or 1, wherein Q is a $(C_3-C_4)$cyclic or $(C_3-C_4)$—C-linked nitrogen containing heterocyclic group, wherein one of the ring atoms in the Q group is optionally substituted with a —NHC (O) group or a —C(O) group, wherein said $R^1$ groups may be optionally substituted by one or more groups independently selected from F, CN, C(O) or $C(O)(C_1-C_3)$alkyl, wherein $R^{2a}$ is OH, $-CHF_2$, $-CF_3$, $NH_2$ or F, wherein $R^{2b}$ is H, $^2$H, $^3$H, a $-(C_1-C_3)$ alkyl group, an aryl group, a heteroaryl group, $-CF_3$, $-CF_2H$, a $-CF_2-(C_1-C_2)$ alkyl group, or F, wherein $R^x$ is H, OH, $-CHF_2$, $-CF_3$, $NH_2$ or F, wherein $R^3$ and $R^4$ are independently selected from H, a covalent C-linked, a covalent O-linked, or a covalent C(O)-linked bond to L, $R^5$ is a $-(C_1-C_3)$ alkyl group or a covalent C-linked bond to L, wherein Y is

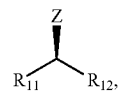

wherein Z is $CR^6R^7R^8$ or $SR^6R^7R^8R^9R^{10}$, wherein $R^{11}$ is a covalent C-linked bond or a

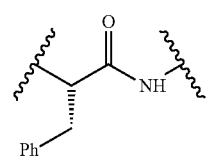

group, wherein $R^{12}$ is $-C(O)-$, $-C(S)-$ or a $-C(=)-R^{13}$ group, wherein when Z is $CR^6R^7R^8$, $R^6$ and $R^7$ are each independently $-(C_1-C_3)$ alkyl groups, or wherein $R^6$ and R$^7$ together with the C-atom to which they are attached form a —(C$_3$-C$_4$) cycloalkyl group,
wherein when Z is CR$^6$R$^7$R$^8$, R$^8$ is a —(C$_1$-C$_3$) alkyl group, a —(CH$_2$)$_q$R$^{8*}$ group wherein q is 0, 1 or 2, a —C(O)—R$^{8*}$ group, or a —N(H)—R$^{8*}$ group,
and wherein R$^{8*}$ is a covalent C-, S-, or N-linked bond to L, or H,
or wherein when Z is SR$^6$R$^7$R$^8$R$^9$R$^{10}$, R$^6$, R$^7$, R$^8$, R$^9$ and R$^{10}$ are each independently selected from: F; or —(C$_1$-C$_3$) alkyl groups,
wherein R$^{13}$ is H, F or a-(C$_1$-C$_3$) alkyl group,
wherein the —(C$_1$-C$_3$) alkyl groups, or —(C$_3$-C$_4$) cycloalkyl groups where present in a Y group are optionally substituted by one or more substituents independently selected from: methyl; OH; or F,
and wherein B is an additional optional ligand which binds to a target protein or polypeptide which is to be degraded by ubiquitin ligase and is linked to A though a —C-linkage to the L group,
or a pharmaceutically acceptable, salt, enantiomer, stereoisomer, hydrate, solvate, or polymorph thereof.

The present invention provides compounds having the structure A-L-B wherein A is an E3 ubiquitin ligase protein binding ligand compound of formula I wherein L is —(CH$_2$)$_n$ L$^1$(CH$_2$O)$_p$—, wherein L$^1$ is a covalent bond, a 5 or 6 membered heterocyclic or heteroaromatic ring containing 1, 2 or 3 nitrogen atoms, phenyl, —(C$_2$-C$_4$)alkyne, —SO$_2$—, or —NH—, wherein X is C or N, wherein n and p are independently 0 to 10, wherein R$^1$ is a covalent C-linked bond to L, a —(CH$_2$)$_m$Q$_v$ group with a covalent C-linked bond to L, a (C$_1$-C$_4$) alkyl group, or a C-linked (C$_3$-C$_4$) heterocyclic group, wherein m is 0, 1 or 2 and v is 0 or 1, and wherein when m is 0, v is 1, wherein Q is a (C$_3$-C$_4$)cyclic or (C$_3$-C$_4$)—C-linked nitrogen containing heterocyclic group, wherein one of the ring atoms in the Q group is optionally substituted with a —NHC(O) group or a —C(O) group, wherein said R$^1$ groups may be optionally substituted by one or more groups independently selected from F, CN, C(O) or C(O)(C$_1$-C$_3$)alkyl, wherein R$^{2a}$ is OH, —CHF$_2$, —CF$_3$, NH$_2$ or F, wherein R$^{2b}$ is H, $^2$H, $^3$H, a —(C$_1$-C$_3$) alkyl group, an aryl group, a heteroaryl group, —CF$_3$, —CF$_2$H, a —CF$_2$—(C$_1$-C$_2$) alkyl group, wherein R$^3$ and R$^4$ are independently selected from H, a covalent C-linked, a covalent O-linked, or a covalent C(O)-linked bond to L, wherein R$^5$ is a —(C$_1$-C$_3$) alkyl group or a covalent C-linked bond to L, wherein Y is

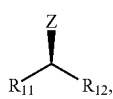

wherein Z is CR$^6$R$^7$R$^8$ or SR$^6$R$^7$R$^8$R$^9$R$^{10}$, wherein R$^{11}$ is a covalent C-linked bond or a

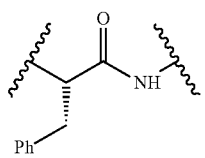

group, wherein R$^{12}$ is a —C(O)— group, wherein when Z is CR$^6$R$^7$R$^8$, R$^6$ and R$^7$ are each independently —(C$_1$-C$_3$) alkyl groups or wherein R$^6$ and R$^7$ together with the C-atom to which they are attached form a —(C$_3$-C$_4$) cycloalkyl group, and wherein when Z is CR$^6$R$^7$R$^8$, R$^8$ is a —(C$_1$-C$_3$) alkyl group, a —(CH$_2$)$_q$R$^{8*}$ group wherein q is 0, 1 or 2, a —C(O)—R$^{8*}$ group, or a —N(H)—R$^{8*}$ group, wherein R$^{8*}$ is a covalent C-, or S-linked bond to L, or H, or wherein when Z is SR$^6$R$^7$R$^8$R$^9$R$^{10}$, R$^6$, R$^7$, R$^8$, R$^9$ and R$^{10}$ are each independently selected from F or —(C$_1$-C$_3$) alkyl groups, wherein R$^{13}$ is H, F or a-(C$_1$-C$_3$) alkyl group, and wherein the —(C$_1$-C$_3$) alkyl groups, or —(C$_3$-C$_4$) cycloalkyl groups are optionally substituted by one or more substituents independently selected from: methyl; OH; or F,
and wherein B is a ligand which binds to a target protein or polypeptide which is to be degraded by ubiquitin ligase and is linked to A though a —C-linkage to the L group,
or a pharmaceutically acceptable, salt, enantiomer, stereoisomer, hydrate, solvate, or polymorph thereof.

The present invention provides compounds having the structure A-L-B wherein A is an E3 ubiquitin ligase protein binding ligand compound of formula I, and L is a linker as detailed in either of the aspects detailed above and wherein B is present, and wherein B is a chemical moiety which binds to a protein within the bromo- and Extra-terminal (BET) family of proteins.

The present invention provides compounds having the structure A-L-B wherein A is an E3 ubiquitin ligase protein binding ligand compound of formula I, and L is a linker in accordance with any of the aspects as detailed above, wherein Y is

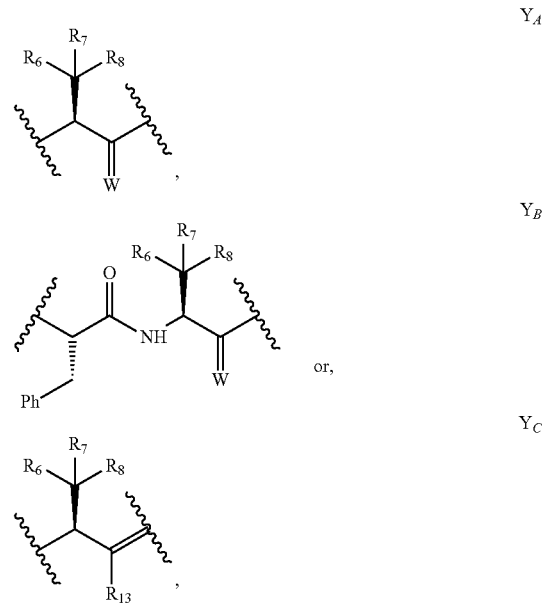

wherein R$^6$, R$^7$, R$^8$ and R$^{13}$ are as defined hereinbefore and wherein W may be O or S.

In preferred aspects the present invention provides compounds having the structure A-L-B wherein A is an E3 ubiquitin ligase protein binding ligand compound of formula I, and L is a linker in accordance with any of the aspects as detailed above, wherein Y is Y$_A$ or Y$_B$ and wherein W is O, more preferably Y is Y$_A$ and W is O.

The present invention provides compounds having the structure A-L-B wherein A is an E3 ubiquitin ligase protein binding ligand compound of formula I, and L is a linker in accordance with any of the aspects as detailed above, wherein A has the general formula IA

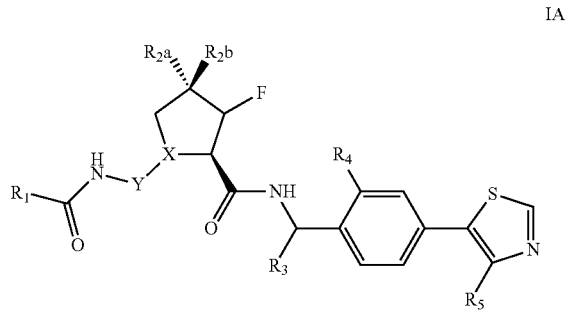

IA wherein $R^1$ to $R^5$, X, Y, L and B are in accordance with any of the aspects defined herein.

The present invention provides compounds having the structure A-L-B wherein A is an E3 ubiquitin ligase protein binding ligand compound of formula I or IA, or any other general formula herein, and L is a linker in accordance with any of the aspects as detailed above, wherein B is a chemical moiety which selectively induces degradation of the BRD4 protein within the bromo- and Extra-terminal (BET) family of proteins, and optionally wherein B is independently selected from: JQ1; I-BET726; I-BET 762.

The present invention provides PROTAC compounds of formula I which bind to a protein within the bromo- and Extra-terminal (BET) family of proteins, preferably PROTAC compounds of formula 1 which bind to a protein within the bromo- and Extra-terminal (BET) family of proteins independently selected from: BRD2, BRD3 and BRD4, and particularly PROTAC compounds of formula I which selectively induces degradation of the BRD4 protein within the bromo- and Extra-terminal (BET) family of proteins.

The present invention also provides PROTAC compounds of formula I for use in medicine, particularly for use in conditions or diseases where binding to a protein within the bromo- and Extra-terminal (BET) family of proteins independently selected from: BRD2, BRD3 and BRD4 is implicated, and especially for use in the treatment of one or more conditions or diseases independently selected from: cancer; benign proliferative disorders; infection or non-infectious inflammatory events; autoimmune diseases; inflammatory diseases; systemic inflammatory response syndromes; viral infections and diseases; opthalmological conditions.

In another aspect, the present invention provides a pharmaceutical composition comprising one or more PROTAC compounds of formula I and a pharmaceutically acceptable carrier, vehicle or diluent therefor.

In a further aspect, there is provided a process for the preparation of 3-fluoro-hydroxyproline intermediate compounds suitable for use in the preparation of compounds of formula A.

The above aspects of the present invention, as well as further aspects are detailed hereinafter.

DESCRIPTION OF THE INVENTION

Described herein is the novel small molecule approach, as developed by the Applicant which uses PROTAC compounds of structure A-L-B, which has been demonstrated to achieve rapid, effective and prolonged intracellular degradation of BET bromodomain proteins. The PROTAC-induced protein degradation potential of the present compounds has been confirmed for binding to VHL, has been demonstrated to be reversed upon blocking proteasome activity, and has been demonstrated to not interfere with the endogenous, physiological levels of VHL and of its natural substrate HIF-1α. Experiments using PROTAC compounds of structure A-L-B, have confirmed that all investigated compounds showed preferential degradation of BRD4 over BRD2 and BRD3 at low concentrations.

As discussed hereinafter the experimental results for PROTACs suggest a different pharmacological response resulting from selectively depleting BRD4 with an A-L-B compound (MZ1) compared to inhibiting the whole BET protein subfamily with JQ1. Without wishing to be bound to any particular theory, as additional experiments have confirmed that no preference for binding the bromodomains of BRD4 over the highly homologous bromodomains of BRD2 and BRD3 was observed by ITC within the context of the purified proteins, it is proposed herein that the observed selectivity could arise from preferential and more efficient poly-ubiquitination of lysine residues on the surface of BRD4 compared to those of BRD2 and BRD3. Alternatively or in addition, we also propose that preferential direct interaction between VHL and BRD4 compared to BRD2/3 may occur as a result of binding to PROTAC compounds of the present invention, triggering a more productive formation of a VHL:PROTAC:BRD4 ternary complex.

As indicated hereinbefore the Applicant has developed PROTAC compounds having the structure A-L-B wherein A is an E3 ubiquitin ligase protein binding ligand compound of formula I:

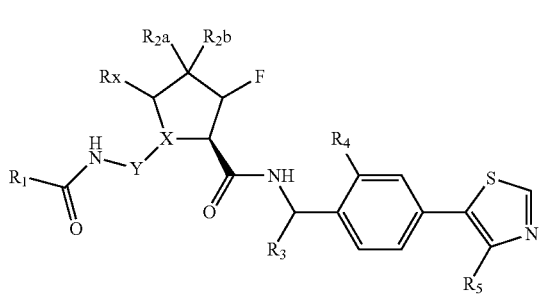

I wherein L is a group which is directly bonded to the compound of formula I and wherein L is —$(CH_2)_nL^1$$(CH_2O)_p$—, wherein $L^1$ is a covalent bond, a 5 or 6 membered heterocyclic or heteroaromatic ring containing 1, 2 or 3 nitrogen atoms, phenyl, —$(C_2$-$C_4)$alkyne, —$SO_2$—, or —NH—, wherein n and p are independently 0 to 10, wherein X is C or N, wherein $R^1$ is a covalent C-linked bond to L, —$(CH_2)_mQ_v$ group with a covalent C-linked bond to L, a $(C_1$-$C_4)$ alkyl group, or a C-linked $(C_3$-$C_4)$ heterocyclic group, wherein m is 0, 1 or 2 and v is 0 or 1, wherein Q is a $(C_3$-$C_4)$cyclic or $(C_3$-$C_4)$—C-linked nitrogen containing heterocyclic group, wherein one of the ring atoms in the Q group is optionally substituted with a —NHC(O) group or a —C(O) group, wherein said $R^1$ groups may be optionally substituted by one or more groups independently selected from F, CN, C(O) or C(O)($C_1$-$C_3$)alkyl, wherein $R^{2a}$ is OH, —$CHF_2$, —$CF_3$, $NH_2$ or F, wherein $R^{2b}$ is H, $^2$H, $^3$H, a —($C_1$-$C_3$) alkyl group, an aryl group, a heteroaryl group, —$CF_3$, —$CF_2$H, a —$CF_2$—($C_1$-$C_2$) alkyl group, or F, wherein $R^x$ is H, OH, —$CHF_2$, —$CF_3$, $NH_2$ or F, wherein $R^3$ and $R^4$ are independently selected from H, a covalent C-linked, a covalent O-linked, or a covalent C(O)-linked bond to L, $R^5$ is a —($C_1$-$C_3$) alkyl group or a covalent C-linked bond to L, wherein Y is

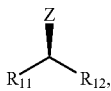

wherein Z is $CR^6R^7R^8$ or $SR^6R^7R^8R^9R^{10}$, wherein $R^{11}$ is a covalent C-linked bond or a

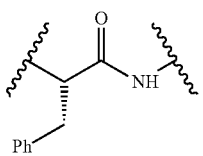

group, wherein $R^{12}$ is —C(O)—, —C(S)— or a —C(=)—$R^{13}$ group, wherein when Z is $CR^6R^7R^8$, $R^6$ and $R^7$ are each independently —($C_1$-$C_3$) alkyl groups, or wherein $R^6$ and $R^7$ together with the C-atom to which they are attached form a —($C_3$-$C_4$) cycloalkyl group, wherein when Z is $CR^6R^7R^8$, $R^8$ is a —($C_1$-$C_3$) alkyl group, a —($CH_2$)$_q$$R^{8*}$ group wherein q is 0, 1 or 2, a —C(O)—$R^{8*}$ group, or a —N(H)—$R^{8*}$ group, and wherein $R^{8*}$ is a covalent C-, S-, or N-linked bond to L, or H, or wherein when Z is $SR^6R^7R^8R^9R^{10}$, $R^6$, $R^7$, $R^8$, $R^9$ and $R^{10}$ are each independently selected from: F; or —($C_1$-$C_3$) alkyl groups, wherein $R^{13}$ is H, F or a-($C_1$-$C_3$) alkyl group, wherein the —($C_1$-$C_3$) alkyl groups where present in a Y group are optionally substituted by one or more substituents independently selected from OH or F, or —($C_3$-$C_4$) cycloalkyl groups where present in a Y group are optionally substituted by one or more substituents independently selected from: methyl; OH; or F, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

Advantageously, the novel small molecule E3 binding ligands of formula I, or formula IA as detailed herein are capable of being linked to the target protein binding ligand B, via linker L at a number of different positions on I or IA via a covalent C-linked bond to L at the $R^1$, $R^3$, $R^4$, $R^5$, or $R^8$ positions. Thus, according to a further aspect the present invention provides having the structure A-L-B wherein A is an E3 ubiquitin ligase protein binding ligand compound of formula I, or formula IA wherein A is linked to B via a covalent bond between A and L at a position on the compound of formula I or formula IA independently selected from: $R^1$, $R^3$, $R^4$, $R^5$, or $R^8$ as defined herein.

The present invention provides compounds having the structure A-L-B wherein A is an E3 ubiquitin ligase protein binding ligand compound of formula I wherein L is —($CH_2$)$_n$ $L^1$($CH_2$O)$_p$—, wherein $L^1$ is a covalent bond, a 5 or 6 membered heterocyclic or heteroaromatic ring containing 1, 2 or 3 nitrogen atoms, phenyl, —($C_2$-$C_4$)alkyne, —$SO_2$—, or —NH—, wherein X is C or N, wherein n and p are independently 0 to 10, wherein $R^1$ is a covalent C-linked bond to L, a —($CH_2$)$_m$$Q_v$ group with a covalent C-linked bond to L, a ($C_1$-$C_4$) alkyl group, or a C-linked ($C_3$-$C_4$) heterocyclic group, wherein m is 0, 1 or 2 and v is 0 or 1, and wherein when m is 0, v is 1, wherein Q is a ($C_3$-$C_4$)cyclic or ($C_3$-$C_4$)—C-linked nitrogen containing heterocyclic group, wherein one of the ring atoms in the Q group is optionally substituted with a —NHC(O) group or a —C(O) group, wherein said $R^1$ groups may be optionally substituted by one or more groups independently selected from F, CN, C(O) or C(O)($C_1$-$C_3$)alkyl, wherein $R^{2a}$ is OH, —$CHF_2$, —$CF_3$, $NH_2$ or F, wherein $R^{2b}$ is H, $^2$H, $^3$H, a —($C_1$-$C_3$) alkyl group, an aryl group, a heteroaryl group, —$CF_3$, —$CF_2$H, a —$CF_2$—($C_1$-$C_2$) alkyl group, wherein $R^3$ and $R^4$ are independently selected from H, a covalent C-linked, a covalent O-linked, or a covalent C(O)-linked bond to L, wherein $R^5$ is a —($C_1$-$C_3$) alkyl group or a covalent C-linked bond to L, wherein Y is

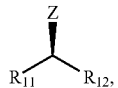

wherein Z is $CR^6R^7R^8$ or $SR^6R^7R^8R^9R^{10}$, wherein $R^{11}$ is a covalent C-linked bond or a

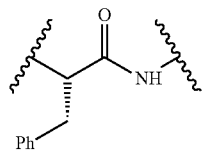

group, wherein $R^{12}$ is a —C(O)— group, wherein when Z is $CR^6R^7R^8$, $R^6$ and $R^7$ are each independently —($C_1$-$C_3$) alkyl groups or wherein $R^6$ and $R^7$ together with the C-atom to which they are attached form a —($C_3$-$C_4$) cycloalkyl group, and wherein when Z is $CR^6R^7R^8$, $R^8$ is a —($C_1$-$C_3$) alkyl group, a —($CH_2$)$_q$$R^{8*}$ group wherein q is 0, 1 or 2, a —C(O)—$R^{8*}$ group, or a —N(H)—$R^{8*}$ group, wherein $R^{8*}$ is a covalent C-, or S-linked bond to L, or H, or wherein when Z is $SR^6R^7R^8R^9R^{10}$, $R^6$, $R^7$, $R^8$, $R^9$ and $R^{10}$ are each independently selected from F or —($C_1$-$C_3$) alkyl groups, wherein $R^{13}$ is H, F or a-($C_1$-$C_3$) alkyl group, and wherein the —($C_1$-$C_3$) alkyl groups, or —($C_3$-$C_4$) cycloalkyl groups are optionally substituted by one or more substituents independently selected from: methyl; OH; or F, and wherein B is a ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof The present invention provides compounds having the structure A-L-B wherein A is an E3 ubiquitin ligase protein binding ligand compound of formula I, or formula IA or IB as defined in any aspect herein wherein L is a —(CH$_2$)$_n$(CH$_2$O)$_p$— group which is directly bonded to the compound of formula I, wherein n and p have the same value and are between 1 to 6, and preferably wherein L is a —(CH$_2$CH$_2$O)$_b$— group wherein b is 1 to 10.

The present invention provides compounds having the structure A-L-B wherein A is an E3 ubiquitin ligase protein binding ligand compound of formula I, IA, or IB and L is a linker as detailed hereinbefore and wherein B is present.

The present invention provides compounds having the structure A-L-B wherein A is an E3 ubiquitin ligase protein binding ligand compound of formula I, IA, or IB and L is a linker in accordance with any of the aspects as detailed above, wherein Y is

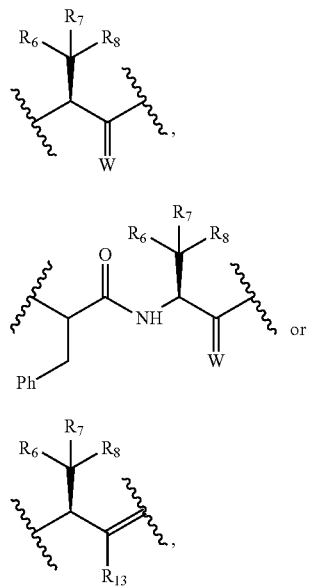

wherein R$^6$ R$^7$, R$^8$ and R$^{13}$ are as defined hereinbefore and wherein W may be O or S.

In preferred aspects the present invention provides compounds having the structure A-L-B wherein A is an E3 ubiquitin ligase protein binding ligand compound of formula I, and L is a linker in accordance with any of the aspects as detailed above, wherein Y is Y$_A$ or Y$_B$ and wherein W is O, more preferably Y is Y$_A$ and W is O.

In a preferred group of compounds of Formula I, IA, or IB, for use in PROTACs of structure A-L-B as defined hereinbefore, Y is Y$_A$, Y$_B$, or Y$_C$, preferably wherein Y is Y$_A$ or Y$_B$ and more preferably wherein Y is Y$_A$ or Y$_B$ and wherein when Y is Y$_A$ W is O and R$^6$, R$^7$ and R$^8$ are methyl groups; and when Y is Y$_B$ W is O and R$^6$, R$^7$ and R$^8$ are methyl groups. In a more preferred group of compounds of Formula I, IA, or IB, for use in PROTACs of structure A-L-B as defined hereinbefore, Y is Y$_A$, W is O and R$^6$, R$^7$ and R$^8$ are methyl groups.

Thus the present invention provides compounds having the structure A-L-B wherein A is an E3 ubiquitin ligase protein binding ligand compound of formula I, IA or IB, wherein R$^1$ to R$^5$, X, L and B are in accordance with any of the aspects defined herein and wherein Y is Y$_A$, Y$_B$, or Y$_C$, W is O or S, preferably wherein Y is Y$_A$, or Y$_B$ and W is O or S, more preferably wherein when Y is Y$_A$ W is O and R$^6$, R$^7$ and R$^8$ are methyl groups; and when Y is Y$_B$ W is O and R$^6$, R$^7$ and R$^8$ are methyl group, and especially wherein Y is Y$_A$, W is O and R$^6$, R$^7$ and R$^8$ are methyl groups.

In a preferred group of compounds of Formula I, IA or IB, for use in PROTACs of structure A-L-B as defined hereinbefore, and wherein L is a —(CH$_2$CH$_2$O)$_b$— group which is directly bonded to the compound of formula I wherein b is 1 to 10, preferably 1 to 6, more preferably 1 to 4, and particularly 2, 3 or 4.

Thus the present invention provides compounds having the structure A-L-B wherein A is an E3 ubiquitin ligase protein binding ligand compound of formula I, wherein R$^1$ to R$^5$, X, Y and B are in accordance with any of the aspects defined herein and wherein L is a —(CH$_2$CH$_2$O)$_b$— group which is directly bonded to the compound of formula I, wherein b is 1 to 10, preferably 1 to 6, more preferably 1 to 4, and particularly 2, 3 or 4.

The present invention provides compounds having the structure A-L-B wherein A is an E3 ubiquitin ligase protein binding ligand compound of formula I, and preferably wherein A is an E3 ubiquitin ligase protein binding ligand compound of formula IA as defined hereinafter, wherein X is N, wherein R$^1$ is a covalent C-linked bond to L, a —(CH$_2$)$_m$Q$_v$ group with a covalent C-linked bond to L, a (C$_1$-C$_4$) alkyl group, or a C-linked (C$_3$-C$_4$) heterocyclic group, wherein m is 0, 1 or 2 and v is 0 or 1, and wherein when m is 0, v is 1, wherein Q is a (C$_3$-C$_4$)cyclic or (C$_3$-C$_4$)—C-linked nitrogen containing heterocyclic group, wherein one of the ring atoms in the Q group is optionally substituted with a —NHC(O) group or a —C(O) group, wherein said R$^1$ groups may be optionally substituted by one or more groups independently selected from F, CN, C(O), or C(O)CH$_3$, wherein R$^{2a}$ is OH, wherein R$^{2b}$ is H, $^2$H, or $^3$H, wherein R$^x$ is H, wherein R$^3$ and R$^4$ are independently selected from H, a covalent C-linked, a covalent O-linked, or a covalent C(O)-linked bond to L, R$^5$ is a —(C$_1$-C$_3$) alkyl group or a covalent C-linked bond to L, wherein Y is

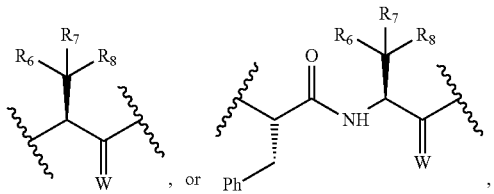

wherein W is O, wherein R$^6$ and R$^7$ are each independently —(C$_1$-C$_3$) alkyl groups, or wherein R$^6$ and R$^7$ together with the C-atom to which they are attached form a —(C$_3$-C$_4$) cycloalkyl group, wherein R$^8$ is a —(C$_1$-C$_3$) alkyl group, a —(CH$_2$)$_q$R$^{8*}$ group wherein q is 0, 1 or 2, a —C(O)—R$^{8*}$ group, or a —N(H)—R$^{8*}$ group, and wherein R$^{8*}$ is a covalent C-, S-, or N-linked bond to L, or H, wherein the —(C$_1$-C$_3$) alkyl groups, or —(C$_3$-C$_4$) cycloalkyl groups where present in a Y group are optionally substituted by one or more substituents independently selected from: methyl; OH; or F, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

There is additionally provided herein compounds having the structure A-L-B wherein A is an E3 ubiquitin ligase protein binding ligand compound of formula IA:

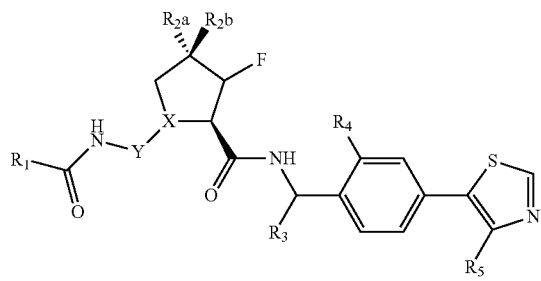

IA wherein X is N,
wherein $R^1$ is a covalent C-linked bond to L, a —$(CH_2)_mQ_v$ group with a covalent C-linked bond to L, a $(C_1-C_4)$ alkyl group, or a C-linked $(C_3-C_4)$ heterocyclic group, wherein m is 0, 1 or 2 and v is 0 or 1, and wherein when m is 0, v is 1, wherein Q is a $(C_3-C_4)$ cyclic or $(C_3-C_4)$—C-linked nitrogen containing heterocyclic group, wherein one of the ring atoms in the Q group is optionally substituted with a —NHC(O) group or a —C(O) group, wherein said $R^1$ groups may be optionally substituted by one or more groups independently selected from F, CN, C(O) or C(O)CH$_3$, wherein $R^{2a}$ is OH, wherein $R^{2b}$ is H, wherein $R^3$ and $R^4$ are independently selected from H, a covalent C-linked, a covalent O-linked, or a covalent C(O)-linked bond to L, wherein $R^5$ is a —$(C_1-C_3)$ alkyl group or a covalent C-linked bond to L, wherein Y is

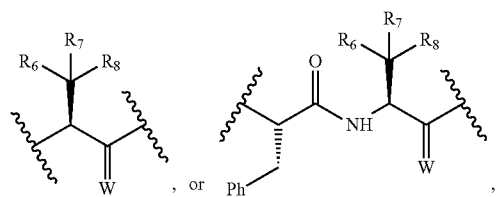

, or wherein W is O, and preferably wherein Y is a —$C(CR^6R^7R^8)$—C(O)— group, wherein $R^6$ and $R^7$ are each independently —$(C_1-C_3)$ alkyl groups, or wherein $R^6$ and $R^7$ together with the C-atom to which they are attached form a —$(C_3-C_4)$ cycloalkyl group, wherein $R^8$ is a —$(C_1-C_3)$ alkyl group, a —$(CH_2)_qR^{8*}$ group wherein q is 0, 1 or 2, a —C(O)—$R^{8*}$ group, or a —N(H)—$R^{8*}$ group, and wherein $R^{8*}$ is a covalent C-, S-, or N-linked bond to L, or H, wherein the —$(C_1-C_3)$ alkyl groups, or —$(C_3-C_4)$ cycloalkyl groups where present in a Y group are optionally substituted by one or more substituents independently selected from: methyl; OH; or F, wherein B is a ligand which binds to a target protein or polypeptide which is to be degraded by ubiquitin ligase and is linked to A though a —C-linkage to the L group, and preferably wherein B is a chemical moiety which selectively induces degradation of the BRD4 protein within the bromo- and Extra-terminal (BET) family of proteins, and especially wherein B is independently selected from: JQ1; I-BET726; I-BET762, or a pharmaceutically acceptable salt, enantiomer, stereoisomer, hydrate, solvate, or polymorph thereof. The present invention provides compounds having the structure A-L-B wherein A is an E3 ubiquitin ligase protein binding ligand compound of formula I, and L is a linker in accordance with any of the aspects as detailed above, wherein A has the general formula IA wherein X, Y, L, $R_1$, $R^{2a}$, $R^{2b}$, $R^x$, $R^3$, $R^4$, and $R^5$, are as indicated in formula IA, wherein $R^1$ is a covalent C-linked bond to L, a —$(CH_2)_mQ_v$ group with a covalent C-linked bond to L, or a $(C_1-C_4)$ alkyl group, wherein m is 0, or 1 and v is 0 or 1, and wherein when m is 0, v is 1, wherein Q is a $(C_3-C_4)$cyclic group, wherein one of the ring atoms in the Q group is optionally substituted with a —NHC(O) group or a —C(O) group, wherein said $R^1$ groups may be optionally substituted by one or more groups independently selected from F, CN, C(O), or C(O)CH$_3$, wherein $R^3$ and $R^4$ are independently selected from H, a covalent C-linked, a covalent O-linked, or a covalent C(O)-linked bond to L, $R^5$ is a —$(C_1-C_2)$ alkyl group or a covalent C-linked bond to L, wherein Y is a —$C(CR^6R^7R^8)$—C(O)— group, wherein $R^6$ and $R^7$ are each independently —$(C_1-C_3)$ alkyl groups, or wherein $R^6$ and $R^7$ together with the C-atom to which they are attached form a —$(C_3-C_4)$ cycloalkyl group, wherein $R^8$ is a —$(C_1-C_3)$ alkyl group, a —$(CH_2)_qR^{8*}$ group wherein q is 0, 1 or 2, a —C(O)—$R^{8*}$ group, or a —N(H)—$R^{8*}$ group, and wherein $R^{8*}$ is a covalent C-, S-, or N-linked bond to L, or H, wherein the —$(C_1-C_3)$ alkyl groups, or —$(C_3-C_4)$ cycloalkyl groups where present in a Y group are optionally substituted by one or more substituents independently selected from: methyl; OH; or F, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

The present invention provides PROTAC compounds having the structure A-L-B wherein A is an E3 ubiquitin ligase protein binding ligand compound of formula I, and L is a linker in accordance with any of the aspects as detailed above, wherein A has the general formula IA, wherein $R^1$ is a covalent C-linked bond to L, a cyclopropyl group with a covalent C-linked bond to L, or a C1 alkyl group, and wherein said C1 alkyl or cyclopropyl groups are optionally substituted by F, CN, or —C(O)CH$_3$, and wherein $R^8$ is a —$(C_1-C_3)$ alkyl group, or a —$(CH_2)_qR^{8*}$ group wherein q is 0, 1 or 2, wherein $R^{8*}$ is a covalent C-, S-, or N-linked bond to L, or H.

The present invention provides PROTAC compounds having the structure A-L-B wherein A is an E3 ubiquitin ligase protein binding ligand compound of formula I, L is a linker in accordance with any of the aspects as detailed hereinbefore, wherein A has the general formula IA, wherein $R^1$ is a covalent C-linked bond to L, a cyclopropyl group or a cyclopropyl group substituted with F, CN or C(O)CH$_3$ at the C1-position of the cycloalkyl ring wherein said cyclopropyl groups are covalently C-linked to L, or an unsubstituted methyl group, wherein $R^5$ is an unsubstituted methyl group or a covalent C-linked bond to L, wherein $R^6$ and $R^7$ are each independently unsubstituted $(C_1-C_2)$ alkyl groups, and wherein $R^8$ is an unsubstituted methyl or ethyl group, or a —$(CH_2)_qR^{8*}$ group wherein q is 0 or 1, wherein $R^{8*}$ is a covalent C-, S-, or N-linked bond to L, or H.

The present invention additionally provides PROTAC compounds having the structure A-L-B wherein A is an E3 ubiquitin ligase protein binding ligand compound of formula I, more preferably IA or IB as defined herein, wherein $R^1$, $R^{2a}$, $R^{2b}$, $R^x$, $R^3$, $R^4$, $R^6$, $R^7$, $R^9$, X, Y, L and B are as defined in accordance with any of the PROTAC compounds hereinbefore and wherein $R^5$ is a —$CH_3$ group or a covalent C-linked bond to L.

The present invention additionally provides PROTAC compounds having the structure A-L-B wherein A is an E3 ubiquitin ligase protein binding ligand compound of formula I, more preferably IA or IB as defined herein, wherein $R^1$, $R^{2a}$, $R^{2b}$, $R^x$, $R^3$, $R^4$, $R^6$, $R^7$, $R^9$, X, Y, and B are as defined in accordance with any of the PROTAC compounds hereinbefore and wherein L is a —$(CH_2CH_2O)_b$— group wherein b is 1 to 10 and wherein L is directly bonded to the compound of formula I, or IA, or IB.

The present invention provides PROTAC compounds having the structure A-L-B wherein A is an E3 ubiquitin ligase protein binding ligand compound of formula I, L is a linker in accordance with any of the aspects as detailed hereinbefore, wherein A has the general formula IB:

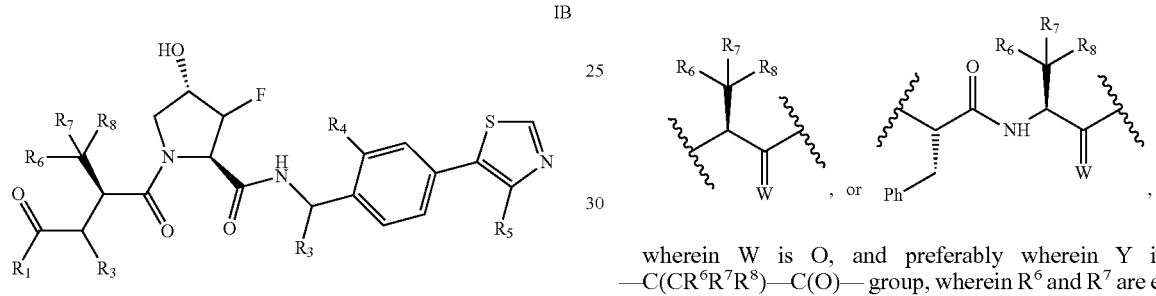

IB wherein L is a group which is directly bonded to the compound of formula IB and wherein L is —$(CH_2)_nL^1(CH_2O)_p$—, wherein $L^1$ is a covalent bond, a 5 or 6 membered heterocyclic or heteroaromatic ring containing 1, 2 or 3 nitrogen atoms, phenyl, —$(C_2-C_4)$alkyne, —$SO_2$—, or —NH—, wherein n and p are independently 0 to 10, wherein $R^1$ is a covalent C-linked bond to L, —$(CH_2)_mQ_v$ group with a covalent C-linked bond to L, a $(C_1-C_4)$ alkyl group, or a C-linked $(C_3-C_4)$ heterocyclic group, wherein m is 0, 1 or 2 and v is 0 or 1, wherein Q is a $(C_3-C_4)$cyclic or $(C_3-C_4)$—C-linked nitrogen containing heterocyclic group, wherein one of the ring atoms in the Q group is optionally substituted with a —NHC(O) group or a —C(O) group, wherein said $R^1$ groups may be optionally substituted by one or more groups independently selected from F, CN, C(O) or C(O)$(C_1-C_3)$ alkyl, wherein $R^3$ and $R^4$ are independently selected from H, a covalent C-linked, a covalent O-linked, or a covalent C(O)-linked bond to L, wherein $R^5$ is a —$(C_1-C_3)$ alkyl group or a covalent C-linked bond to L; $R^6$ and $R^7$ are each independently —$(C_1-C_3)$ alkyl groups, or wherein $R^6$ and $R^7$ together with the C-atom to which they are attached form a —$(C_3-C_4)$ cycloalkyl group, $R^8$ is a —$(C_1-C_3)$ alkyl group, a —$(CH_2)_qR^{8*}$ group wherein q is 0, 1 or 2, a —C(O)—$R^{8*}$ group, or a —N(H)—$R^{8*}$ group, and wherein $R^{8*}$ is a covalent C-, S-, or N-linked bond to L, or H, wherein the —$(C_1-C_3)$ alkyl groups, or —$(C_3-C_4)$ cycloalkyl groups where present are optionally substituted by one or more substituents independently selected from: methyl; OH; or F, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

In a preferred group of PROTAC compounds having the structure A-L-B wherein A is an E3 ubiquitin ligase protein binding ligand compound of formula I, L is a linker in accordance with any of the aspects as detailed hereinbefore, wherein A has the general formula IB, wherein X is N, $R^{2a}$ is OH, $R^{2b}$ is H, $R^x$ is H, Y is $Y_A$ and W is O, wherein $R^1$ is a covalent C-linked bond to L, a —$(CH_2)_mQ_v$ group with a covalent C-linked bond to L, a $(C_1-C_4)$ alkyl group, or a C-linked $(C_3-C_4)$ heterocyclic group, wherein m is 0, 1 or 2 and v is 0 or 1, and wherein when m is 0, v is 1, wherein Q is a $(C_3-C_4)$cyclic or $(C_3-C_4)$—C-linked nitrogen containing heterocyclic group, wherein one of the ring atoms in the Q group is optionally substituted with a —NHC(O) group or a —C(O) group, wherein said $R^1$ groups may be optionally substituted by one or more groups independently selected from F, CN, C(O) or C(O)$CH_3$, wherein $R^3$ and $R^4$ are independently selected from H, a covalent C-linked, a covalent O-linked, or a covalent C(O)-linked bond to L, wherein $R^5$ is a —$(C_1-C_3)$ alkyl group or a covalent C-linked bond to L, wherein Y is wherein W is O, and preferably wherein Y is a —C($CR^6R^7R^8$)—C(O)— group, wherein $R^6$ and $R^7$ are each independently —$(C_1-C_3)$ alkyl groups, or wherein $R^6$ and $R^7$ together with the C-atom to which they are attached form a —$(C_3-C_4)$ cycloalkyl group, wherein $R^8$ is a —$(C_1-C_3)$ alkyl group, a —$(CH_2)_qR^{8*}$ group wherein q is 0, 1 or 2, a —C(O)—$R^{8*}$ group, or a —N(H)—$R^{8*}$ group, and wherein $R^{8*}$ is a covalent C-, S-, or N-linked bond to L, or H, wherein the —$(C_1-C_3)$ alkyl groups, or —$(C_3-C_4)$ cycloalkyl groups where present in a Y group are optionally substituted by one or more substituents independently selected from: methyl; OH; or F, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

There is additionally provided herein groups of preferred PROTAC compounds, Groups I, II, III, IV and V, wherein the compound of formula I, has general formula IA wherein X is N, $R^{2a}$ is OH, $R^{2b}$ and $R^x$ are both H in each of the groups L is directly bonded to the compound of general formula IA at a different position, $R^1$ (Group I), $R^3$ (Group II), $R^4$ (Group III), $R^5$ (Group IV) or $R^8$ (Group V) respectfully. These groups of compounds are all compounds within general formula IB. Examples of compounds of formula IB within Groups I, II, III and IV are provided hereinafter.

In a preferred group of PROTAC compounds, Group I, having the structure A-L-B wherein A is an E3 ubiquitin ligase protein binding ligand compound of formula I, L is a linker in accordance with any of the aspects as detailed hereinbefore, wherein A has the general formula IB, wherein L is —$(CH_2)_nL^1(CH_2O)_p$—, wherein $L^1$ is a covalent bond, a 5 or 6 membered heterocyclic or heteroaromatic ring containing 1, 2 or 3 nitrogen atoms, phenyl, —$(C_2-C_4)$ alkyne, —$SO_2$—, or —NH—, and wherein L is directly bonded to the compound of formula IA at the $R^1$ position, wherein $R^1$ is an optionally substituted cyclopropyl group with a covalent C-linked bond to L or $R^1$ is a covalent C-Linked bond to L, wherein $R^3$ and $R^4$ are both H, wherein $R^5$ is a —$CH_3$ group, wherein Y is

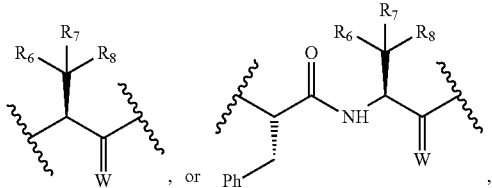

wherein W is O, and preferably wherein Y is a —$C(CR^6R^7R^8)$—$C(O)$— group, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

In a preferred group of Group I, PROTAC compounds having the structure A-L-B wherein A is an E3 ubiquitin ligase protein binding ligand compound of formula I, L is a linker in accordance with any of the aspects as detailed hereinbefore, wherein A has the general formula IA, wherein L is a —$(CH_2CH_2O)_b$— group wherein b is 1 to 10 and wherein L is directly bonded to the compound of formula IA at the $R^1$ position, wherein $R^1$ is an optionally substituted cyclopropyl group with a covalent C-linked bond to L or $R^1$ is a covalent C-Linked bond to L, wherein $R^3$ and $R^4$ are both H, wherein $R^5$ is a —$CH_3$ group, wherein Y is a —$C(CR^6R^7R^8)$—$C(O)$— group and wherein B is as defined hereinbefore.

In a preferred group of PROTAC compounds, Group II, having the structure A-L-B wherein A is an E3 ubiquitin ligase protein binding ligand compound of formula I, L is a linker in accordance with any of the aspects as detailed hereinbefore, wherein A has the general formula IB, wherein L is directly bonded to the compound of formula IA at the $R^3$ position, wherein L is —$(CH_2)_nL^1(CH_2O)_p$—, wherein $L^1$ is a covalent bond, a 5 or 6 membered heterocyclic or heteroaromatic ring containing 1, 2 or 3 nitrogen atoms, phenyl, —$(C_2-C_4)$alkyne, —$SO_2$—, or —NH—, wherein $R^{2a}$ is OH, wherein $R^{2b}$, $R^x$, and $R^4$ are all H, wherein $R^3$ is a covalent C-linked, a covalent O-linked, or a covalent —C(O)-linked bond to L, wherein $R^5$ is a —$CH_3$ group, wherein Y is

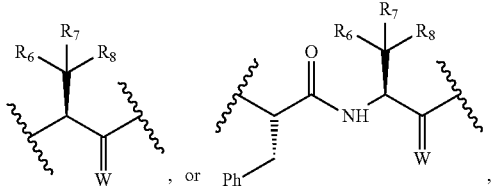

wherein W is O, and preferably wherein Y is a —$C(CR^6R^7R^8)$—$C(O)$— group.

In a preferred group of Group II, PROTAC compounds having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula IA at the $R^3$ position, wherein b is 1 to 10, wherein $R^{2a}$ is OH, wherein $R^{2b}$, $R^x$, $R^3$ and $R^4$ are all H, wherein $R^3$ is a covalent C-linked, a covalent O-linked, or a covalent —C(O)-linked bond to L, wherein $R^5$ is a —$CH_3$ group, and wherein Y is a —$C(CR^6R^7R^8)$—$C(O)$— group.

In a preferred group of PROTAC compounds, Group III, having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula IA at the $R^4$ position, wherein L is —$(CH_2)_nL^1(CH_2O)_p$—, wherein $L^1$ is a covalent bond, a 5 or 6 membered heterocyclic or heteroaromatic ring containing 1, 2 or 3 nitrogen atoms, phenyl, —$(C_2-C_4)$alkyne, —$SO_2$—, or —NH—, wherein $R^{2a}$ is OH, wherein $R^{2b}$, $R^x$, and $R^3$ are all H, wherein $R^4$ is a covalent C-linked, a covalent O-linked, or a covalent —C(O)-linked bond to L, wherein $R^5$ is a —$CH_3$ group, wherein Y is

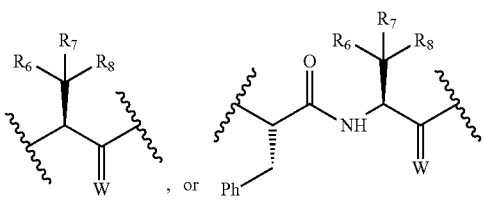

wherein W is O, and preferably wherein Y is a —$C(CR^6R^7R^8)$—$C(O)$— group.

In a preferred group of Group III, PROTAC compounds having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula IA at the $R^4$ position, wherein b is 1 to 10, wherein $R^{2a}$ is OH, wherein $R^{2b}$, $R^x$, and $R^3$ are all H, wherein $R^4$ is a covalent C-linked, a covalent O-linked, or a covalent —C(O)-linked bond to L, wherein $R^5$ is a —$CH_3$ group, and wherein Y is a —$C(CR^6R^7R^8)$—$C(O)$— group.

In a preferred group of PROTAC compounds, Group IV, having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula IA at the $R^5$ position, wherein L is —$(CH_2)_nL^1(CH_2O)_p$—, wherein $L^1$ is a covalent bond, a 5 or 6 membered heterocyclic or heteroaromatic ring containing 1, 2 or 3 nitrogen atoms, phenyl, —$(C_2-C_4)$alkyne, —$SO_2$—, or —NH—, wherein $R^{2a}$ is OH, wherein $R^{2b}$, $R^x$, $R^3$ and $R^4$ are all H, wherein $R^5$ is a covalent C-linked, a covalent O-linked, or a covalent —C(O)-linked bond to L, wherein Y is

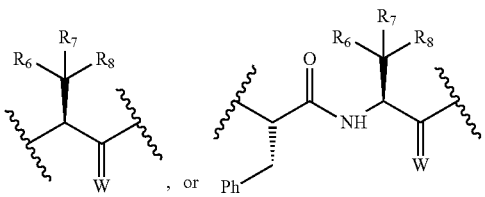

wherein W is O, and preferably wherein Y is a —C(CR⁶R⁷R⁸)—C(O)— group.

In a preferred group of Group IV, PROTAC compounds having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula IA at the R⁵ position, wherein b is 1 to 10, wherein R²ᵃ is OH, wherein R²ᵇ, Rˣ, R³ and R⁴ are all H, wherein R⁵ is a covalent C-linked, a covalent O-linked, or a covalent —C(O)-linked bond to L, and wherein Y is a —C(CR⁶R⁷R⁸)—C(O)— group.

In a preferred group of PROTAC compounds, Group V, having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula I, or IA at the R⁸* position, wherein L is —(CH₂)ₙL¹(CH₂O)ₚ—, wherein L¹ is a covalent bond, a 5 or 6 membered heterocyclic or heteroaromatic ring containing 1, 2 or 3 nitrogen atoms, phenyl, —(C₂-C₄)alkyne, —SO₂—, or —NH—, wherein R²ᵃ is OH, wherein R²ᵇ, Rˣ, and R⁴ are all H, wherein R³ is a covalent C-linked, a covalent O-linked, or a covalent —C(O)-linked bond to L, wherein R⁵ is a —CH₃ group, wherein Y is

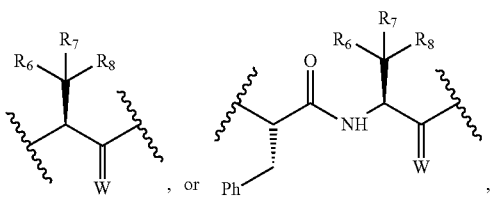

wherein W is O, and preferably wherein Y is a —C(CR⁶R⁷R⁸)—C(O)— group wherein R⁸ is a —(CH₂)_q R⁸* group wherein q is 0, 1 or 2, and wherein R⁸* is a covalent C-, S-, or N-linked bond to L.

In a preferred group of Group V, PROTAC compounds having the structure A-L-B wherein A is an E3 ubiquitin ligase protein binding ligand compound of formula I, L is a linker in accordance with any of the aspects as detailed hereinbefore, wherein A has the general formula IA, wherein L is directly bonded to the compound of formula IA at the R⁸* position, wherein L is a —(CH₂CH₂O)_b— group wherein b is 1 to 10, wherein R²ᵃ is OH, wherein R²ᵇ, Rˣ, R³ and R⁴ are all H, wherein R⁵ is a —CH₃ group, wherein Y is a-C(CR⁶R⁷R⁸)—C(O)— group, wherein R⁸ is a —(CH₂)_q R⁸* group wherein q is 0, 1 or 2, and wherein R⁸* is a covalent C-, S-, or N-linked bond to L.

PROTAC compounds having the structure A-L-B wherein A is an E3 ubiquitin ligase protein binding ligand compound of formula I, preferably of formula IA, more preferably formula IB, wherein L and B are in accordance with any of the aspects as detailed above, particularly wherein L is a PEG1 to PEG 4 groups and wherein B is independently selected from: JQ1; I-BET726; I-BET762, and wherein the L-group is directly bonded to the compound of Formula I or IA, or IB at the R¹ position are as defined hereinbefore and are as detailed hereinafter.

In addition, exemplary PROTAC compounds having the structure A-L-B wherein A is an E3 ubiquitin ligase protein binding ligand compound of formula I, preferably of formula IA, wherein L and B are in accordance with any of the aspects as detailed above, and wherein the L-group is directly bonded to the compound of Formula I or IA at the R¹, R³, R⁴, R⁵ or R⁸* positions are provided in Groups I to V as defined hereinafter.

There are also provided herein a group of PROTAC compounds having the structure A-L-B wherein A is an E3 ubiquitin ligase protein binding ligand compound of formula I, and L is a linker in accordance with any of the aspects, or preferred or particular aspects as detailed above, wherein A has the general formula IA, wherein R¹ to R⁵, X, L and B are as defined hereinbefore and wherein Y is Y_A, Y_B, or Y_C, preferably wherein Y is Y_A or Y_B and more preferably wherein Y is Y_A or Y_B, and especially wherein Y is Y_A, and wherein: when Y is Y_A W is O and R⁶, R⁷ and R⁸ are methyl groups; and when Y is Y_B W is O and R⁶, R⁷ and R⁸ are methyl groups.

As used herein, the following terms have the meanings as defined below, unless otherwise noted:

"C_a-C_b alkyl" on its own or in composite expressions such as C_a-C_b haloalkyl, etc. represents a straight or branched alkyl radical having the number of carbon atoms designated, e.g. C₁-C₄alkyl means an alkyl radical having from 1 to 4 carbon atoms. Preferred alkyl radicals for use in the present invention are C₁-C₄ alkyl, including methyl, ethyl, n-propyl, isopropyl, n-butyl, isobutyl, sec.butyl, and tert.butyl.

"C₂-C₄alkyne" represents a straight or branched alkyl radical having from 2 to 4 carbon atoms and one carbon-to-carbon triple bond, e.g. ethyne (C₂H₂), propyne (C₃H₄), and 1-butyne (C₄H₆).

The term "Me" means methyl, and "MeO" means methoxy.

The term "C_e-C_f cyclic" means a "C₃-C₄"cycloalkyl" group and represents a cyclic monovalent alkyl radical having the number of carbon atoms indicated, e.g. C₃-C₄cycloalkyl means a cyclic monovalent alkyl radical having 3 or 4 carbon atoms.

The term "amino" represents the radical —NH₂.

The term "halo" represents a halogen radical such as fluoro, chloro, bromo or iodo. Preferred halo group is fluoro.

The term "Ph" means phenyl, for example in R¹¹ or Y_B groups herein "Ph" represents the radical —C₆H₅.

The term "5 or 6 membered heterocyclic ring" represents a stable saturated monocyclic 5 or 6 membered ring containing 1, 2 or 3 nitrogen heteroatoms.

The term "5 or 6 membered heteroaromatic" or "heteroaryl" represents a stable monocyclic aromatic ring containing 1-3 nitrogen heteroatoms having 5 or 6 ring atoms.

Typical configurations of 5 or 6 membered heterocyclic or heteroaromatic rings for use as L groups herein include: triazole; diazole; pyrazole; pyrrolidine; pyrrroline; pyrrole; pyrazolidine; pyrazoline; pyrazole; piperidine; pyridine; piperazine; pyrazine; pyrimidine; pyrimidazine; triazine4,5-dihydroimidazole. Preferred configurations of 5 or 6 membered heterocyclic or heteroaromatic rings for use as L groups herein are 1,2,3-triazoles, 1,3-diazoles, and piperazines. Exemplary 5 or 6 membered heterocyclic or heteroaromatic rings for use as L groups herein are independently selected from:

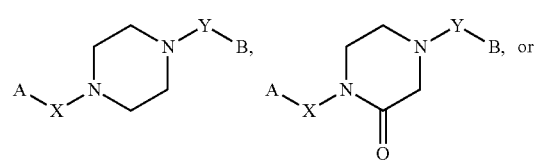

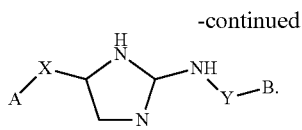

The term "C-linked (C$_3$-C$_4$) oxygen containing heterocyclic group" represents a stable saturated monocyclic 3 or 4 membered ring containing 1 oxygen or 1 nitrogen heteroatom. Typical configurations of 3 or 4 membered heterocyclic rings for use as R$^1$ groups herein include: aziridines; oxiranes; azetidines; and oxetanes. Preferred configurations of 3 or 4 membered heterocyclic rings for use as R$^1$ groups herein are oxiranes and azetidines. Exemplary 3 or 4 membered heterocyclic rings for use as R$^1$ groups herein are independently selected from:

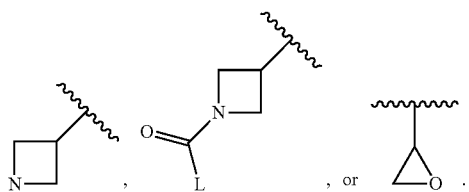

As used herein, the term "=O", i.e. in —C(O)—, forms a carbonyl moiety when attached to a carbon atom. It should be noted that an atom can only carry an oxo group when the valency of that atom so permits.

As used herein, the term, "=C", i.e. in —C(=)—R$^{13}$, denotes an unsaturated carbon-to-carbon double bond.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts suitable for use herein include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange.

Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulphonate.

The PROTAC compounds of the invention can be administered as pharmaceutically acceptable prodrugs which release the compounds of the invention in vivo. "Prodrug", as used herein means a compound which is convertible in vivo by metabolic means (e.g. by hydrolysis) to afford any compound delineated by the formulae of the instant invention. Various forms of prodrugs are known in the art, for example, as discussed in "Design and Application of Prodrugs, Textbook of Drug Design and Development, Chapter 5, 113-191 (1991); Bundgaard, et al., Journal of Drug Deliver Reviews, 8:1-38(1992); and Bernard Testa and Joachim Mayer, "Hydrolysis In Drug and Prodrug Metabolism—Chemistry, Biochemistry and Enzymology," John Wiley and Sons, Ltd. (2003).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Related terms, are to be interpreted accordingly in line with the definitions provided above and the common usage in the technical field.

The present invention also includes isotope-labelled PROTAC compounds of structure A-L-B, as well as compounds of formula I or any subgroup of formula I, wherein one or more of the atoms is replaced by an isotope of that atom, i.e. an atom having the same atomic number as, but an atomic mass different from, the one(s) typically found in nature. Examples of isotopes that may be incorporated into the PROTAC compounds of structure A-L-B, compounds of formula I, or any subgroup of formula I, include but are not limited to isotopes of hydrogen, such as $^2$H and $^3$H (also denoted D for deuterium and T for tritium, respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulphur, such as $^{35}$S, fluorine, such as $^{18}$F, chlorine, such as $^{36}$Cl, bromine such as $^{75}$Br, $^{76}$Br, $^{77}$Br and $^{82}$Br, and iodine, such as $^{123}$I, $^{124}$I, $^{125}$I and $^{131}$I. The choice of isotope included in an isotope-labelled compound will depend on the specific application of that compound. For example, for drug or substrate tissue distribution assays, compounds wherein a radioactive isotope such as $^3$H or $^{14}$C is incorporated will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^2$H, may provide greater metabolic stability to a PROTAC compound of structure A-L-B, a compound of formula I, or any subgroup of formula I, which may result in, for example, an increased in vivo half-life of the compound or reduced dosage requirements.

Isotope-labelled PROTAC compounds of structure A-L-B, compounds of formula I, or any subgroup of formula I can be prepared by processes analogous to those described in the Schemes and/or Examples herein below by using the appropriate isotope-labelled reagent or starting material instead of the corresponding non-isotope-labelled reagent or starting material, or by conventional techniques known to those skilled in the art.

In a preferred aspect herein the compounds of formula I for use in the PROTAC compounds of structure A-L-B- as defined herein are represented as a defined stereoisomer. The absolute configuration of such compounds can be determined using art-known methods such as, for example, X-ray diffraction or NMR and/or implication from starting materials of known stereochemistry.

Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers which are substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates as detailed herein may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo-specifically. Preferably, if a specific stereoisomer is desired, said compound is synthesized by stereospecific methods of preparation. These methods will advantageously employ enantiomerically pure starting materials.

The diastereomeric racemates of the compounds of formula I for use in the PROTAC compounds of structure A-L-B as defined herein can be obtained separately by conventional methods. Appropriate physical separation methods that may advantageously be employed are, for example, selective crystallization and chromatography, e.g. column chromatography.

The present invention provides PROTAC compounds having the structure A-L-B wherein A is an E3 ubiquitin ligase protein binding ligand compound of formula I or IA, and L is a linker in accordance with any of the aspects as detailed above, wherein B is a chemical moiety which selectively induces degradation of the BRD4 protein within the bromo- and Extra-terminal (BET) family of proteins, and optionally wherein B is independently selected from: JQ1; I-BET726; I-BET762.

The present invention provides PROTAC compounds of structure A-L-B wherein B is a chemical moiety which binds to a protein within the bromo- and Extra-terminal (BET) family of proteins, preferably PROTAC compounds of structure A-L-B wherein B is a chemical moiety which binds to a protein within the bromo- and Extra-terminal (BET) family of proteins independently selected from: BRD2, BRD3 and BRD4, and particularly PROTAC compounds of structure A-L-B wherein B is a chemical moiety which selectively induces degradation of the BRD4 protein within the bromo- and Extra-terminal (BET) family of proteins.

In a further aspect, the invention provides a PROTAC compound of structure A-L-B as defined herein for use as a medicament.

The term "subject" as used herein refers to a mammal. A subject therefore refers to, for example, dogs, cats, horses, cows, pigs, guinea pigs, and the like. Preferably the subject is a human. When the subject is a human, the subject may also be referred to herein as a patient.

"Treat", "treating" and "treatment" refer to a method of alleviating or abating a disease and/or its attendant symptoms.

The term "therapeutically effective amount" means an amount effective to treat, cure or ameliorate a disease, condition illness or sickness.

A further aspect of the invention provides a method for the prophylaxis or treatment of a disease or condition associated with deregulation of protein activity of one or more proteins within the the Bromo- and Extra-terminal (BET) family of proteins BRD2, BRD3 and BRD4 comprising the administration of a PROTAC compound of structure A-L-B to a subject suffering from or likely to be exposed to said disease or condition. A related aspect of the invention provides the use of a PROTAC compound of structure A-L-B in the treatment or prophylaxis of a disease or condition associated with deregulation of BET protein activity. A further related aspect provides the use of a PROTAC compound of structure A-L-B as defined herein for the treatment or prophylaxis of a disease or condition associated with deregulation of BET protein activity.

A further aspect of the invention provides a method for the prophylaxis or treatment of a disease or condition associated with deregulation of protein activity of one or more proteins within the the Bromo- and Extra-terminal (BET) family of proteins BRD2, BRD3 and BRD4 comprising the administration of a therapeutically effective amount of a PROTAC compound of structure A-L-B to a subject suffering from or likely to be exposed to said disease or condition. A related aspect of the invention provides the use of a therapeutically effective amount of a PROTAC compound of structure A-L-Bin the treatment or prophylaxis of a disease or condition associated with deregulation of BET protein activity. A further related aspect provides the use of a therapeutically effective amount of a PROTAC compound of structure A-L-B as defined herein for the treatment or prophylaxis of a disease or condition associated with deregulation of BET protein activity.

A further aspect of the invention provides a method for the prophylaxis or treatment of a disease or condition associated with selective degradation of the BRD4 protein within the bromodomain of the BET family of proteins comprising the administration of a PROTAC compound of structure A-L-B as defined herein to a subject suffering from or likely to be exposed to said disease or condition. A related aspect of the invention provides the use of a PROTAC compound of structure A-L-B in the treatment or prophylaxis of a disease or condition associated with selective degradation of the BRD4 protein within the bromodomain of the BET family of proteins. A further related aspect provides the use of a PROTAC compound of structure A-L-B for the treatment or prophylaxis of a disease or condition associated with selective degradation of the BRD4 protein within the bromodomain of the BET family of proteins.

Diseases or conditions associated with deregulation of protein activity of one or more proteins within the the Bromo- and Extra-terminal (BET) family of proteins BRD2, BRD3 and BRD4 which may be treated via the administration of a PROTAC compound of structure A-L-B as defined herein include: cancer; benign proliferative disorders; infectious or non-infectious inflammatory events; autoimmune diseases; inflammatory diseases; systemic inflammatory response syndromes; viral infections and diseases; and opthalmological conditions.

The present invention also provides PROTAC compounds structure A-L-B wherein B is a chemical moiety which binds to a protein within the bromo- and Extra-terminal (BET) family of proteins, and wherein A is a compound of formula I or formula IA in accordance with any aspect, or preferred aspect detailed herein for use in medicine, particularly for use in conditions or diseases where binding to a protein within the bromo- and Extra-terminal (BET) family of proteins independently selected from: BRD2, BRD3 and BRD4 is implicated, and especially for use in the treatment of one or more conditions or diseases independently selected from: cancer; benign proliferative disorders; infectious or non-infectious inflammatory events; autoimmune diseases; inflammatory diseases; systemic inflammatory response syndromes; viral infections and diseases; and opthalmological conditions.

There is also provided herein PROTAC compounds of formula A-L-B in accordance with any aspect herein, for use in the treatment of cancer and a method of treatment of cancer by administration of an effective amount of a PROTAC compound of formula A-L-B in accordance with any aspect herein, to a mammal, in particular a human in need of such treatment.

Cancer-types which may be treated via the administration of a PROTAC compound of structure A-L-B as defined herein include: carcinoma-type cancers associated with epithelial cells disorders such as for example breast cancer, prostate cancer, lung cancer pancreatic cancer and cancer of the colon; sarcoma-type cancers associated with mesenchymal cell disorders; lymphoma; leukemia, such as for example acute myeloid leukaemia; cancers and/or cancerous tumours associated with pluripotent cells such as testicular cancer and ovarian carcinoma.

Examples of cancers that the compounds of the present invention may be used in the treatment of include: adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, Wilms' tumor, hematological cancers (such as leukaemia), epithelial cancers including lung, breast and colon carcinomas, midline carcinomas, mesenchymal, hepatic, renal and neurological tumours.

Examples of benign proliferative disorders that the compounds of the present invention may be used in the treatment of include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

There is also provided herein PROTAC compounds of formula A-L-B in accordance with any aspect herein, for use in the treatment of infectious and non-infectious inflammatory events and autoimmune and other inflammatory diseases, disorders and syndromes and a method of treatment of infectious and non-infectious inflammatory events and autoimmune and other inflammatory diseases disorders and syndromes by administration of an effective amount of a PROTAC compound of formula A-L-B in accordance with any aspect herein, to a mammal, in particular a human in need of such treatment. Examples of infectious and non-infectious inflammatory events and autoimmune and other inflammatory diseases, disorders and syndromes that the compounds of the present invention may be used in the treatment of include but are not limited to: inflammatory pelvic disease (PID), gout, pleurisy, eczema, splenitis, laryngitis, thyroiditis, prostatitis, pharyngitis, sarcoidosis, seborrheic dermatitis, irritable bowel syndrome (IBS), diverticulitis, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergic reactions, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anaemia, glomerulonephritis, dermatomyositis, multiple sclerosis, some myopathies, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In other embodiments, the present invention provides PROTAC compounds of formula A-L-B in accordance with any aspect herein, for use in the treatment of systemic inflammatory response syndromes, and a method of treatment of systemic inflammatory response syndromes by administration of an effective amount of a PROTAC compound of formula A-L-B in accordance with any aspect herein, to a mammal, in particular a human in need of such treatment. Examples of systemic inflammatory response syndromes that the compounds of the present invention may be used in the treatment of include: LPS-induced endotoxic shock and/or bacteria-induced sepsis.

Autoimmune diseases and Autoimmune-related diseases which may be treated via the administration of a PROTAC compound of structure A-L-B as defined herein include: acute Disseminated Encephalomyelitis (ADEM); acute necrotizing hemorrhagic leukoencephalitis; Addison's disease; agammaglobulinemia; alopecia areata; amyloidosis; ankylosing spondylitis; anti-GBM/anti-TBM nephritis; antiphospholipid syndrome (APS); autoimmune angioedema; autoimmune aplastic anemia; autoimmune dysautonomia; autoimmune hepatitis; autoimmune hyperlipidemia; autoimmune immunodeficiency; autoimmune inner ear disease (AIED); autoimmune myocarditis; autoimmune oophoritis; autoimmune pancreatitis; autoimmune retinopathy; autoimmune thrombocytopenic purpura (ATP); autoimmune thyroid disease; autoimmune urticaria; axonal & neuronal neuropathies; Balo disease; Behcet's disease; bullous pemphigoid; cardiomyopathy; Castleman disease; celiac disease; Chagas disease; chronic fatigue syndrome; chronic inflammatory demyelinating polyneuropathy (CIDP); chronic recurrent multifocal ostomyelitis (CRMO); Churg-Strauss syndrome; cicatricial pemphigoid/benign mucosal pemphigoid; Crohn's disease; Cogans syndrome; cold agglutinin disease; congenital heart block; Coxsackie myocarditis; CREST disease; essential mixed cryoglobulinemia; demyelinating neuropathies; dermatitis herpetiformis; dermatomyositis; Devic's disease (neuromyelitis optica); discoid lupus; Dressler's syndrome; endometriosis; eosinophilic esophagitis; eosinophilic fasciitis; erythema nodosum; experimental allergic encephalomyelitis; Evans syndrome; fibromyalgia; fibrosing alveolitis; giant cell arteritis (temporal arteritis); giant cell myocarditis; glomerulonephritis; Goodpasture's syndrome; granulomatosis with polyangiitis (GPA) (formerly called Wegener's Granulomatosis); Graves' disease; Guillain-Barre syndrome; Hashimoto's encephalitis; Hashimoto's thyroiditis; hemolytic anemia; Henoch-Schonlein purpura; herpes gestationis; hypogammaglobulinemia; idiopathic thrombocytopenic purpura (ITP); IgA nephropathy; IgG4-related sclerosing disease; immunoregulatory lipoproteins; inclusion body myositis; interstitial cystitis; juvenile arthritis; juvenile diabetes (Type 1 diabetes); juvenile myositis; Kawasaki syndrome; Lambert-Eaton syndrome; leukocytoclastic vasculitis; lichen planus; lichen sclerosus; ligneous conjunctivitis; linear IgA disease (LAD); lupus (SLE); Lyme disease; Meniere's disease; microscopic polyangitis; mixed connective tissue disease (MCTD); Mooren's ulcer; Mucha-Habermann disease; multiple sclerosis; myasthenia gravis; myositis; narcolepsy; neuromyelitis optica (Devic's disease); neutropenia; ocular cicatricial pemphigoid; optic neuritis; palindromic rheumatism; PANDAS (Pediatric Autoimmune Neuropsychiatric Disorders Associated with *Streptococcus*); paraneoplastic cerebellar degeneration; paroxysmal nocturnal hemoglobinuria (PNH); Parry Romberg syndrome; Parsonnage-Turner syndrome; pars planitis (peripheral uveitis); pemphigus; peripheral neuropathy; perivenous encephalomyelitis; pernicious anemia; POEMS syndrome; polyarteritis *nodosa*; type I, II, & III autoimmune polyglandular syndromes; polymyalgia rheumatica; polymyositis; postmyocardial infarction syndrome; postpericardiotomy syndrome; progesterone dermatitis; primary biliary cirrhosis; primary sclerosing cholangitis; psoriasis; psoriatic arthritis; idiopathic pulmonary fibrosis; pyoderma gangrenosum; pure red cell aplasia; Raynauds phenomenon; reactive arthritis; reflex sympathetic dystrophy; Reiter's syndrome;

relapsing polychondritis; restless legs syndrome; retroperitoneal fibrosis; rheumatic fever; rheumatoid arthritis; sarcoidosis; Schmidt syndrome; scleritis; scleroderma; Sjogren's syndrome; sperm & testicular autoimmunity; stiff person syndrome; subacute bacterial endocarditis (SBE); Susac's syndrome; sympathetic ophthalmia; Takayasu's arteritis; temporal arteritis/giant cell arteritis; thrombocytopenic purpura (TTP); Tolosa-Hunt syndrome; transverse myelitis; type 1 diabetes; ulcerative colitis; undifferentiated connective tissue disease (UCTD); uveitis; vasculitis; vesiculobullous dermatosis; vitiligo; Wegener's granulomatosis (now termed Granulomatosis with Polyangiitis (GPA).

As will be readily appreciated by the skilled person there is a certain degree of overlap between conditions and diseases within those defined herein as inflammatory and autoimmune disorders or conditions, which is to be expected in view of the complex nature of such conditions and the presentations of each individual subject.

There is additionally provided herein PROTAC compounds of formula A-L-B in accordance with any aspect herein, for use in the treatment of viral infections and diseases, and a method of treatment of viral infections and diseases by administration of an effective amount of a PROTAC compound of formula A-L-B in accordance with any aspect herein, to a mammal, in particular a human in need of such treatment. Examples of viral infections and diseases that the compounds of the present invention may be used in the treatment of include: episome-based DNA viruses including, but not limited to, human papillomavirus, Herpesvirus, Epstein-Barr virus, human immunodeficiency virus, hepatis B virus, and hepatitis C virus.

There is also provided herein PROTAC compounds of formula A-L-B in accordance with any aspect herein, for use in the treatment of viral infections and a method of treatment of viral infections by administration of an effective amount of a PROTAC compound of formula A-L-B in accordance with any aspect herein, to a mammal, in particular a human in need of such treatment. Examples of viral infections that the compounds of the present invention may be used in the treatment of include herpes virus, human papilloma virus, adenovirus, poxvirus and other DNA viruses.

There is also provided herein PROTAC compounds of formula A-L-B in accordance with any aspect herein, for use in the treatment of ophthamological indications and a method of treatment of ophthamological indications by administration of an effective amount of a PROTAC compound of formula A-L-B in accordance with any aspect herein, to a mammal, in particular a human in need of such treatment. Examples of ophthamological indications that the compounds of the present invention may be used in the treatment of include dry eye.

A further aspect of the invention provides a method for the prophylaxis or treatment of a disease or condition associated with deregulation of BET protein activity comprising the administration of a PROTAC compound of structure A-L-B as defined herein to a subject suffering from or likely to be exposed to said disease or condition wherein said disease or condition is independently selected from: cancer; benign proliferative disorders; infectious or non-infectious inflammatory events; autoimmune diseases; inflammatory diseases; systemic inflammatory response syndromes; viral infections and diseases; and opthalmological conditions. A related aspect of the invention provides the use of a PROTAC compound of structure A-L-B as defined herein in the treatment or prophylaxis of a disease or condition associated with deregulation of BET protein activity wherein said disease or condition is independently selected from: cancer; benign proliferative disorders; infectious or non-infectious inflammatory events; autoimmune diseases; inflammatory diseases; systemic inflammatory response syndromes; viral infections and diseases; and opthalmological conditions. A further related aspect provides the use of a PROTAC compound of structure A-L-B as defined herein for the treatment or prophylaxis of a disease or condition associated with deregulation of BET protein activity wherein said disease or condition is independently selected from: cancer; benign proliferative disorders; infectious or non-infectious inflammatory events; autoimmune diseases; inflammatory diseases; systemic inflammatory response syndromes; viral infections and diseases; and opthalmological conditions.

There is also provided herein PROTAC compounds of formula A-L-B in accordance with any aspect herein, for use in the treatment of disease or condition for which a bromodomain inhibitor is indicated and a method of treatment of disease or condition for which a bromodomain inhibitor is indicated by administration of an effective amount of a PROTAC compound of formula A-L-B in accordance with any aspect herein, to a mammal, in particular a human in need of such treatment. Examples of disease or condition for which a bromodomain inhibitor is indicated that the compounds of the present invention may be used in the treatment of include diseases associated with systemic inflammatory response syndrome, such as sepsis, burns, pancreatitis, major trauma, haemorrhage and ischaemia.

In such uses or methods the PROTAC compound of structure A-L-B would preferably be administered to a subject in need of such treatment at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality.

Alternatively in other circumstances where there is a perceived high risk of sepsis, haemorrhage, extensive tissue damage, SIRS or MODS, the PROTAC compound of structure A-L-B would preferably be administered to a subject in need of such protection from such risks, for example prior to surgical or other procedures associated with a high risk of sepsis, haemorrhage, extensive tissue damage, SIRS or MODS.

According to a particular embodiment there is provided herein use of a PROTAC compounds of structure A-L-B for use in the treatment of sepsis, sepsis syndrome, septic shock and/or endotoxaemia.

According to another embodiment there is provided herein use of a PROTAC compounds of structure A-L-B for use in the treatment of the treatment of acute or chronic pancreatitis, or burns.

Further examples of diseases or conditions for which a bromodomain inhibitor is indicated and for which the PROTAC compounds of structure A-L-B may be used in the treatment of include herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

According to further embodiment there is provided herein use of a PROTAC compounds of structure A-L-B for use in the treatment of the treatment of Human papilloma virus infections of skin or cervical epithelia.

In a further aspect there is provided herein, a PROTAC compound of formula A-L-B for use in the treatment of any of the diseases or conditions indicated hereinbefore wherein said treatment modulates one or more of protein methylation, gene expression, cell proliferation, cell differentiation and/or apoptosis in vivo in the disease or condition being treated.

According to a further aspect there is provided a PROTAC compound of formula A-L-B for use in the modulation of one or more one or more of protein methylation, gene expression, cell proliferation, cell differentiation and/or apoptosis in vivo in the treatment of a disease or condition independently selected from: cancer; inflammatory disease; and/or viral disease.

According to another aspect there is provided a therapeutic method of modulating one or more of protein methylation, gene expression, cell proliferation, cell differentiation and/or apoptosis in vivo in the treatment of cancer, inflammatory disease and/or viral disease wherein said method is provided by administering a therapeutically effective amount of one or more PROTAC compounds of structure A-L-B to a subject in need of such therapy.

As demonstrated hereinafter, PROTAC compounds of the invention trigger the intracellular destruction of BET proteins.

As also discussed hereinafter certain non-fluorinated PROTAC compounds of structure A-L-B, and in particular compound MZ1 (Zengerle, M., Chan, K.-H., Ciulli, A. Selective Small Molecules Induced Degradation of the BET Bromodomain Protein BRD4. *ACS Chem. Biol.* 2015, 10(8), 1770-1777) potently and rapidly induce reversible, long-lasting and unexpectedly selective removal of BRD4 over BRD2 and BRD3. In addition, the Applicant has also found that gene expression profiles of selected cancer-related genes responsive to JQ1 have shown distinct and more limited transcriptional responses induced by MZ1. This is consistent with selective suppression of BRD4. For the reasons discussed hereinafter it is proposed herein that the present fluorinated PROTAC compounds of structure A-L-B, and in particular compounds wherein A is a compound of structure IA or more particularly IB, would also potently and rapidly induce reversible, long-lasting and unexpectedly selective removal of BRD4 over BRD2 and BRD3. In particular, as shown in FIG. 3, Applicant has found that compounds of formula IB as described above bind to the VHL ubiquitin ligase protein with a comparable affinity to previously reported non-fluorinated ligands. Furthermore, as illustrated in FIG. 6, PROTACs of formula I—as described above—can exhibit dose dependent degradation of the target protein.

Thus the invention provides compounds of formula 1 which bind to a protein within the bromo- and Extra-terminal (BET) family of proteins. The invention additionally provides PROTAC compounds of structure A-L-B, wherein L is as defined hereinbefore, wherein A is a compound of formula I or formula IA or formula IB as defined hereinbefore and wherein B is a chemical moiety which binds to a protein within the bromo- and Extra-terminal (BET) family of proteins, and wherein said protein is independently selected from: BRD2, BRD3 and BRD4. The invention particularly provides PROTAC compounds of structure A-L-B, wherein L is as defined hereinbefore, wherein A is a compound of formula I, or formula IA, or formula IB as defined hereinbefore and wherein B is a chemical moiety which selectively induces degradation of the BRD4 protein within the bromo- and Extra-terminal (BET) family of proteins.

As previously indicated to achieve intracellular BET-protein degradation the Applicant has utilized a small molecule PROTAC (PROteolysis TArgeting Chimera) approach. A PROTAC compound is a hetero-bi-functional compound that contains two ligands connected by a linker unit. In the PROTAC compounds, or PROTACs, according to the present invention one ligand (A), a compound of formula I, or IA, or IB as defined herein, binds to an E3 ubiquitin ligase protein and the other ligand (B) binds to the target protein of interest, thereby bringing the ligase and the target into close proximity.

Whilst not wishing to be bound to any particular theory it is proposed herein that it is this close proximity which in turn triggers the poly-ubiquitination and subsequent proteasome-dependent degradation of the target protein of interest. Supporting evidence for a PROTAC approach on a general level is provided by known proof-of-concept examples where alternative PROTACs have been used to degrade: the Estrogen-receptor, Cyrus, K., Wehenkel, M., Choi, E. Y., Swanson, H. & Kim, K. B., *"Two-headed PROTAC: An effective new tool for targeted protein degradation"*. ChemBioChem, 11, 1531-1534 (2010); the Androgen-receptor, Sakamoto, K. M. et al., *"Development of Protacs to target cancer-promoting proteins for ubiquitination and degradation"*. Mol. Cell. Proteomics 2, 1350-8 (2003); methionine aminopeptidease-2, Sakamoto, K. M. et al., *"Protacs: chimeric molecules that target proteins to the Skp1-Cullin-F box complex for ubiquitination and degradation"*, Proc. Natl. Acad. Sci. U.S.A., 98, 8554-9 (2001); as well as the Aryl Hydrocarbon Receptor, Lee, H., Puppala, D., Choi, E. Y., Swanson, H. & Kim, K. B., *"Targeted degradation of the aryl hydrocarbon receptor by the PROTAC approach: A useful chemical genetic tool."*, ChemBioChem 8, 2058-2062, (2007).

To date, all first-generation PROTACs include a peptidic moiety as the E3 ligase ligand. For example, a hydroxyproline-containing heptapeptide sequence ALA-Hyp-YIP from the transcription factor Hypoxia-Inducible Factor 1 alpha subunit (HIF-1α) has been widely used, and as described by Schneekloth, J. S., et al., in *"Chemical Genetic Control of Protein Levels: Selective in Vivo Targeted Degradation."* J. Am. Chem. Soc., 126, 3748-3754 (2004), as this represents the minimal epitope for HIF-1α binding to the E3 ligase von Hippel Lindau protein (VHL), as confirmed by Hon, W.-C. et al., in *"Structural basis for the recognition of hydroxyproline in HIF-1 alpha by pVHL"*, Nature, 417, 975-8 (2002).

The Applicant has recognized that the high peptidic nature of these first-generation PROTACs has resulted in poor physicochemical properties such as low intracellular stability and poor cell permeability, which has limited their applicability as chemical probes as well as their potential utility in therapeutic development.

To overcome these limitations the Applicant has developed novel PROTACs including small molecules of formula I, formula IA, or formula IB for use in the present, non-peptidic PROTAC approach. In a particular aspect this approach exploits novel optimized small molecule drug-like ligands (A) of formula I, IA or IB in PROTAC compounds of structure A-L-B and demonstrates that these can be applied to target BET bromodomains and potently induce effective and selective degradation of BRD4.

According an aspect the present invention provides PROTAC compounds having the structure A-L-B as defined hereinbefore, wherein B is present and wherein B is a ligand which binds to a target protein or polypeptide which is to be degraded by ubiquitin ligase, and wherein said target protein is selected from the group consisting of structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity and translation regulator activity.

According an aspect the present invention provides PROTAC compounds having the structure A-L-B as defined hereinbefore, wherein B is present and wherein B is a ligand which binds to a target protein or polypeptide which is to be degraded by ubiquitin ligase, and wherein said target protein is selected from the group consisting of B7.1 and B7, TI FRIm, TNFR2, NADPH oxidase, BcllBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, GProteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD 124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus, 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, and chloride channels; acetyl-CoA carboxylase, adenylosuccinate synthetase, protoporphyrinogen oxidase, and enolpyruvylshikimate-phosphate synthase.

According an aspect the present invention provides PROTAC compounds having the structure A-L-B as defined hereinbefore, wherein B is present and wherein B is a ligand which binds to a target protein or polypeptide which is to be degraded by ubiquitin ligase, and wherein B is an Hsp90 inhibitor; a kinase inhibitor, a phosphatase inhibitor, an MDM2 inhibitor, a compound which targets human BET Bromodomain-containing proteins, an HDAC inhibitor, a human lysine methyltransferase inhibitor, a compound targeting RAF receptor, a compound targeting FKBP, an angiogenesis inhibitor, an immunosuppressive compound, a compound targeting an aryl hydrocarbon receptor, a compound targeting an androgen receptor, a compound targeting an estrogen receptor, a compound targeting a thyroid hormone receptor, a compound targeting HIV protease, a compound targeting HIV integrase, a compound targeting HCV protease or a compound targeting acyl protein thioesterase 1 and/or 2.

According an aspect the present invention provides a method of degrading a target protein in a patient in need comprising administering to said patient an effective amount of a PROTAC compound of structure A-L-B as defined herein, or use of said PROTAC for degrading a target protein in a patient by administration of an effective amount thereof.

According an aspect the present invention provides a method of targeting protein in a cell comprising exposing said cell to an effective amount of a PROTAC compound of structure A-L-B as defined herein, or use of said PROTAC for targeting protein in a cell comprising exposing said cell to an effective amount thereof.

VHL Binding Ligands and VHL Inhibitors

In addition to their utility as E3 ubiquitin ligase protein binding ligand compounds, it is proposed herein that the novel fluoro hydroxyproline based small molecules of formula IA or IB are inhibitors of the VHL E3 ubiquitin ligase. It is additionally proposed herein that the present VHL inhibitors could find use as molecular therapeutics for the pharmacological stabilization of HIF alpha transcription factors, which could provide therapeutic benefit for many conditions including anemia due to chronic kidney disease and anemia associated to cancer chemotherapy, ischemia and ischemic reperfusion injuries in the kidney, brain, heart or liver, acute lung injuries and intestinal inflammation, as well as stimulation of erythropoiesis in a patient or subject. Compounds according to the present invention also find use as building blocks for the synthesis of the above compounds, standards and controls in bioassays, as intermediates in chemical synthesis and process and related applications, among others.

Thus there is additionally provided herein novel compounds formula IB wherein $R^1$, $R^3$, $R^4$, $R^5$, $R^6$, $R^7$, $R^8$ and Y are as defined hereinbefore, wherein said novel compounds of formula IB are suitable for use as VHL binding ligands and/or VHL inhibitors. Thus the invention also provides VHL ligands and/or VHL inhibitors of formula IB as defined hereinbefore. Exemplary compounds of formula IB, VHL binding ligands and/or VHL inhibitors, are provided in the Experimental section hereinafter.

Highly preferred VHL binding ligands and/or VHL inhibitors of formula IB are compounds 14b, 14d and 14e.

14b

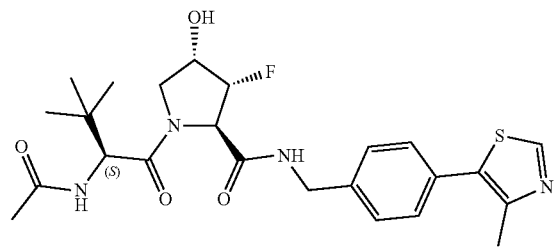

14e

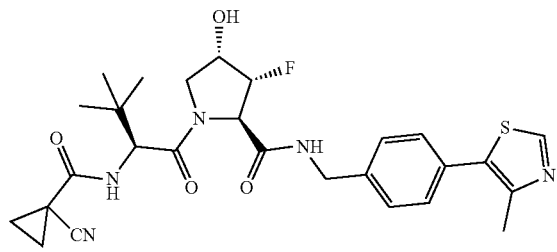

14d

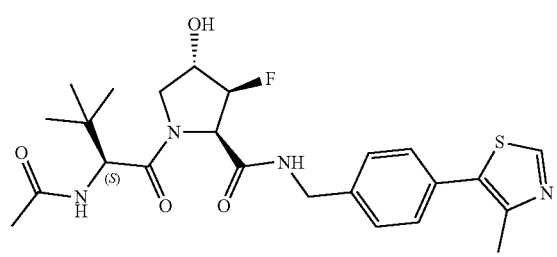

Thus the present invention additionally provides VHL ligands and/or VHL inhibitors independently selected from 14b, 14d and 14e or a pharmaceutically acceptable, salt, enantiomer, stereoisomer, hydrate, solvate, or polymorph thereof.

As detailed hereinbefore compounds of formula IB are useful in the preparation of PROTACs of structure A-L-B. Exemplary PROTACs including compounds of formula IB are provided in the Experimental section hereinafter. Preferred PROTACs herein are PROTACs including 14b, 14d or 14e as an A-group. Highly preferred PROTACs including compounds of formula IB, and in particular 14d as an A-group are Example compounds 18d and 18e as illustrated below and exemplified hereinafter.

18d

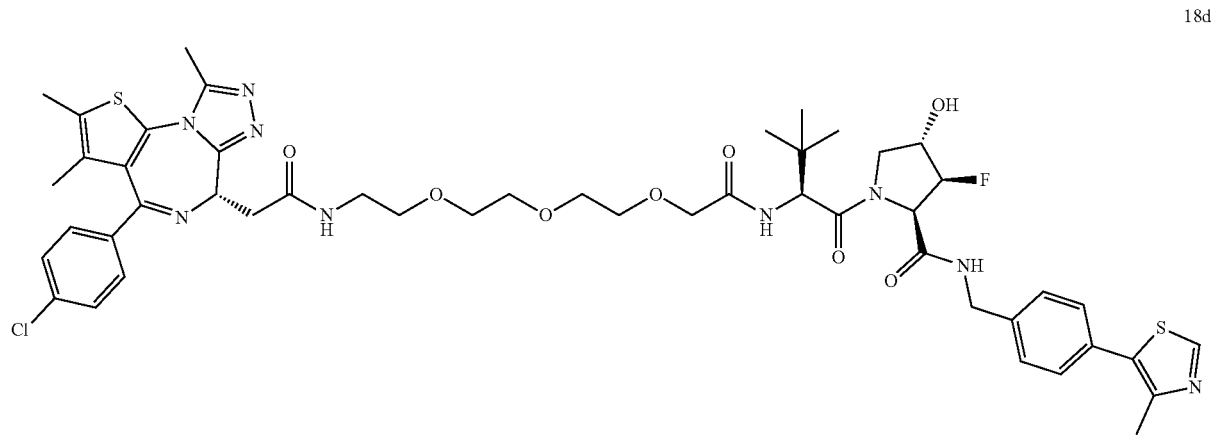

18e

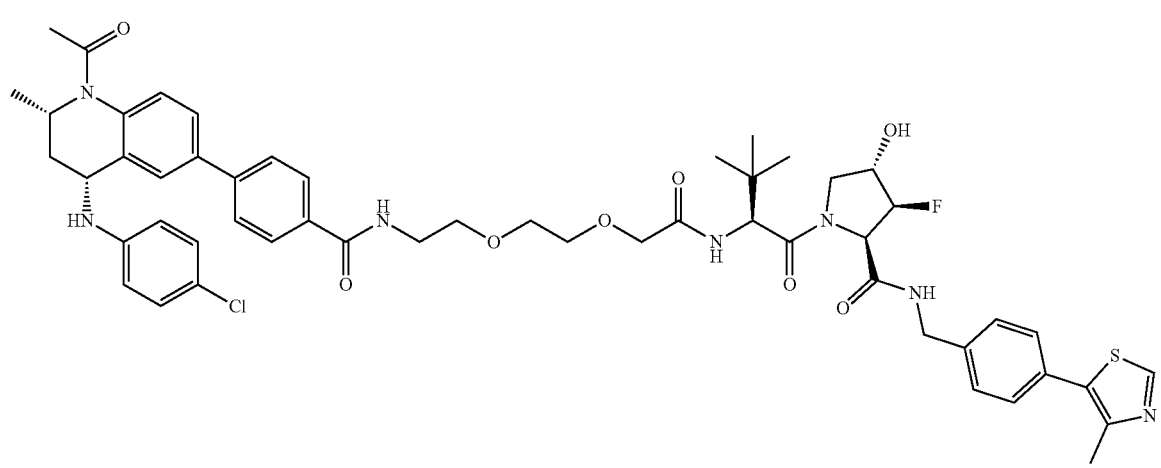

Thus the present invention additionally provides PROTACs independently selected from Example compounds 18d and 18e or a pharmaceutically acceptable, salt, enantiomer, stereoisomer, hydrate, solvate, or polymorph thereof.

Processes for the Preparation of 3-Fluorohydroxyproline (F-HYP)

As indicated hereinbefore the Applicant has developed a novel process for the preparation of 3-fluoro-hydroxyproline intermediate compounds for use in the preparation of compounds of formula A. Compounds of formula A including such a 3-fluoro-hydroxyproline central scaffold are useful for the provision of novel VHL-binding ligand compounds of structure A-L which include a 3-fluoro-hydroxyproline central scaffold. General processes for the provision of both such 3-fluorohydroxyprolines, novel VHL-binders having a central 3-fluoro-hydroxyproline scaffold, as well as PROTACs of structure A-L-B wherein the compound of formula A is based on a 3-fluoro-hydroxyproline central scaffold are detailed hereinafter.

Fluoroprolines are fluorinated amino acids readily available from means of functional group inter-conversion from hydroxyprolines. (2S,4R)-4-Hydroxyproline, or L-hydroxyproline ($C_5H_9O_3N$), chemical name 4-hydroxypyrrolidine-2-carboxylic acid, is a common non-proteinogenic amino acid, and is referred to herein as HYP.

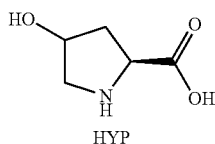
HYP

Inter-conversion/transformation of a hydroxy group on a hydroxyproline for a fluorine is possible using known nucleophilic fluorinating reagents such as for example diethylaminosulfur trifluoride (DAST). As will be appreciated by the skilled chemist, it is not possible to furnish fluorohydroxy prolines from hydroxyprolines using this approach, as in effect F and OH are mutually exclusive. The Applicant has recognized the particular synthetic challenge in the provision of fluoro-hydroxy prolines. In particular the Applicant has appreciated that because of the dense functionalization on the central scaffold, with 3 consecutive stereocenters, any synthesis of fluoro-hydroxy prolines must guarantee a certain degree of both stereo- and regionchemical control, The novel processes developed by the Applicant for the provision of fluoro-hydroxy prolines, and specifically 3-fluorohydroxyprolines (F-HYP) are discussed hereinafter in relation to Schemes 1 and 2.

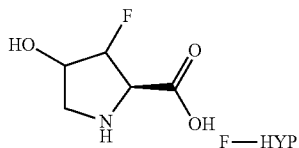
F—HYP

As illustrated in Scheme 1, the present process for the provision of fluoro-hydroxy prolines firstly utilized an electrophilic fluorination strategy from a ketone intermediate readily available by oxidation of hydroxyproline, with subsequent stereo-selective reduction of the resulting α-fluoroketone intermediate in a second step. By selection of the opportune protecting group on the proline nitrogen, of hydroxyproline, the Applicant has provided a complete stereo-specific fluorination of hydroxyproline.

In particular, Scheme 1 illustrates the novel process for preparation of specified 3-fluoro-4-hydroxyprolines (5a), (5b), (5c) and (5d) from starting compound (1), and additionally illustrates how each of these compounds can be prepared from a corresponding N-Boc intermediate compound (3a), (3b), (3c) and (3d) in a single step, stage v of Scheme 1.

Scheme 1

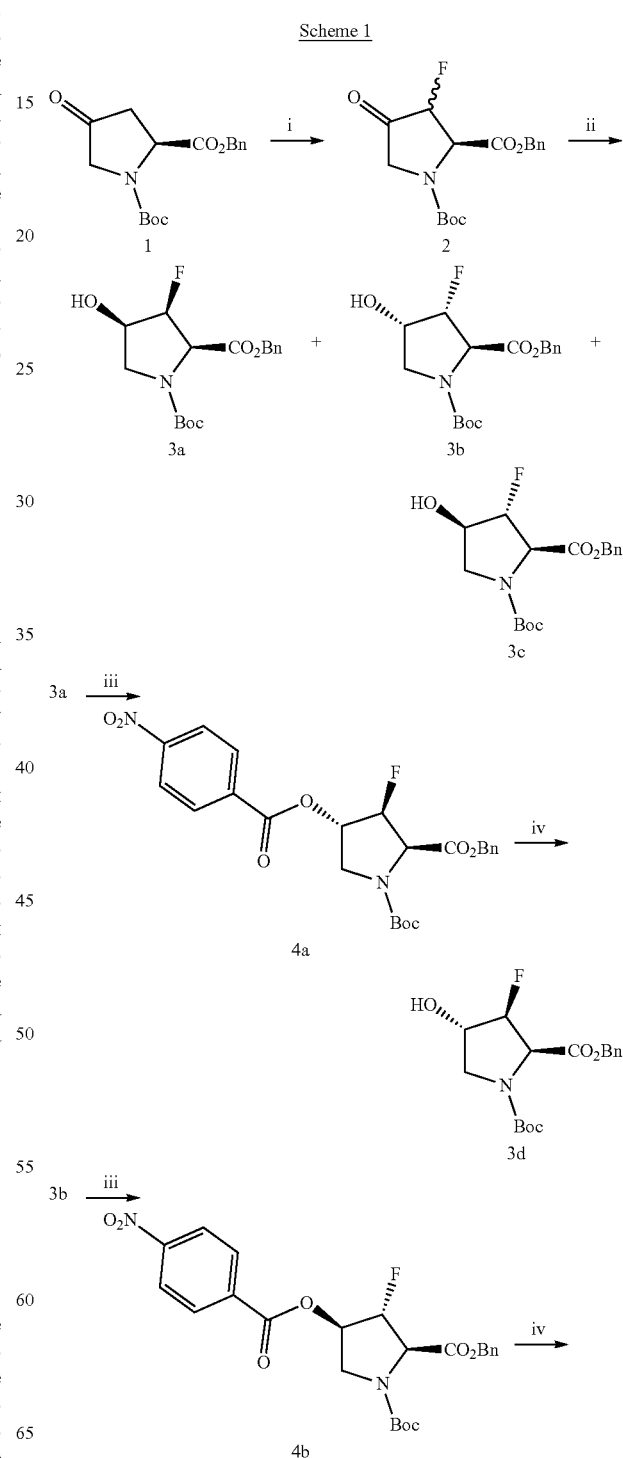

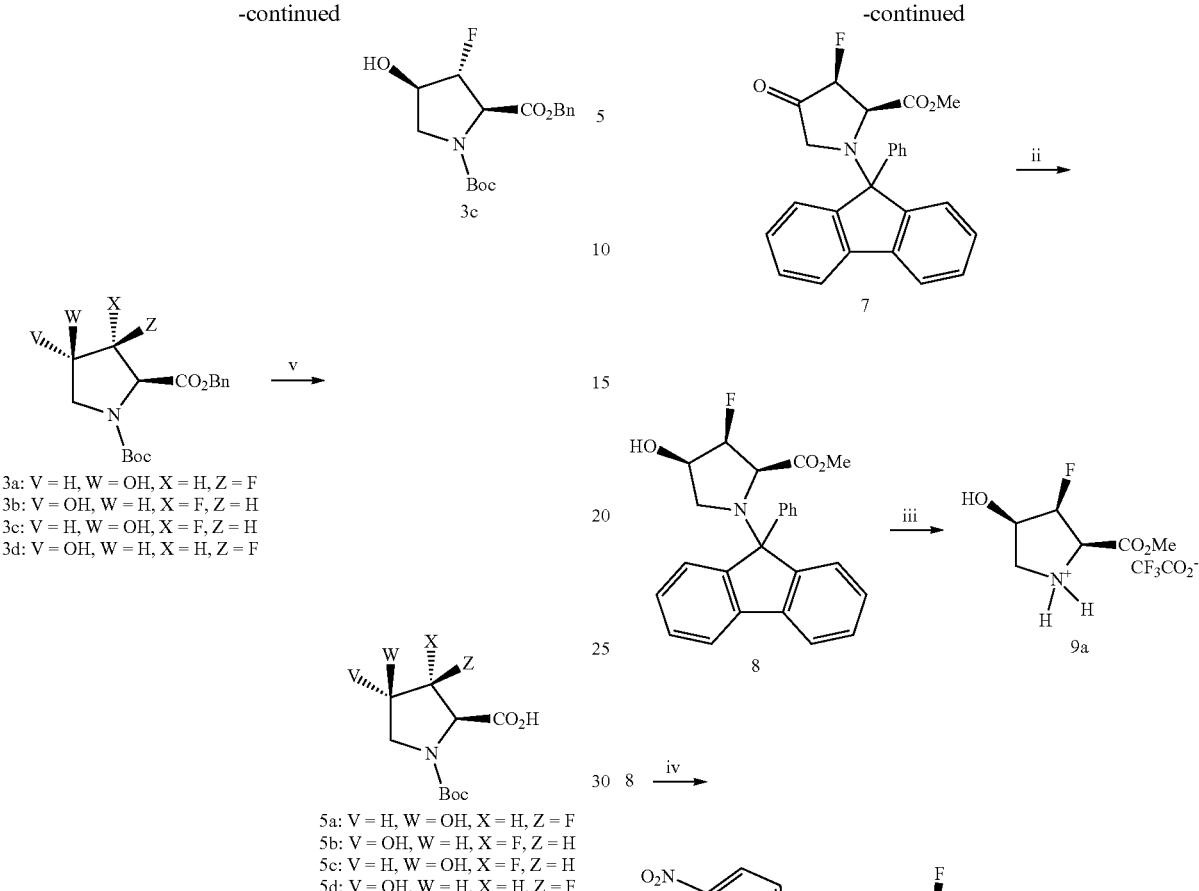

3a: V = H, W = OH, X = H, Z = F
3b: V = OH, W = H, X = F, Z = H
3c: V = H, W = OH, X = F, Z = H
3d: V = OH, W = H, X = H, Z = F

5a: V = H, W = OH, X = H, Z = F
5b: V = OH, W = H, X = F, Z = H
5c: V = H, W = OH, X = F, Z = H
5d: V = OH, W = H, X = H, Z = F

Scheme 1, reagents and conditions: (i) lithiumhexamethyldisilazide (LiHMDS), TMSCl, in THF, -78° C. to r.t. then Selectfluor ™ (1-chloromethyl-4-fluoro-1,4-diazoniabicyclo[2.2.2]octane bis(tetrafluoroborate)) in ACN; (ii) NaBH$_4$ in THF/EtOH, 0° C., column chromatography separation; (iii) DIAD, PPh$_3$, 4-nitrobenzoic acid in THF, 0° C., to r.t.; (iv) NaN$_3$ in methanol 50° C.; (v) H$_2$, Pd/C in THF/MeOH r.t.

As illustrated in Scheme 1 this novel synthetic approach has enabled the Applicant to preparation all 4 diastereoisomeric 3-fluoro derivatives of 4-hydroxyproline, (5a), (5b), (5c), and (5d). Illustrated in Scheme 2 is an approach wherein selection of the opportune protecting group on the proline nitrogen (9-phenylfluorenyl) the fluorination reaction becomes stereoselective to furnish only F "up". This stereoselective approach allows the synthesis of compounds 5a and 5d.

Scheme 2

9a: V = H, W = OH
9b: V = OH, W = H

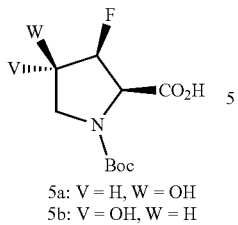

5a: V = H, W = OH
5b: V = OH, W = H

Scheme 2, reagents and conditions: i) TMSOTf, TEA, DCM, -20° C., 3 h; then Selectfluor ™ (1-chloromethyl-4-fluoro-1,4-diazoniabicyclo[2.2.2]octane bis(tetrafluoroborate)) in ACN, -30° C.; ii) NaBH$_4$, EtOH/THF 0° C.; iii) TFA 5% in DCM, TIPS; iv) DIAD, PPh$_3$, 4-nitrobenzoic acid, THF, 0 to 40° C.; v) NaOH, THF/H$_2$O, r.t; vi) LiOH, H$_2$O, 0° C.; vii) BOC$_2$O, NaHCO$_3$, H$_2$O, r.T.

The present invention provides novel processes for the provision of F-HYP, protected forms of F-HYP, and intermediates useful in the preparation of F-HYP as illustrated in Schemes 1 and 2 herein According to a further aspect there is provided herein compounds of general formula II:

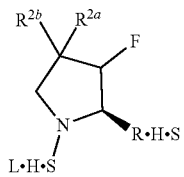

II wherein $R^{2a}$ is OH, —CHF$_2$, —CF$_3$, NH$_2$ or F, wherein $R^{2b}$ is H, $^2$H, $^3$H, a —(C$_1$-C$_3$) alkyl group, an aryl group, a heteroaryl group, —CF$_3$, —CF$_2$H, a —CF$_2$—(C$_1$-C$_2$) alkyl group, or F, wherein LHS is: H; an amine protecting group selected from: a 9-phenyl-9-fluorenyl, a fluoroenylmethyloxycarbonyl protecting group (Fmoc group), a tert-butyloxycarbonyl protecting group (BOC group), or an acetamide group; or a suitable alternative amine protecting group for the ring-N, wherein RHS is —CO$_2$H, —CO$_2$CH$_3$ or —CO$_2$D where D is a suitable carboxylic acid protecting group such as for example an alternative alkyl ester or a benzyl ester.

There is also provided herein compounds of general formula II as defined hereinbefore wherein LHS is H, 9-phenyl-9-fluorenyl group, a fluoroenylmethyloxycarbonyl protecting group, an acetamide group, or a tert-butyloxycarbonyl protecting group (BOC group, and/or wherein RHS is —CO$_2$H, —CO$_2$CH$_3$ or —CO$_2$Bn.

There is also provided herein compounds of general formula II as defined hereinbefore wherein $R^{2a}$ is OH, $R^{2b}$ is H, LHS is a BOC group and RHS is a —CO$_2$Bn group having the structural formulae II-A, II-B, II-C and/or II-D:

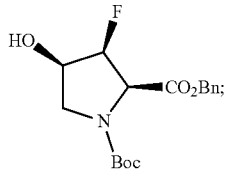

II-A

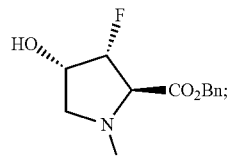

II-B

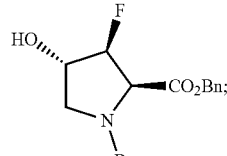

II-C

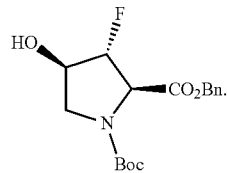

II-D

There is also provided herein compounds of general formula II as defined hereinbefore wherein $R^{2a}$ is OH, $R^{2b}$ is H, LHS is a BOC group and RHS is a —CO$_2$H group having the structural formulae II-E, II-F, II-G and/or II-H:

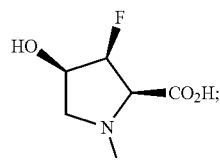

II-E

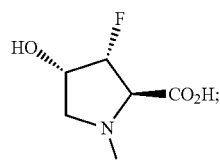

II-F

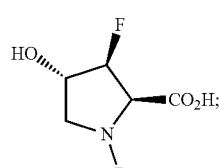

II-G

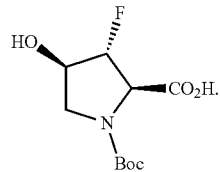

II-H

There is also provided herein compounds of general formula II as defined hereinbefore wherein $R^{2a}$ is OH, $R^{2b}$ is H, wherein LHS is an acetamide group and RHS is a —CO$_2$H group having the structural formulae II-I, II-J, II-K and/or II-L:

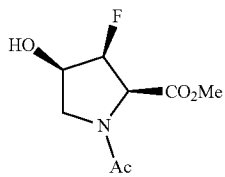

II-I

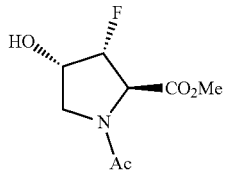

II-J

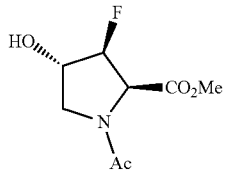

II-J

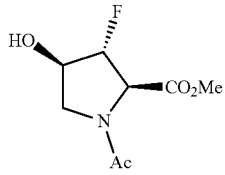

II-K

There is also provided herein compounds of general formula II as defined hereinbefore wherein wherein $R^{2a}$ is OH, $R^{2b}$ is H, LHS is a 9-phenyl-9-fluorenyl group and RHS is —$CO_2H$, —$CO_2CH_3$ or —$CO_2D$ having the structural formulae II-L, II-M, II-N and/or II-O, and preferably wherein LHS is a 9-phenyl-9-fluorenyl group and RHS is —$CO_2CH_3$ having the structural formulae II-P, II-Q, II-R and II-S:

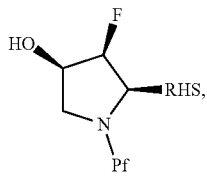

II-L

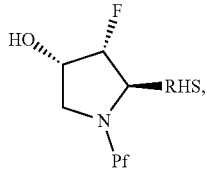

II-M

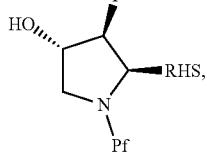

II-N

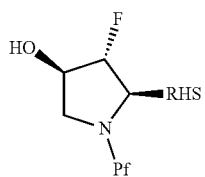

II-O

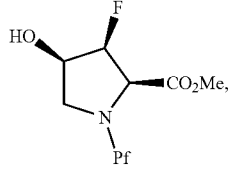

II-P

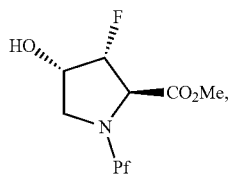

II-Q

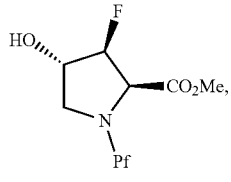

II-R

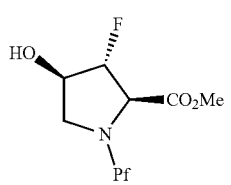

II-S

There is also provided herein compounds of general formula II as defined hereinbefore wherein R2a is OH, R2b is H, LHS is a Fmoc group and RHS is a —CO2H group having the structural formulae 5e and 5f:

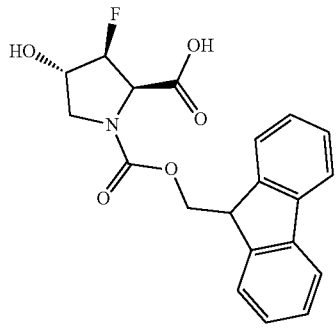

5e

-continued

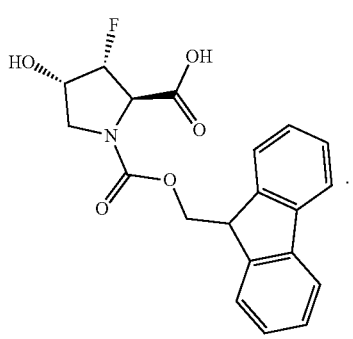

5f

According to a further aspect there is provided herein a process for the preparation of compounds of general formula II as defined hereinbefore from intermediate compounds of general formula III, wherein the LHS is H; an amine protecting group selected from: a 9-phenyl-9-fluorenyl, a Fmoc group, a BOC group (as illustrated below), or an acetamide group; or a suitable alternative amine protecting group for the ring-N:

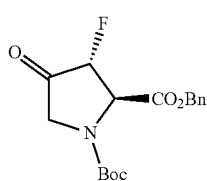

III and wherein said compounds of general formula III are converted to compounds of general formula II via treatment with a suitable reducing agent, and preferably via treatment with NaBH$_4$.

There is particularly provided herein a process for the preparation of intermediate compounds of structural formulae II-A II-B, II-C and II-D from intermediate compounds of structural formulae III-A or III-B:

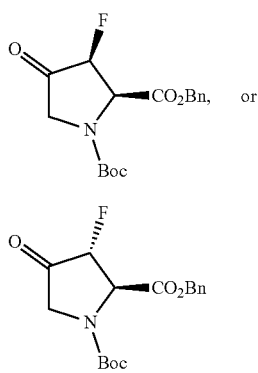

III-A

III-B wherein said intermediate compounds of structural formulae III-A or III-B are converted into structural formulae II-A, II-B, II-C and II-D by treatment with a suitable reducing agent, and preferably via treatment with NaBH$_4$. There is also provided herein a process wherein the corresponding intermediate compounds where the LHS (BOC) group in III-A, or III-B are replaced by a 9-phenyl-9-fluorenyl group, a Fmoc group or an acetyl group, and where the RHS is —CO$_2$H, —CO$_2$CH$_3$, —CO$_2$Bn or —CO$_2$D are utilized to prepare a range of compounds of structural formulae II, including the compounds having structural formulae II-E, II-F, II-G, II-H, II-I, II-J, II-L, II-M, II-N, II-O, II-P, II-Q, II-R and/or II-S.

According to an additional aspect there is provided herein a process for the preparation of intermediate compounds of general formula III, via conversion of starting compounds of formula V having the appropriate LHS and RHS to intermediate compounds of general formula IV with subsequent transformation into compounds of general formula III having the same LHS and RHS functionalities as the starting compound:

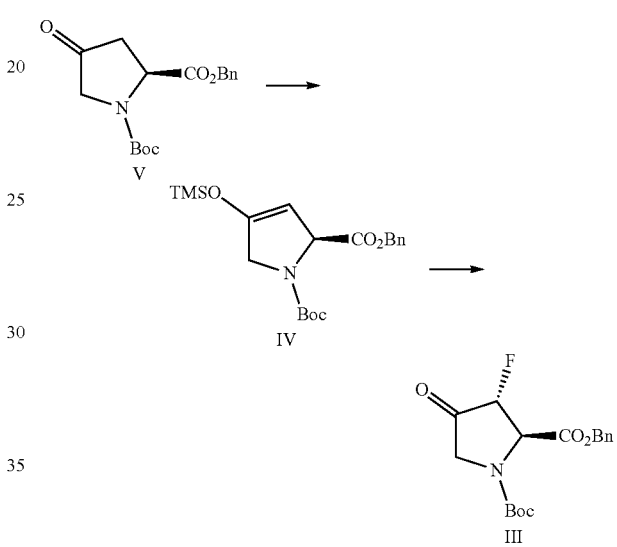

wherein said starting compounds of general formula V are converted to compounds of general formula IV via a 2-step approach wherein the carbonyl group is protected using a suitable protection strategy, such as an TMSO— group followed by fluorination of the protected intermediate compound IV to provide the desired 3-fluoro-compounds. In each of the particular compounds of general formulae V, IV and III illustrated, LHS is BOC and RHS is —CO$_2$Bn. Starting from the appropriate compound of general formula V where the LHS is a 9-phenyl-9-fluorenyl group, a Fmoc group, an acetyl group or a BOC group, and where the RHS is —CO$_2$H, —CO$_2$CH$_3$, —CO$_2$Bn or —CO$_2$D a range of intermediate compounds of structural formulae IV and III can be prepared. In particular a range of further intermediate compounds of formulae III-E, III-F, III-G, III-H, III-I, III-J, III-L, III-M, III-N, III-O, III-P, III-Q, III-R and/or III-S I, in which the LHS and RHS groups correspond to those in the intermediate compounds having structural formulae II-E, II-F, II-G, II-H, II-I, II-J, II-L, II-M, II-N, II-O, II-P, II-Q, II-R and/or II-S.

There is additionally provided a process for the preparation of intermediate compounds of structural formula III-A and III-B, via conversion of compound of structural formula V to an intermediate compound of structural formula IV with subsequent transformation into compounds of formulae III-A and III-B:

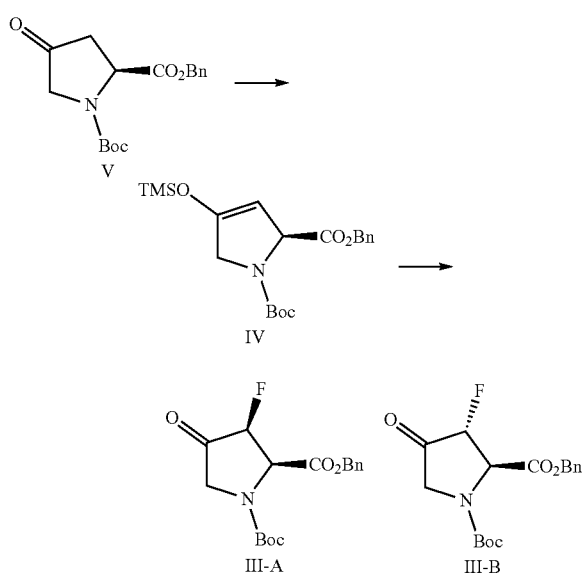

wherein compound formula V is converted to compounds III-A and III-B via a 2-step approach wherein the carbonyl group is protected using a suitable protection strategy, such as an TMSO— group followed by fluorination of the protected intermediate compound IV to provide the desired 3-fluoro-compounds of formulae III-A and III-B.

There is particularly provided herein a process for the stereo-selective synthesis of F-HYP, and the stereo-selective synthesis of N-protected derivatives of F-HYP suitable for use in the preparation of the novel VHL-binders/and or VHL inhibitors, or PROTACs of structure A-L-B, wherein said process is accordance with the methodology of Scheme 2. There is especially provided herein a process for the stereo-selective synthesis of F-HYP starting from preparatory compound 6, an intermediate of general formula V, and conversion to the corresponding fluorinated intermediate of general formula III, preparatory compound 7, followed by reduction to furnish a 3-fluoro-4-hydroxy intermediate of general formula II, preparatory compound 8. The intermediate quaternary amines 9a and 9b are individually and separately synthesized from this one 3-fluoro-4-hydroxy intermediate of general formula II, whereby 9a is provided by direct transformation (from 8) in accordance with stage iii of Scheme 2, and wherein 9b is provided in a 3-step approach (from 8) via stage iv (to furnish 10), stage v (to furnish 11) and stage iii to furnish 9b of Scheme 2. Compounds 9a and 9b are then transformed into protected intermediate compounds of formula II, compounds 5a (II-A) and 5d (II-C) respectively via a 2-step approach in accordance with Scheme 2, stages vi and vii. These N-protected derivatives can be readily de-protected via any suitable de-protection approach, such as those detailed herein to furnish the corresponding pair of stereo-specific F-HYPs.

For the avoidance of doubt whilst the process specifically illustrated in Scheme 2 is directed to the provision of a pair of stereo-specific N-protected derivatives of F-HYP, alternative N-protected derivatives can be readily prepared in accordance with the methodologies detailed herein. As will be appreciated, the same pair of stereo-specific F-HYPs are prepared via utility of alternative protecting group strategies (to BOC) in stages vi, and vii of Scheme 2.

General Processes for the Preparation of PROTACs

Processes for the preparation of exemplary PROTACs of structure A-L-B are provided in detail in the Chemistry— Materials and Methods section hereinafter. As illustrated in general Scheme B a general methodology for the preparation of any PROTAC of structure A-L-B as defined herein is to firstly prepare an E3 binding ligand of formula I, IA or IB, compound A in general Scheme A, and then to couple this to a selected linker (L). This furnishes an intermediate azide compound of general formula Az-L-A, having the structure A-L-$N_3$ as illustrated in general Schemes A and B as compound C, and as particularly illustrated in Scheme 4 hereinafter for the preparation of Az-L-A preparative compounds 16a-16e. These azide intermediate compounds C of general formula Az-L-A can then be subsequently coupled to the desired protein target binding ligand (B) via any suitable coupling reaction, such as for example via reductive amination as illustrated in general Scheme A, and as particularly illustrated in Scheme 5 hereinafter to provide PROTACs, such as for example compounds 18a-e.

As will be appreciated by the skilled chemist, via use of the linker coupling methodology as outlined in Scheme A, and the general methodologies for the preparation of compounds of formula I and azide-linker groups, as provided in Schemes 4 and 6 in the Examples section herein, any compound of formula I, IA or IB, as detailed herein may be linked together with any suitable linker group L to provide an intermediate azide of structure Az-L-A. The invention additionally provides intermediate azide compounds of structure Az-L-A, wherein L and A are as detailed hereinbefore, and in particular wherein L and A are as detailed in relation to compounds of formula IB as defined herein.

General Scheme A

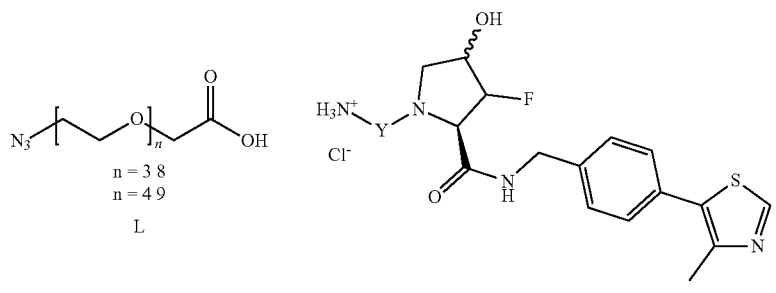

HATU, HOAT, DIPEA
2 h, 25° C.
DMF

-continued

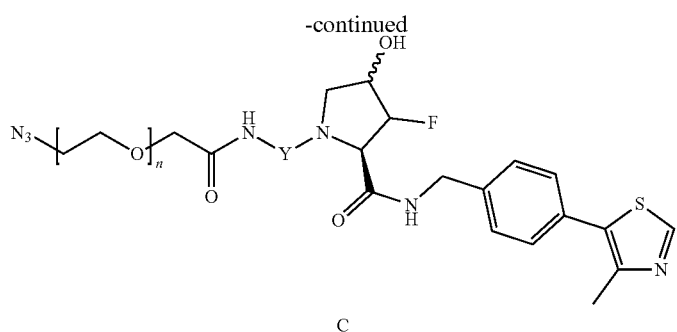

C

Y =

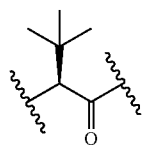

i

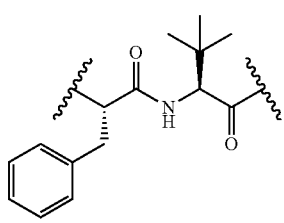

ii

Whilst Scheme 5 hereinafter provides a route for formation of certain exemplary PROTAC compounds, as detailed in the Examples section hereinafter, from the corresponding azides of structure Az-L-A, as will be appreciated by the skilled chemist, via use of the methodology outlined in general Scheme A, and the reagents and conditions indicated in Scheme 5, any intermediate azide compound of structure Az-L-A as detailed herein may be linked together with any protein target binding ligand B via coupling of the linker group L with B to provide a PROTAC of structure A-L-B as defined herein.

As discussed hereinbefore general Scheme A provides a general process for formation of the intermediate azide compounds C having structure Az-L-A, from the corresponding de-protected amines A and linker compounds L. General processes for the preparation of compounds A, of Formula I, or Formula IA or Formula IB, suitable for linking to L at the $R^1$, $R^3$, $R^4$, $R^5$ or $R^8$ positions to provide PROTACs of structure A-L-B are detailed herein in example Scheme 3, with a process for the preparation of intermediates of structure Az-L-A also being illustrated in example Scheme 4 and the general process for subsequent coupling of intermediate azides C with the desired protein target binding ligand B to provide PROTACs of structure A-L-B being illustrated in general Scheme A, and in example Scheme 5.

General Scheme B

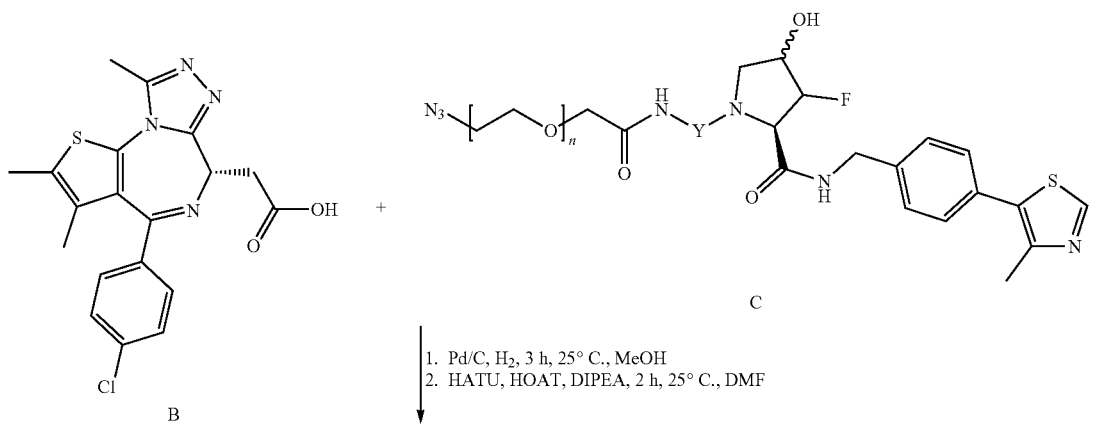

1. Pd/C, H$_2$, 3 h, 25° C., MeOH
2. HATU, HOAT, DIPEA, 2 h, 25° C., DMF

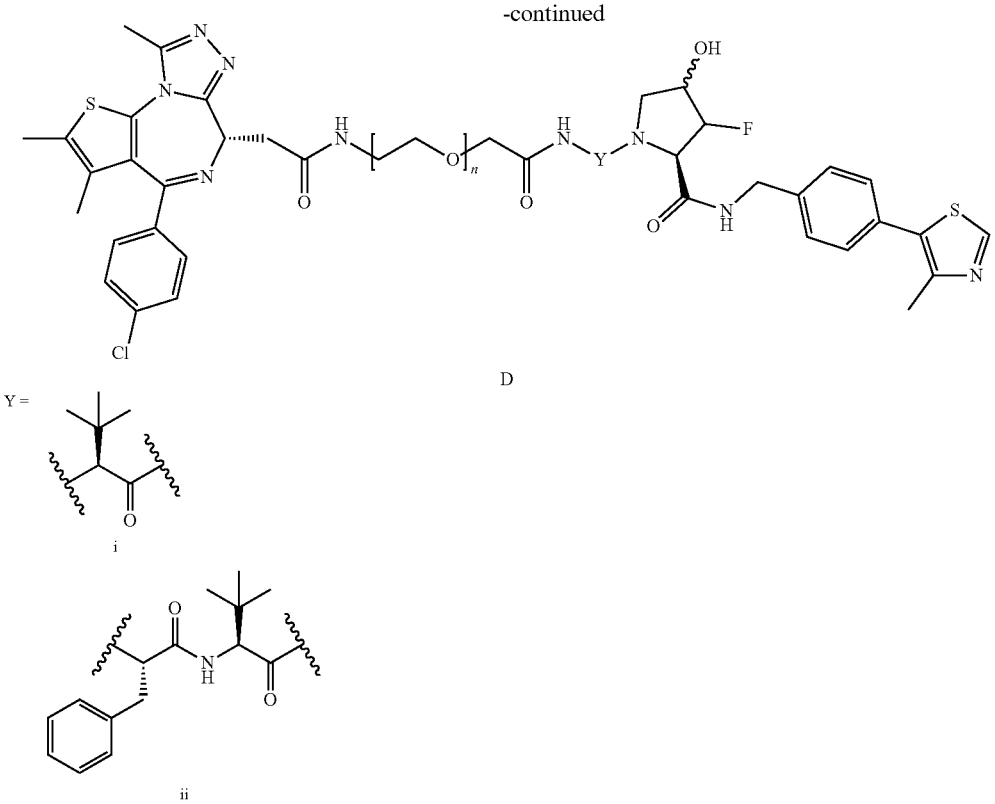

D

As will be readily appreciated by the skilled chemist, suitable protection/de-protection strategies may be employed to protect vulnerable functional groups on the compounds of formulae I, IA, or IB, or any of the other compounds or structure illustrated in general Schemes A, B, and/or example Schemes 1 to 5 herein, such as for example during one or more of the coupling steps.

General Processes for Preparation of the Present PROTACs

The Applicant has developed a group of PROTACs that have been demonstrated to link together specific VHL ligands and BET bromodomains ligands. Initial work by the Applicant has established that known compounds VHL-1 and VHL-2 are strong binders with $K_d$ values below 300 nM to VHL (FIG. 1a), in Galdeano, C. et al., "*Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities*", J. Med. Chem. 57, 8657-63 (2014). Inspection of the protein-ligand crystal structures have shown that the methyl group of the terminal acetyl groups in compounds VHL-1 and VHL-2 is solvent exposed and this was selected as a suitable connecting point for a linker (L). This is illustrated in FIG. 4. To confirm that the PROTAC approach provided in the present invention do bind to a target protein, the BET inhibitor JQ1 was chosen as a bromodomain-recruiting scaffold (B) and its t-butyl ester group was selected as a potential connecting point for a linker (L) because it is solvent-exposed and not involved in key interaction with the BET bromodomains, as shown by the co-crystal structures as illustrated in FIG. 4 and as discussed herein.

Linkers (L) with different lengths comprising of polyethylene glycol chains with either 3 or 4 ethylene glycol units were chosen to connect JQ1 with the VHL ligand in initial proof-of-concept experiments.

To achieve the desired ligands, a generally applicable two-step synthetic strategy was devised. First, the linker bearing a carboxylic acid at one end and an azide group at the other end was connected with the terminal free amine of the VHL ligand by an HATU-mediated amide bond formation. In the second step, reduction of the azide group to an amine and subsequent amide bond formation with the carboxylic acid of the ester-hydrolyzed JQ1 analogue afforded the desired PROTAC compounds of Examples 18d and 18e hereinafter.

General Scheme C

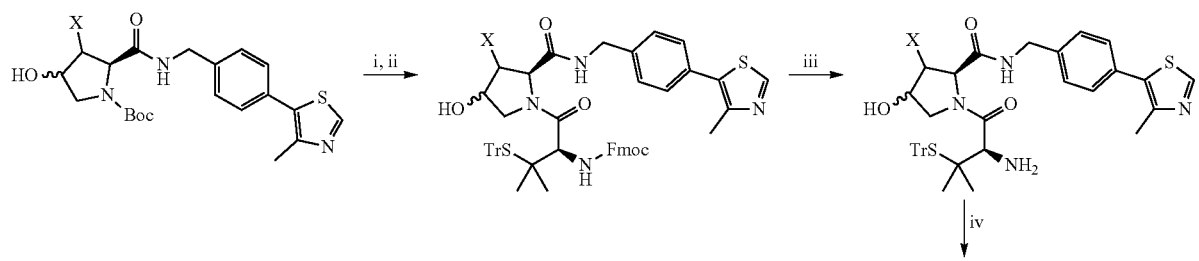

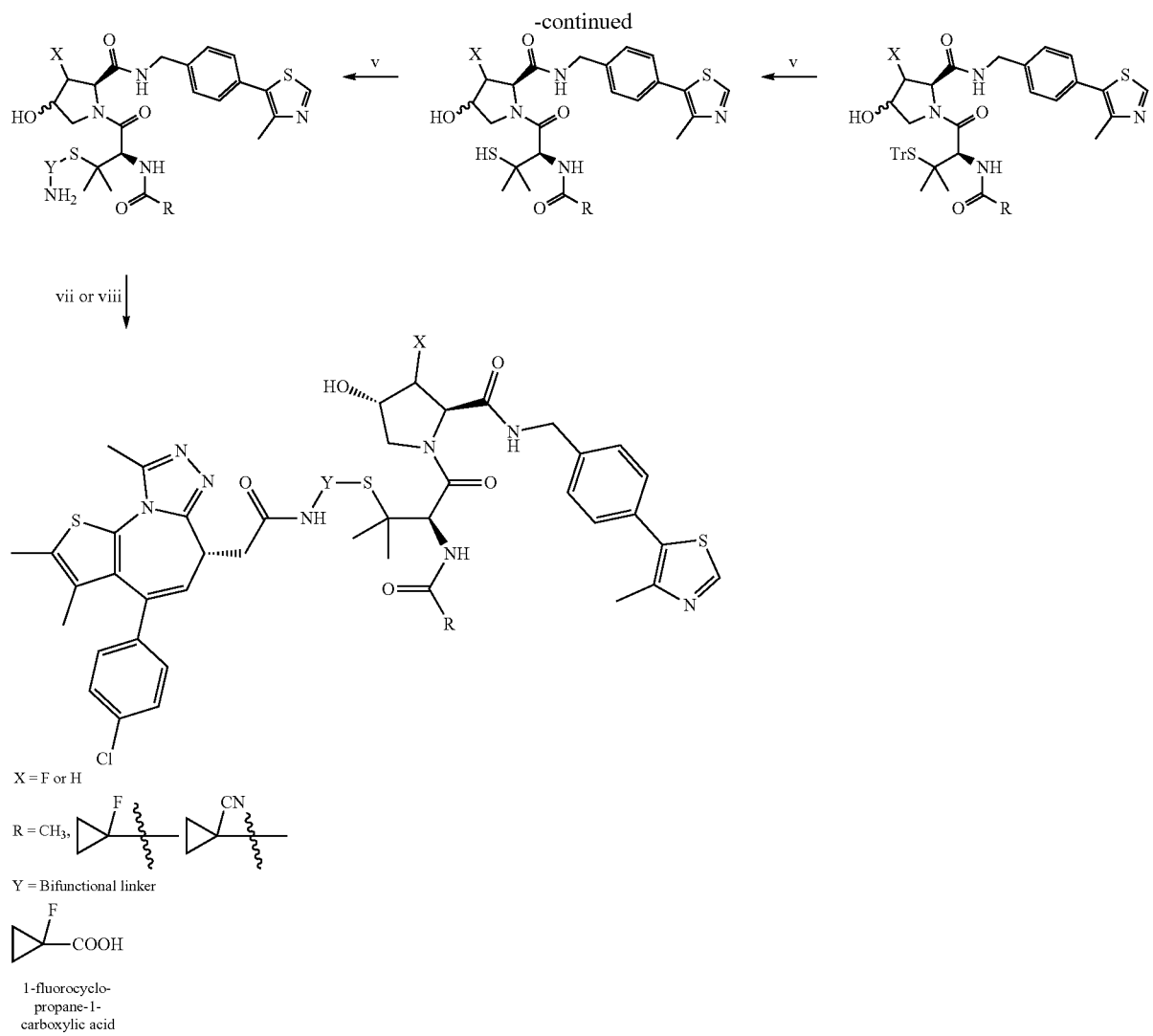

General Scheme C provides a general process for the PROTACS of structure A-L-B with compounds A that follow formula IB with linkage to L at the $R^8$ position and R8 being -S-$R^{8*}$.

Reagents and conditions: i) HCl 2M in dioxane/DCM 1:1, r.t., 99%; Fmoc-S-trityl-L-penicillamine, HATU, HOAT, DIPEA in DMF, r.t.; iii) Piperidine 20% in DCM, r.t., 75% over two steps; iv) acetic anhydride, triethylamine in DCM 0° C. to r.t., 98%; v) TFA- TIPS 5% in DCM, r.t., 79%; vi) Linker-OMs or Linker-OTs or Linker-Br , DBU, in DMF 0° C. to r.t., 70-82%; vii) if X = N₃: H₂ (balloon), Pd/C 10%, in MeOH, 99%; viii) if X = NPhtal: Hydrazine hydrate in ethanol, 70° C., 60-68%; (+)-JQ1-COOH, HATU, HOAT, DIPEA in DMF, r.t. 33-70%.

Experimental Data for Binding of PROTAC Molecules to Target Proteins

As reported by the Applicant, Galdeano et al., J. Med. Chem. 2014, 57, 8657-8663 and Zengerle, M., Chan, K.-H., Ciulli, A. Selective Small Molecules Induced Degradation of the BET Bromodomain Protein BRD4. ACS Chem. Biol. 2015, 10(8), 1770-1777, the stereochemistry of the-hydroxyl group of the central hydroxyproline moiety is crucial for ligand binding to VHL. Whereas compound MZ1 was found to bind VHL, a compound that is structurally identical to the MZ1 except for a reversed stereo center at the C-4 position bearing the hydroxyl group (cisMZ1) did not exhibit any measureable binding affinity for VHL, nor target protein degradation activity. Applicant proposes that binding of compound 18d as described hereinafter will be similarly affected by hydroxyl group stereochemistry. The structures of both MZ1 and cisMZ1 are illustrated in FIG. 7 and both compounds can be prepared using the methodology described in unpublished international patent application PCT/GB2016/050691 and degradation of the BET Bromodomain protein BRD4 by MZ1 is discussed in Zengerle et. al.

Thus the present invention provides a group of PROTAC compounds of structure A-L-B wherein A is a compound of formula IA as defined hereinbefore, wherein X is N, and $R^{2a}$ (the central R-group at the C-4 position) is a hydroxyl group having trans-stereochemistry.

The present invention provides a PROTAC compound of structure A-L-B wherein A is a compound of formula IA, wherein X is N, and $R^{2a}$ (the central R-group at the C-4 position) is a hydroxyl group having trans stereochemistry and wherein said PROTAC compound is independently selected from:

Example Compound 18d: 2R,3S,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16- dioxo-6,9,12-trioxa-3,15-diazaheptadecanoyl)-3-fluoro-4-hydroxy-N-(4-(4-methylthiazol-5-yl)benzyl)pyrrolidine-2-carboxamide;

Example Compound 18e: (2R,3S,4S)-1-((S)-1-(4-((2S,4R)-1-acetyl-4-(4-chlorobenzyl)-2-methyl-1,2,3,4-tetrahydroquinolin-6-yl)phenyl)-12-(tert-butyl)-1,10-dioxo-5,8-dioxa-2,11-diazatridecan-13-oyl)-3-fluoro-4-hydroxy-N-(4-(4-methylthiazol-5-yl)benzyl)pyrrolidine-2-carboxamide;

or a pharmaceutically acceptable salt, enantiomer, stereoisomer, hydrate, solvate, or polymorph thereof.

As discussed hereinbefore there is provided PROTAC compounds having the structure A-L-B wherein A is an E3 ubiquitin ligase protein binding ligand compound of formula I, preferably of formula IA, wherein L and B are in accordance with any of the aspects as detailed hereinbefore, and wherein the L-group is directly bonded to the compound of Formula I or IA at the $R^1$, $R^3$, $R^4$, $R^5$ or $R^8$ positions. Exemplary compounds wherein the L-group is directly bonded to the compound of Formula I or IA at the $R^1$, $R^3$, $R^4$, $R^5$ or $R^8$ positions are provided in Groups I to V hereinafter.

The present invention additionally provides a PROTAC compound of structure A-L-B wherein A is a compound of formula IA independently selected from the compounds identified in any of Groups I to V, as shown in Tables I to V, and wherein L and B are as defined in accordance with any of the aspects hereinbefore.

Group I. Compounds of Formula I with Linkage to L at the $R^1$ Position.

TABLE I

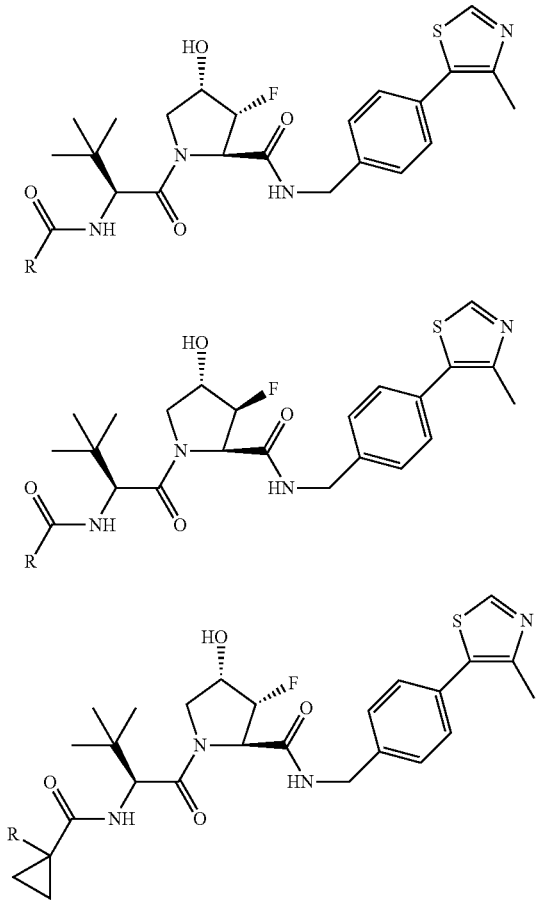

TABLE I-continued

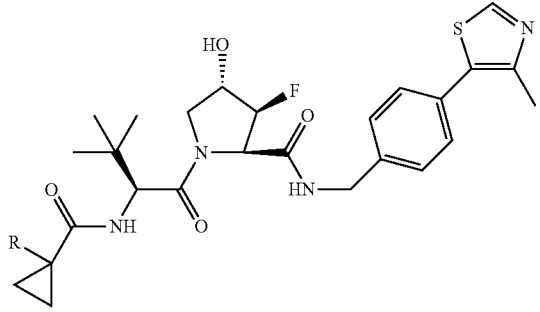

Thus there is also provided herein a Group I of compounds for Formula IA, wherein X=N, Y=C(O)C(CH$_3$)$_3$, wherein $R^x$ and $R^{2b}$, $R^3$, and $R^4$ are all H, wherein $R^{2a}$ is OH, wherein $R^5$ is CH$_3$, wherein L is as defined previously herein and is preferably A6 or A7, and wherein $R^1$ is a covalent bond to L or a cyclopropyl group with a covalent bond to L.

Group II. Compounds of Formula I with Linkage to L at the $R^3$ Position.

TABLE II

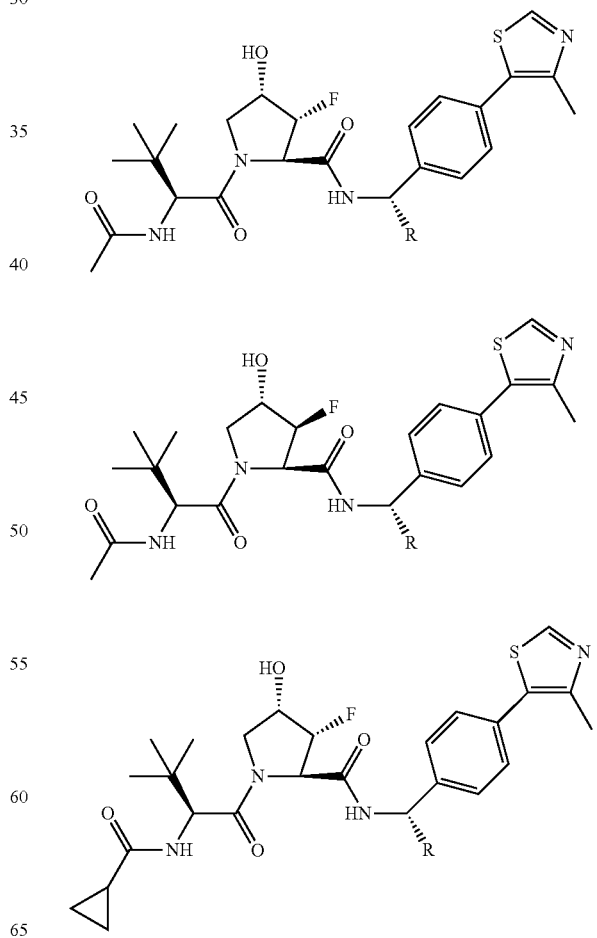

TABLE II-continued

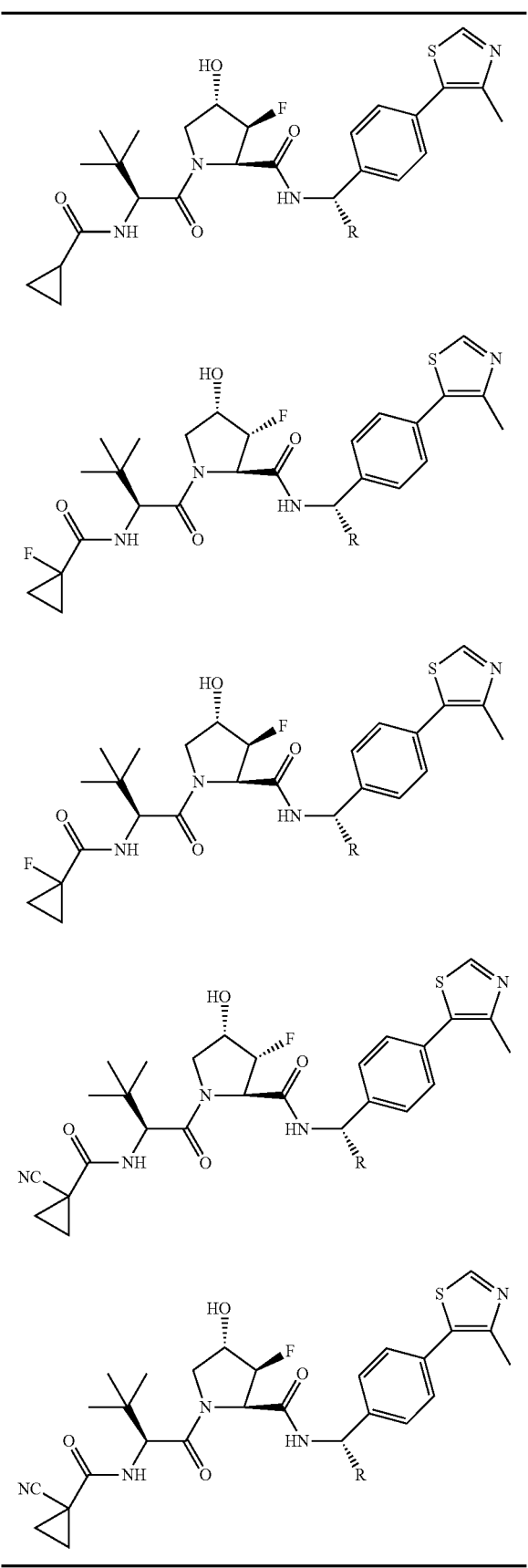

Thus there is also provided herein a Group II of compound for Formula IA, wherein X=N, Y=C(O)C(CH$_3$)$_3$, wherein R$^x$ and R$^{2b}$, and R$^4$ are all H, wherein R$^{2a}$ is OH, wherein R$^5$ is CH$_3$, wherein L is as defined previously herein and is preferably A6 or A7, wherein R$^1$ is CH$_3$, a cyclopropyl group, a 1-fluorocyclopropyl group, or a 1-cyanocyclopropyl group, and wherein R$^3$ is a covalent bond to L.

Group III. Compounds of Formula I with Linkage to L at the R$^4$ Position.

TABLE III

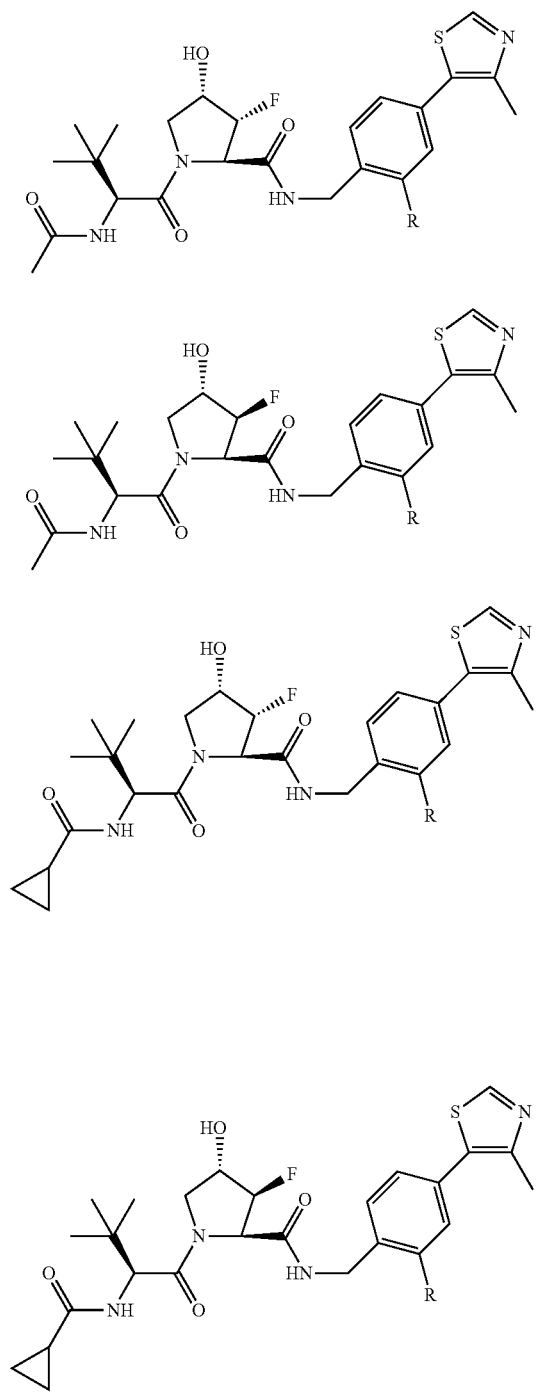

TABLE III-continued

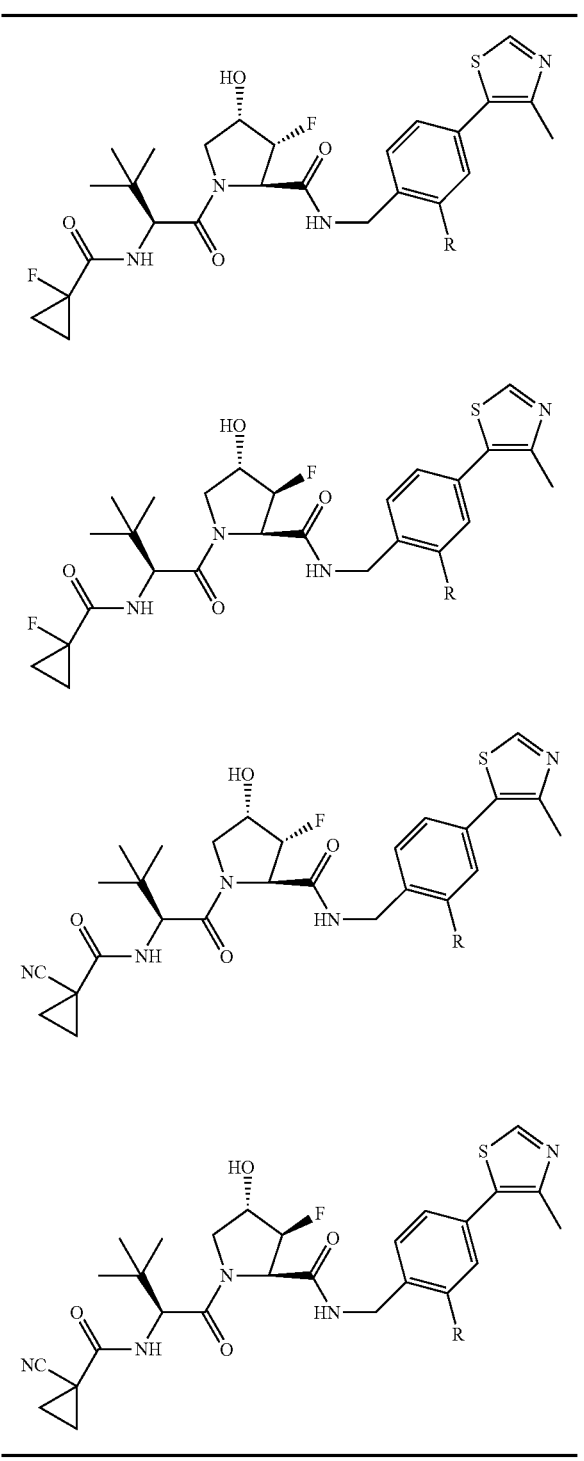

Thus there is also provided herein a Group III of compounds for Formula IA, wherein X=N, Y=C(O)C(CH$_3$)$_3$, wherein R$^x$ and R$^{2b}$, and R$^3$ are all H, wherein R$^{2a}$ is OH, wherein R$^5$ is CH$_3$, wherein L is as defined previously herein and is preferably A6 or A7, wherein R$^1$ is CH$_3$, a cyclopropyl group, a 1-fluorocyclopropyl group, or a 1-cyanocyclopropyl group, and wherein R$^4$ is a covalent bond to L.

Group IV. Compounds of Formula I with Linkage to L at the R$^5$ Position.

TABLE IV

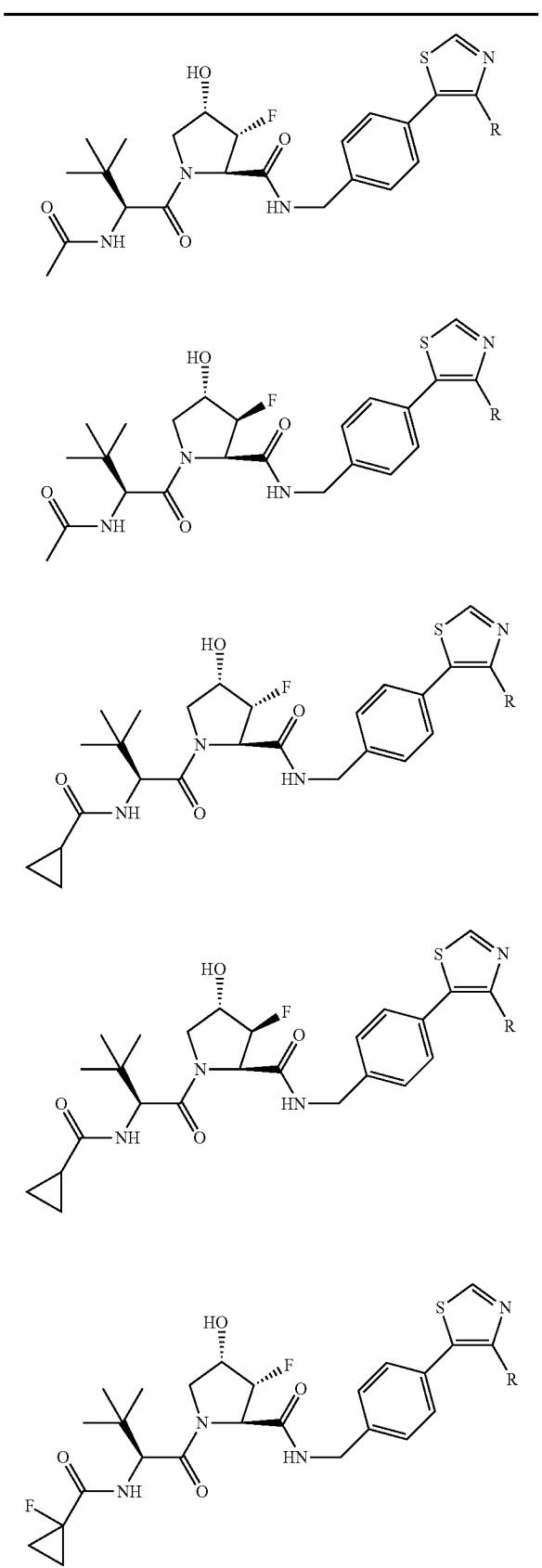

TABLE IV-continued

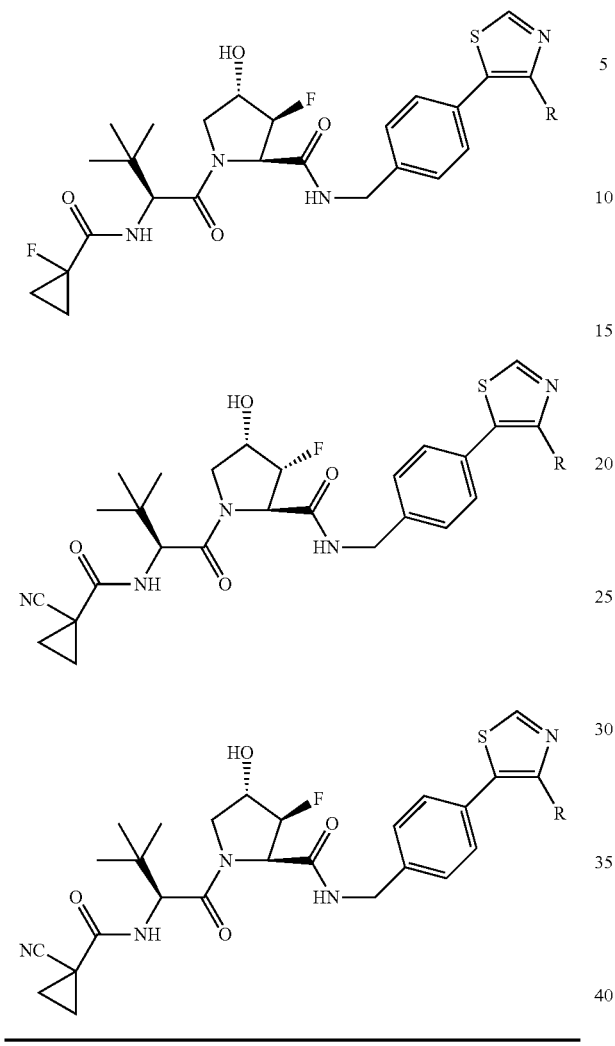

Thus there is also provided herein a Group IV of compounds for Formula IA, wherein X=N, Y=C(O)C(CH₃)₃, wherein R$^x$ and R$^{2b}$, R$^3$ and R$^4$ are all H, wherein R$^{2a}$ is OH, wherein L is as defined previously herein and is preferably A6 or A7, wherein R$^1$ is CH₃, a cyclopropyl group, a 1-fluorocyclopropyl group, or a 1-cyanocyclopropyl group, and wherein R$^5$ is a covalent bond to L.

Group V. Compounds of Formula IB with Linkage to L at the R$^8$ Position and R$^8$=—S—R$^{8*}$.

TABLE V

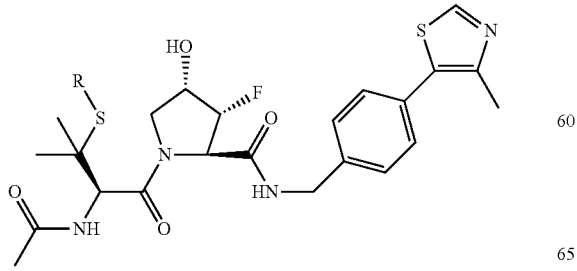

TABLE V-continued

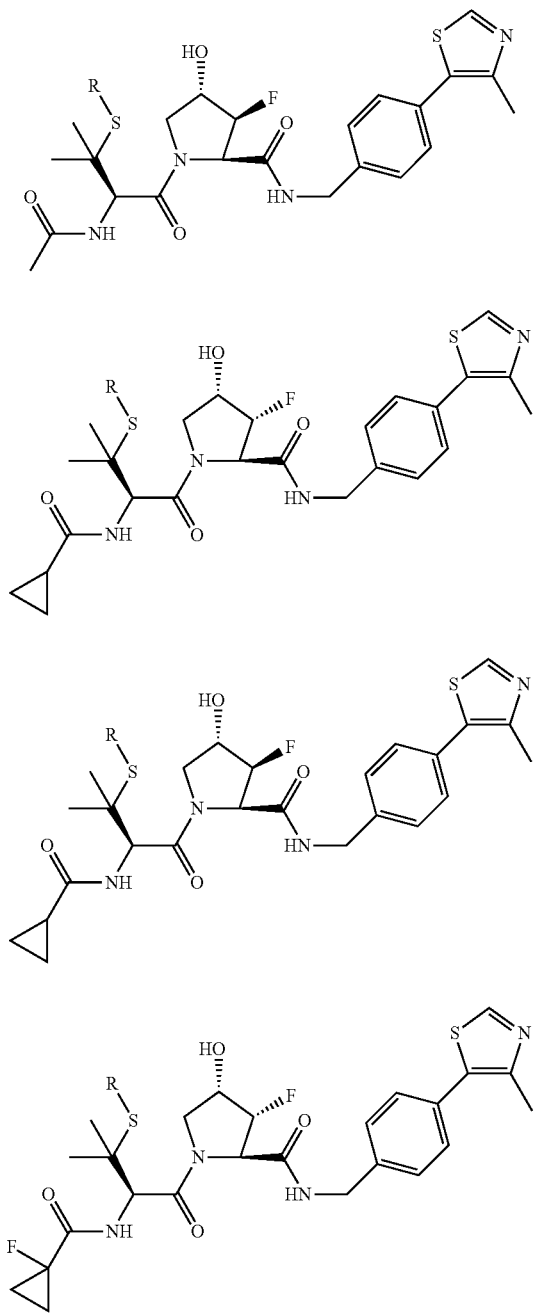

TABLE V-continued

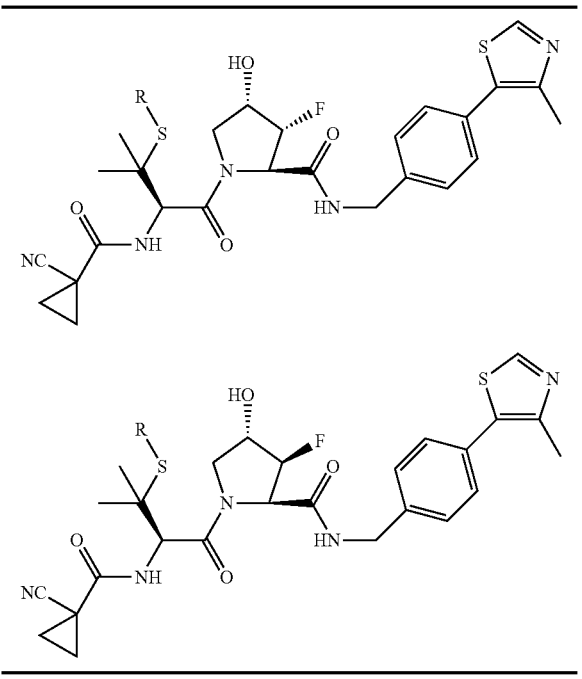

Thus there is also provided herein a Group V compound for Formula IA, wherein X=N, Y=C(O)C(CH$_3$)$_3$, wherein R$^x$ and R$^{2b}$, R$^3$ and R$^4$ are all H, wherein R$^{2a}$ is OH, wherein R$^5$ is CH$_3$, wherein L is as defined previously herein and is preferably A6 or A7, wherein R$^1$ is CH$_3$, a cyclopropyl group, a 1-fluorocyclopropyl group, or a 1-cyanocyclopropyl group, and wherein R$^8$ is an S-linked covalent bond to L.

BIOLOGICAL METHODS

Figures 1, 2:
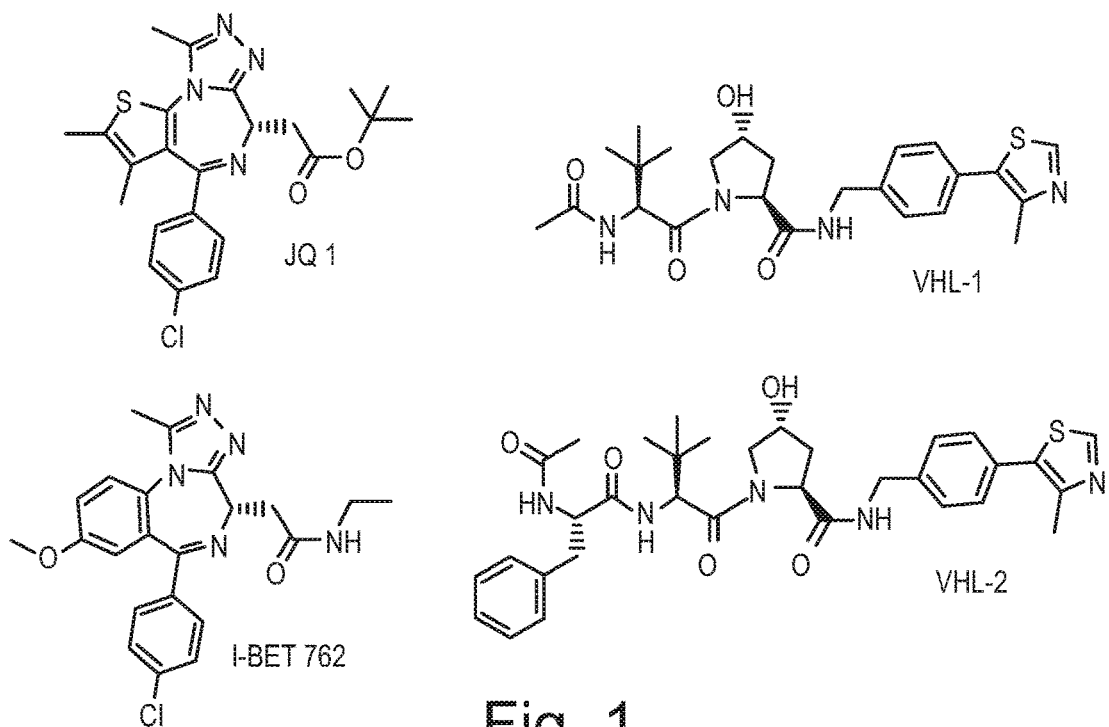
FIG. 1: illustrates the structures of compounds JQ1, VHL-1, I-BET 762 and VHL-2.
FIG. 2 illustrates the binding affinities and ΔH against first and second bromodomains and VBC obtained in isothermal titration calorimetry (ITC) experiments for previously reported non-fluorinated PROTACs MZ1, MZ2 and MZ3, bromodomain inhibitor JQ1 and previously reported VHL ligand VHL-1.
Figure 3:
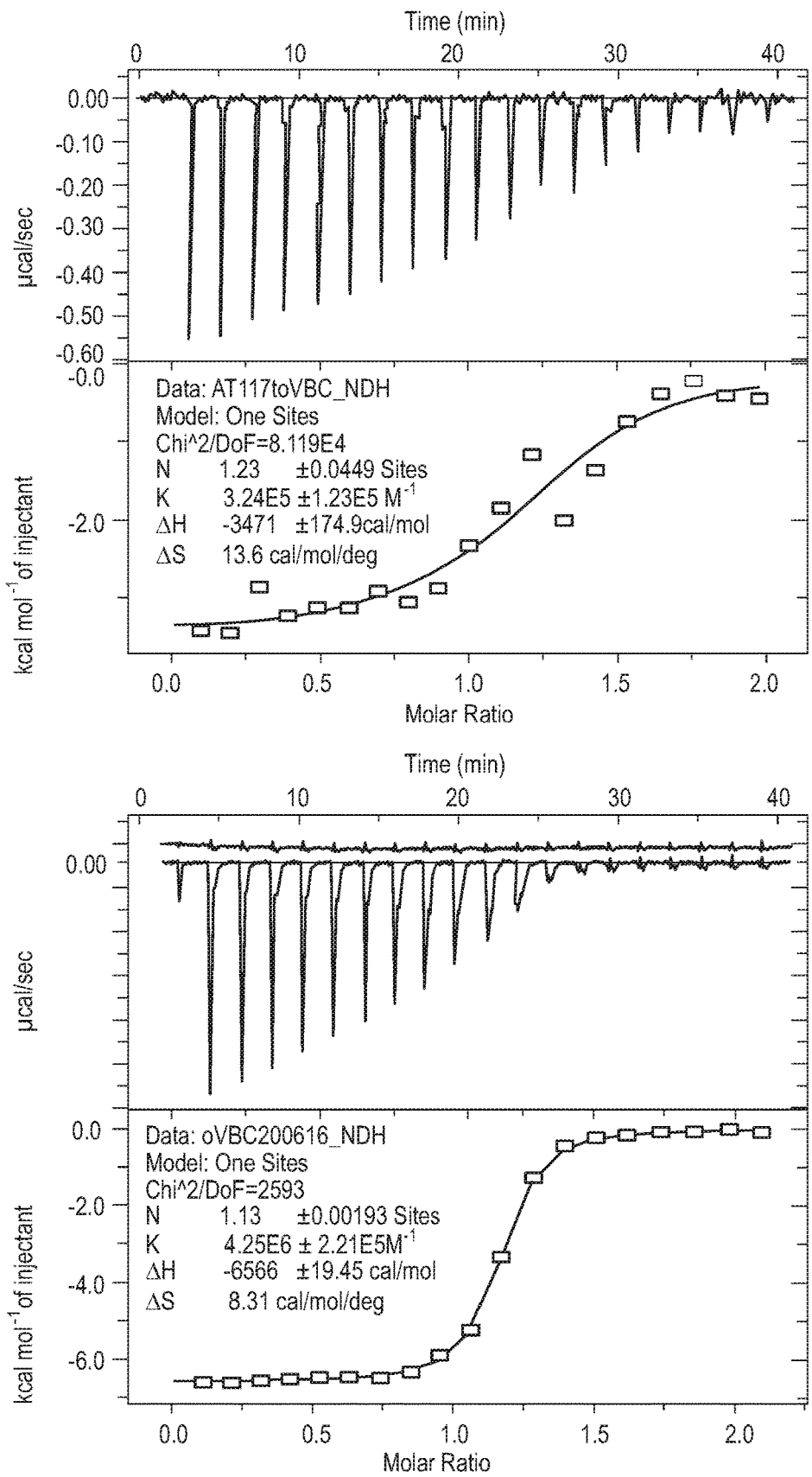
FIG. 3: illustrates the binding affinities and ΔH against VBC obtained in isothermal titration calorimetry (ITC) experiments for VHL ligands 14b (Kd=0.235 µM, ΔH=−6566 cal/mol, ΔS=8.30 cal/mol/deg) and 14d (Kd=0.235 µM, ΔH=−6566 cal/mol, ΔS=8.30 cal/mol/deg).
Figure 4A:
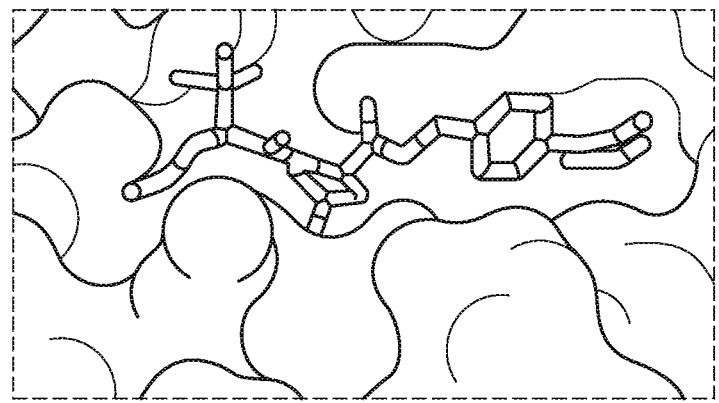
FIG. 4A: is a representation of the protein-ligand crystal structure of VHL-1 where the scaffold of VHL-1 is seen in 3D-format.
Figure 4B:
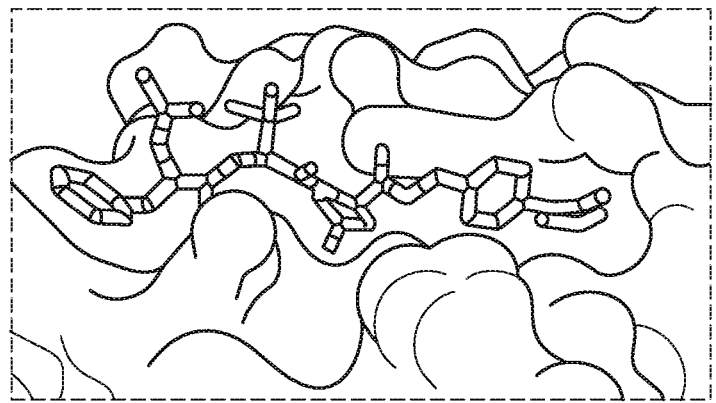
FIG. 4B: is a representation of the protein-ligand crystal structure of VHL-2 where the scaffold of VHL-2 is seen in 3D-format.
Figure 4C:
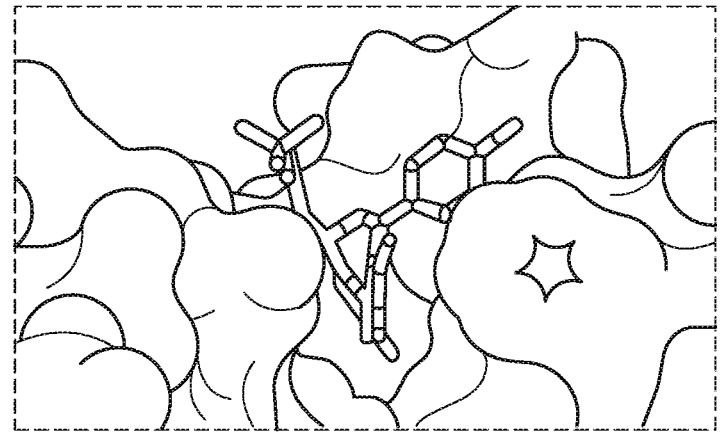
FIG. 4C: is a representation of the protein-ligand crystal structure of JQ1 where the scaffold of JQ1 is seen in 3D-format.
Figure 5:
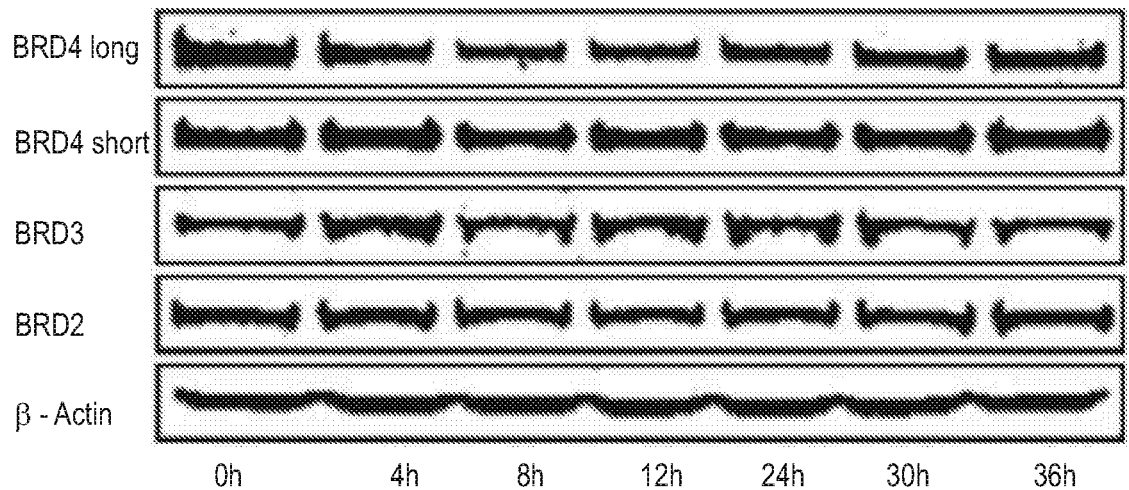
FIG. 5: illustrates the Time dependent treatment over 36 h of HeLa cells with (a) 0.01% DMSO, (b) 1 µM JQ1.
Figure 5:
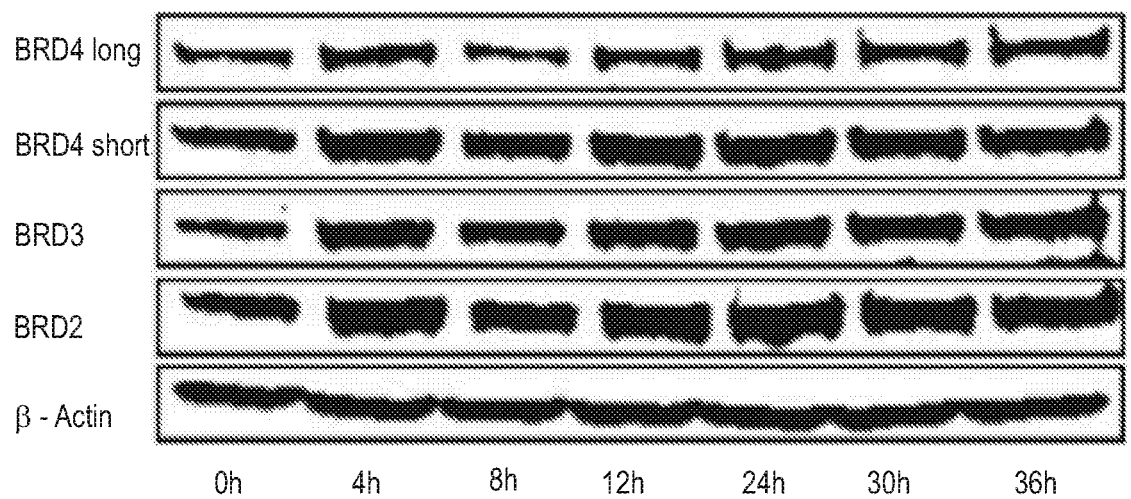
Figure 6:
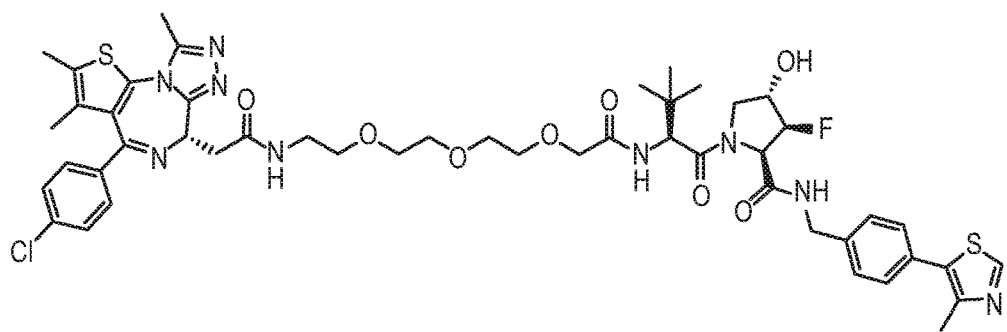
FIG. 6: illustrates the compound dose-dependent intracellular activities results obtained when HeLa cells were treated with various concentrations of PROTAC 18d against BRD2 and BRD4 (long and short isoforms) with an actin control. Protein levels were visualised by immunoblot (middle panel) and quantified relative to DMSO control (bottom panel).
Figure 6:
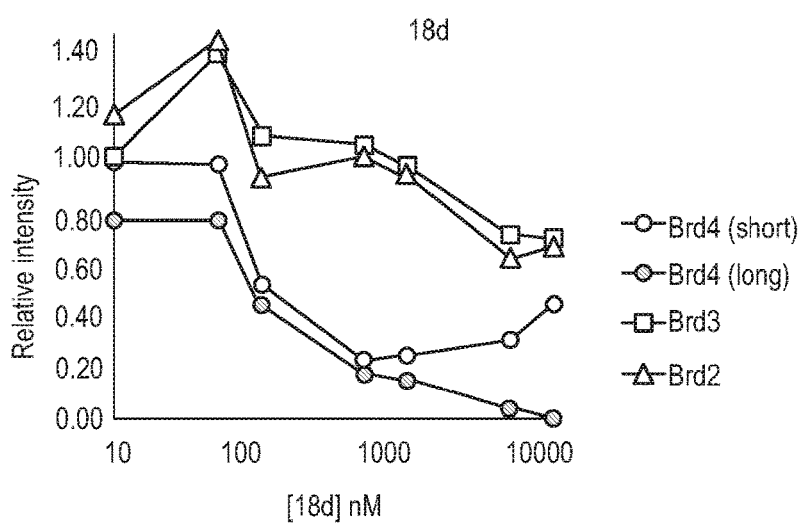
Figure 6:
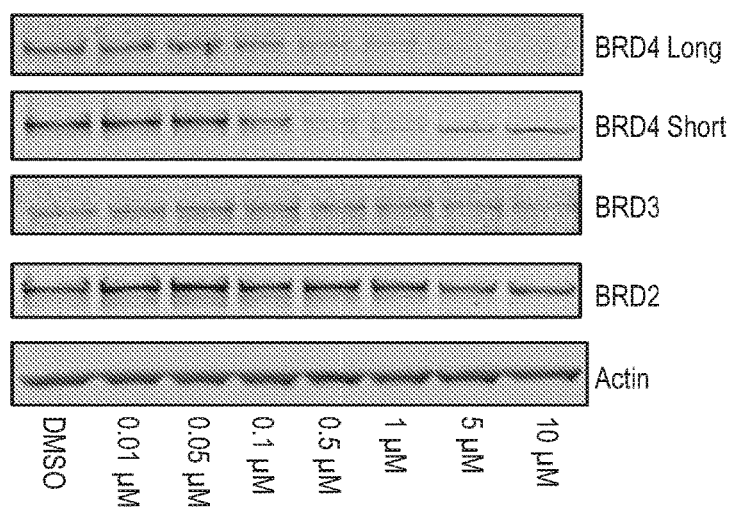
Figure 7:
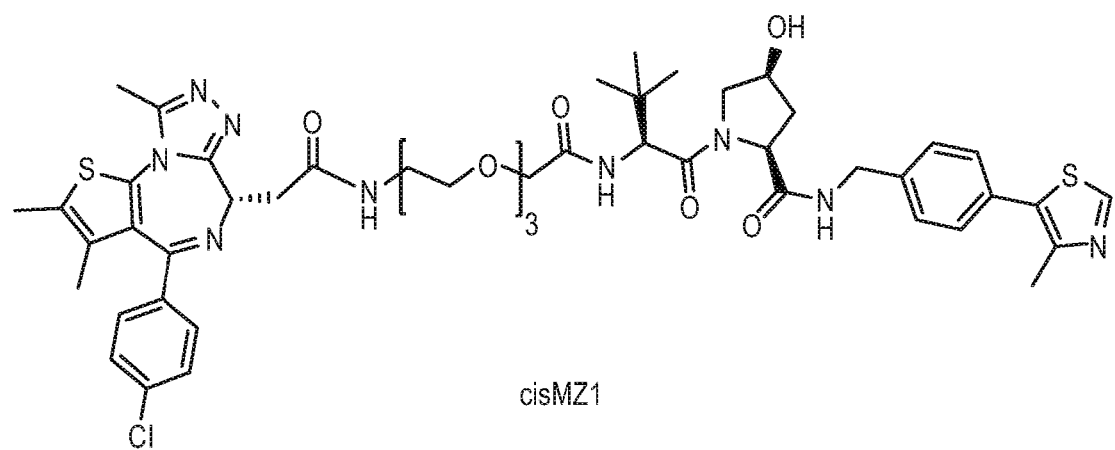
FIG. 7: illustrates the structures of cisMZ1, (2S,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide and MZ1, (2S,4R)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide.
Figure 7:
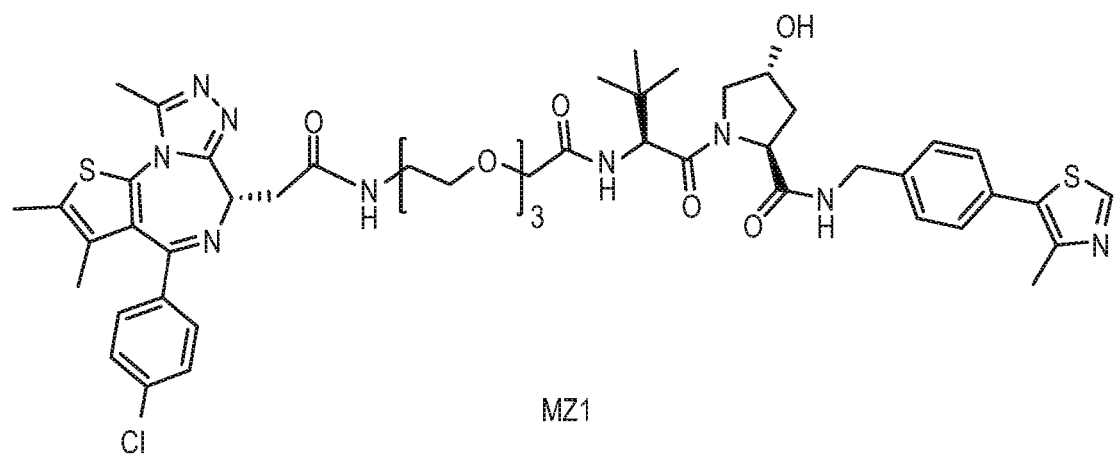
Figure 8:
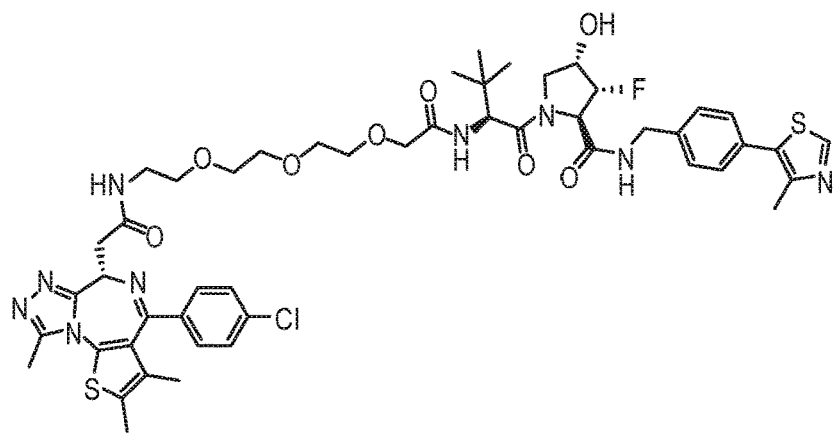
FIG. 8 illustrates the structure of (2R,3R,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-3-fluoro-4-hydroxy-N-(4-(4-methylthiazol-5-yl)benzyl)pyrrolidine-2-carboxamide 18b and further illustrates the compound dose-dependent intracellular activities results obtained when HeLa cells were treated with various concentrations of PROTAC 18b against BRD2, BRD3 and BRD4 (long and short isoforms). Protein levels were visualized by immunoblot and quantified (bottom graph).
Figure 8:
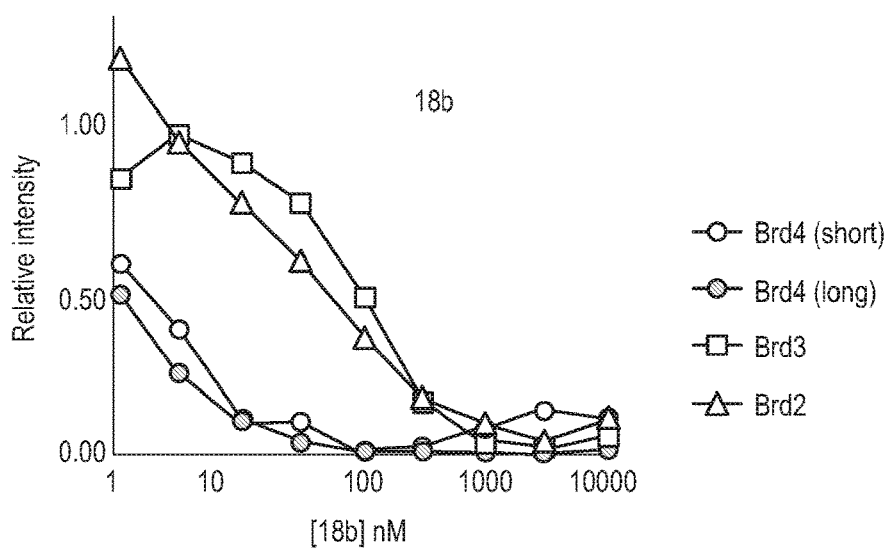
Figure 8:
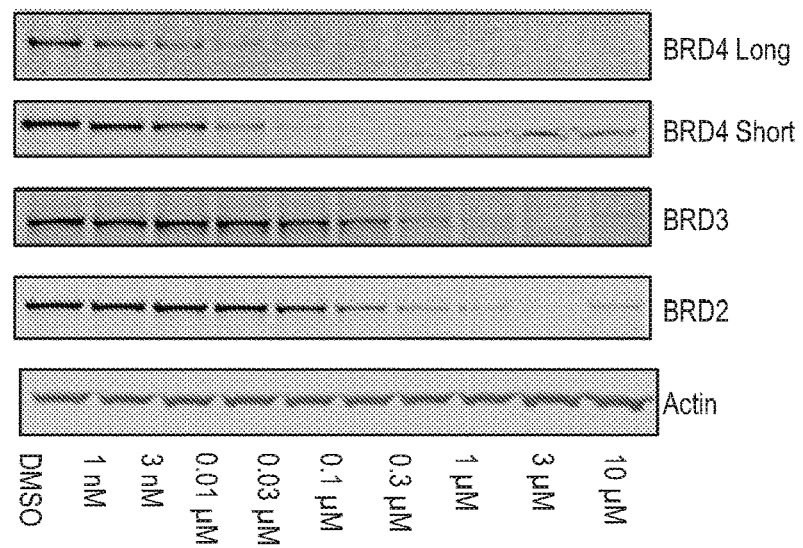
Figure 9:
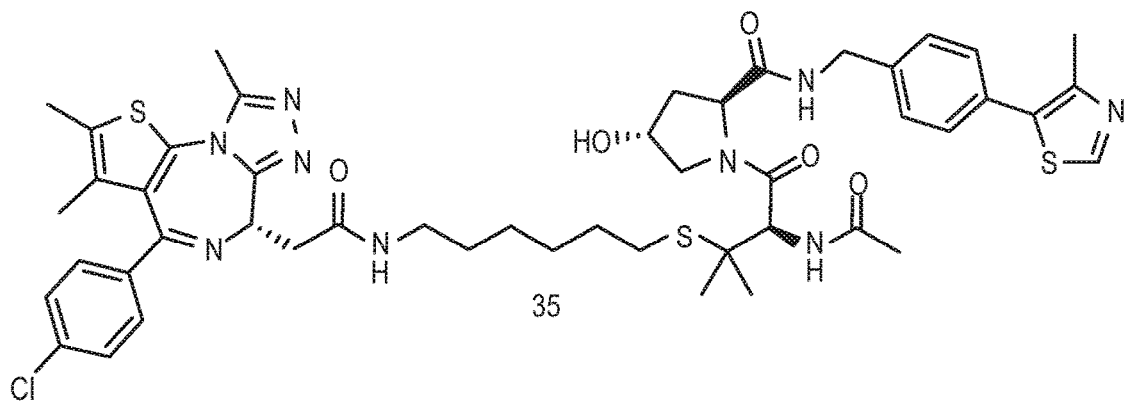
FIG. 9 illustrates the structure of (2S,4R)-1-((R)-2-acetamido-3-((6-(2-((S)-4-(4-chlorophenyl)-2,3,9-trimethyl-6H-thieno[3,2-f][1,2,4]triazolo[4,3-a][1,4]diazepin-6-yl)acetamido)hexyl)thio)-3-methylbutanoyl)-4-hydroxy-N-(4-(4-methylthiazol-5-yl)benzyl)pyrrolidine-2-carboxamide 35 and further illustrates the compound dose-dependent intracellular activities results obtained when HeLa cells were treated with various concentrations of PROTAC 35 against BRD2, BRD3 and BRD4 (long and short isoforms). Protein levels were visualized by immunoblot (left panel) and quantified (right graph).
Figure 9:
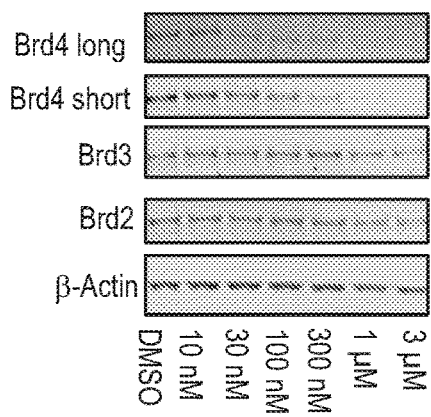
Figure 9:
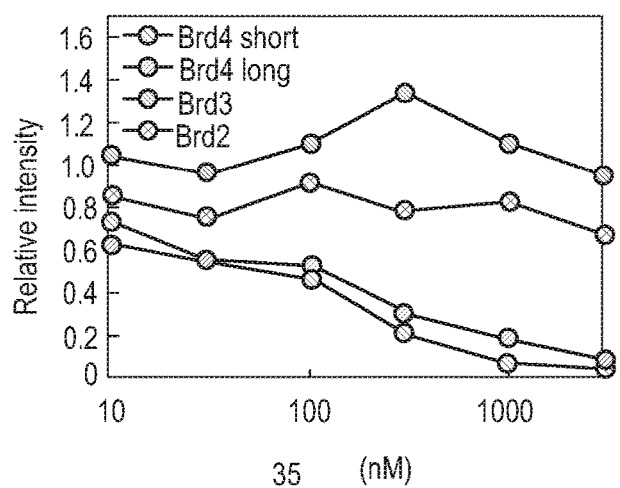

ITC Data on the Binding of VHL Ligands 14b and 14d

Titrations were performed on an ITC200 micro-calorimeter (GE Healthcare). Compounds 14b and 14d were diluted from a DMSO stock solution to 0.6 mM in a 20 mM HEPES, 150 mM NaCl, 1 mM TCEP (pH 7) buffer. The compound was titrated against 60 µM VBC complex, equilibrated in the same buffer. Total amount of DMSO in the buffer was 3%. The data were fitted to a single binding site model to obtain the stoichiometry n, the dissociation constant K$_d$ and the enthalpy of binding ΔH using the Microcal LLC ITC200 Origin software provided by the manufacturer.

Tissue Culture

HeLa cells were cultured in DMEM supplemented with 10% FBS, 1% L-glutamine and 100 U/ml of penicillin/streptomycin. Cells were maintained for no more than 30 passages at 37° C. and 5% CO$_2$.

Western Blotting

For protein extracts the dishes were placed on ice. The media was aspirated and the tissue layer washed twice with ice cold PBS. 120 µl of RIPA-buffer containing Protease inhibitor was added and the cells detached from the surface with a cell scraper. After removal of the insoluble fraction by centrifugation the protein concentration of the supernatant was determined by a Pierce™ BCA Protein Assay Kit. Protein extracts were fractionated by SDS-PAGE on 3-8% Tris-Acetate NuPage® Novex® (Life Technologies) polyacrylamide gels and transferred to a nitrocellulose membrane using i-Blot® 2 from Life Technologies. The membrane was then blocked with 3.5% Bovine Serum albumin (BSA) in Tris-buffered saline (TBS) with 0.1% Tween-20. For detecting proteins the following primary antibodies in the given concentrations were used: anti-BRD2 (Abcam, ab139690, EPR7642) 1:2000, anti-BRD4 (Abcam, ab128874, EPR5150(2)) 1:1000, anti-β-Actin (Cell Signaling Technology, 4970S, 13E5) 1:2000. For visualisation a Li-Cor Biosciences Odyssey system with the following secondary fluorescent Antibodies from Li-Cor Biosciences was used: IRDye800CW Goat Anti-Mouse (926-32210), IRDye800CW Donkey Anti-Rabbit (926-32213), both in concentrations of 1:10 000. Membranes were incubated with the corresponding antibodies either at 4° C. for 12 h or at 25° C. for 4 h. Between incubation with the different antibodies membranes were stripped with 0.25 M solution of Glycine.HCl at pH 2.

Pharmaceutical Compositions

PROTAC compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a PROTAC compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers.

In addition, they may also contain other therapeutically valuable substances. Suitable formulations for transdermal applications include an effective amount of a PROTAC compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present invention comprise a therapeutically effective amount of a PROTAC compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type.

The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the PROTAC compounds of the invention with suitable non-irritating excipients or carriers such as cocoa butter, polyethylene glycol or a suppository wax which are solid at ambient temperature but liquid at body temperature and therefore melt in the rectum or vaginal cavity and release the active compound. Solid compositions of a similar type may also be employed as fillers in soft and hard-filled gelatine capsules using such excipients as lactose or milk sugar as well as high molecular weight polyethylene glycols and the like.

The PROTAC compounds can also be provided in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the PROTAC compounds of this invention, excipients such as lactose, talc, silicic acid, aluminium hydroxide, calcium silicates and polyamide powder, or mixtures of these substances. Sprays can additionally contain customary propellants such as chlorofluorohydrocarbons. Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, diseases, conditions, or disorders are treated or prevented in a subject, such as a human or other animal, by administering to the subject a therapeutically effective amount of a PROTAC compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a PROTAC compound of this invention will be at a reasonable benefit/risk ratio applicable to any medical treatment.

The dosage for the instant compounds can vary according to many factors, including the type of disease, the age and general condition of the patient, the particular compound administered, and the presence or level of toxicity or adverse effects experienced with the drug. A representative example of a suitable dosage range is from as low as about 0.025 mg to about 1000 mg. However, the dosage administered is generally left to the discretion of the physician.

A wide variety of pharmaceutical dosage forms for mammalian patients can be employed. If a solid dosage is used for oral administration, the preparation can be in the form of a tablet, hard gelatin capsule, troche or lozenge. The amount of solid carrier will vary widely, but generally the amount of the PROTAC compound will be from about 0.025 mg to about 1 g, with the amount of solid carrier making up the difference to the desired tablet, hard gelatin capsule, troche or lozenge size. Thus, the tablet, hard gelatin capsule, troche or lozenge conveniently would have, for example, 0.025 mg, 0.05 mg, 0.1 mg, 0.5 mg, 1 mg, 5 mg, 10 mg, 25 mg, 100 mg, 250 mg, 500 mg, or 1000 mg of the present compound. The tablet, hard gelatin capsule, troche or lozenge is given conveniently once, twice or three times daily.

In general, PROTAC compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents. Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms. It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for pharmaceutical combinations, e.g. a kit, comprising a) a first agent which is a PROTAC compound of the invention as disclosed herein, in free form or in pharmaceutically acceptable salt form, and b) at least one co-agent. The kit can comprise instructions for its administration. The terms "co-administration" or "combined administration" or the like as utilized herein are meant to encompass administration of the selected therapeutic agents to a single patient, and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a PROTAC compound of the invention and a co-agent, are both administered to a patient simultaneously in the form of a single entity or dosage. The term "non-fixed combination" means that the active ingredients, e.g. a PROTAC compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminium hydroxide; alginic acid; pyrogen-free water, isotonic saline; Ringer's solution; ethyl alcohol, and phosphate buffer solutions, as well as other non-toxic compatible lubricants such as sodium lauryl sulphate and magnesium stearate, as well as colouring agents, releasing agents, coating agents, sweetening, flavouring and perfuming agents, preservatives and antioxidants can also be present in the composition, according to the judgment of the formulator.

Chemistry—Materials and Methods

All chemicals, unless otherwise stated were commercially available and used without further purification. Solvents were anhydrous and reactions preformed under positive pressure of nitrogen or argon. Enantiopure (+)-JQ-1 and I-BET726 were purchased from Medchemexpress LLC, Princeton, USA. Flash column chromatography (FCC) was performed using a Teledyne Isco Combiflash Rf or Rf200i. As prepacked columns RediSep Rf Normal Phase Disposable Columns were used.

NMR spectra were recorded on a Bruker 500 Ultrashield or a Bruker Ascend 400. Chemical shifts are quoted in ppm and referenced to the residual solvent signals: $^1$H δ=7.26 (CDCl$_3$), $^{13}$C δ=77.16 (CDCl$_3$), $^1$H δ=3.31 (MeOD), $^{13}$C δ=49.15 (MeOD), $^1$H δ=4.79 (D$_2$O). Signal splitting patterns are described as singlet (s), doublet (d), triplet (t), quartet (q), multiplet (m), broad (br) or a combination thereof. Coupling constants (J) are measured in Hz. Symbol "*" labels the signals of the minor rotamer when clearly distinguishable from the major one.

Low resolution MS and analytical HPLC traces were recorded on an Agilent Technologies 1200 series HPLC connected to an Agilent Technologies 6130 quadrupole LC/MS, connected to an Agilent diode array detector. The column used was a Waters XBridge column (50 mm×2.1 mm, 3.5 μm particle size) and the compounds were eluted with a gradient of 5-95% acetonitrile/water+0.1% formic acid over 3 minutes (METHOD 1) or over 7 minutes (METHOD 2).

Preparative HPLC was performed on a Gilson Preparative HPLC System with a Waters X-Bridge C18 column (100 mm×19 mm; 5 μm particle size) and a gradient of 5% to 95% acetonitrile in water over 10 minutes, flow 25 mL/min, with 0.1% ammonia in the aqueous phase.

Abbreviations used: ACN for acetonitrile, DCM for dichloromethane, EtOAc for ethyl acetate, Et$_2$O for diethyl ether, DMSO for dimethyl sulfoxide, DIPEA for N,N-diisopropylethylamine, MeOH for methanol, TEA for triethylamine, DMF for N,N-dimethylformamide, HATU for 1-[bis(dimethylamino)methylene]-1H-1,2,3-triazolo[4,5-b]pyridinium 3-oxid hexafluorophosphate, HOAT for 1-hydroxy-7-azabenzotriazole, TMSOTf for trimethylsilyltriflate, TFA for trifluoroacetic acid.

Preparatory Compounds for the Synthesis of F-HYP in Accordance with Scheme 1 Process Preparative Compound 1: 2-benzyl 1-(tert-butyl) (S)-4-oxopyrrolidine-1,2-dicarboxylate Preparative compound 1 was prepared from commercially available 2-benzyl 1-(tert-butyl) (2S,4R)-4-hydroxypyrrolidine-1,2-dicarboxylate in accordance with the method reported by Qui, Journal of Organic Chemistry, 67(20), 7162-7164. CrO$_3$ (17.0 g, 0.17 mol) was added slowly with stirring over 30 min to a solution of pyridine (30 mL) in DCM (80 mL) at 0° C. The mixture was warmed to room temperature and 2-benzyl 1-(tert-butyl) (2S,4R)-4-hydroxypyrrolidine-1,2-dicarboxylate (6.0 g, 18.69 mmol) in DCM (60 mL) was added under stirring. The reaction was stirred vigorously for 4 h at room temperature. The formed dark solid was decanted and washed with DCM (3×100 mL). The organic phases were washed with saturated aqueous NaHCO$_3$, 10% aqueous critic acid, and brine and dried over anhydrous MgSO$_4$. The solvent was removed in vacuo to yield an oily residue, which was purified by flash chromatography (heptane/ethyl acetate, 3:1) to give 4 (5.0 g, 84%) as a clear oil. $^1$H NMR (400 MHz, CDCl$_3$) δ: 7.35 (m, 5H), 5.28-5.09 (m, 2H), 4.88-4.72 (dd, J=10.2, 9.3 Hz, 1H), 3.92-3.87 (d, J=13.5 Hz, 2H), 2.97-2.91 (m, 1H), 2.64-2.54 (m, 1H), 1.47-1.37 (m, 9H).

Preparative Compound 2: 2-benzyl 1-(tert-butyl) (2R)-3-fluoro-4-oxopyrrolidine-1,2-dicarboxylate

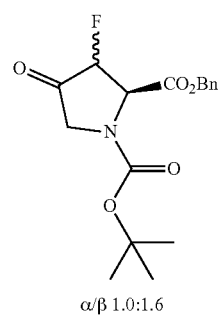 [SMILES: CC(C)(C)OC(=O)N1CC(=O)C(F)[C@H]1C(=O)OCc1ccccc1]

α/β 1.0:1.6

A solution of 2-benzyl 1-(tert-butyl) (S)-4-oxopyrrolidine-1,2-dicarboxylate (1) (1.255 g, 3.929 mmol) in THF (5 mL) was added dropwise to a stirred solution of LHMDS (1M in THF, 4.35 mL) in THF (4.35 mL) at −78° C. The mixture was stirred at −78° C. for 2 hr, then TMSCl (1.25 mL, 10 mmol) was added dropwise. After 30 minutes of continued stirring at −78° C., the cooling bath was removed and the reaction mixture was allowed to warm to r.t. and stirred for additional 3 hours. The reaction mixture was then concentrated under vacuum to small volume, pentane (50 mL) was added and the mixture was poured into a saturated solution of NaHCO$_3$ (100 mL). The mixture was vigorously shaken and the organic layer was separated, washed with brine, then dried over anhydrous MgSO$_4$. The volatiles were removed under reduced pressure to obtain a light yellow oil corresponding to the trimethylsilylenolate which was dissolved in acetonitrile (60 mL) and cooled to 0° C. Selectfluor (2.040 g, 5.750 mmol) was added in one portion and the mixture was carefully allowed to reach 10° C. over a 3 hr period. TLC analysis (EtOAc/Heptane 3:7) showed complete conversion of the starting material A saturated solution of NH$_4$Cl was added (30 ML), the resulting mixture was vigorously shaken and the organic layer was separated. The aqueous layer was extracted with EtOAc (2×30 mL) and the organic phase was washed with brine, then dried over MgSO$_4$. Volatiles were removed under reduced pressure to obtain a yellow oil which was quickly passed through a short silica column eluted with a mixture of EtOAc/Heptane 4:6 to obtain the desired crude fluoroketone (2) (662 mg 50% yield) as a mixture of diasteroisomers. This crude mixture proved to be unstable in solution and therefore was used immediately in the next step. $^1$H-NMR (mixture of diasteroisomers and their cis/trans rotamer, CDCl$_3$) δ: 7.40-7.34 (m, 5H), 5.38-4.81 (m, 4H), 4.12-3.95 (m, 2H), 1.49-1.39 (m, 9H). $^{19}$F NMR δ –186.91, –187.57 (α isomer) –205.18, –205.92 (β isomer).

Alternatively, 2-Benzyl 1-(tert-butyl) (S)-4-((trimethylsilyl)oxy)-2,5-dihydro-1H-pyrrole-1,2-dicarboxylate and Selectfluor™ were dissolved in anhydrous acetonitrile (0.67 M and 0.1 M respectively) and stored under inert atmosphere. The solutions of silyl enol ether and Slectfluor were pumped at a rate of 0.77 mL/min in a 10 mL flow reactor (residence time 6.5 min) heated at 50° C. The crude product treated with a saturated solution of NH$_4$Cl and extracted with ethyl acetate and the organic phase was dried over MgSO4. Solvents were evaporated to obtain the crude product which can be further purified by column chromatography on silica accordingly to the conditions described for the batch synthesis above. This flow process provided a reliable and constant yield of fluorinated products while providing a ratio of the diastereoisomers as disclosed for the batch process.

Reduction of 2-benzyl 1-(tert-butyl) (2R)-3-fluoro-4-oxopyrrolidine-1,2-dicarboxylate with NaBH$_4$ to Prepare Preparative Compounds 3a, 3b, and 3c Fluoroketone 2 (500 mg, 1.482 mmol) was dissolved in a mixture of THF/EtOH 1:1 (10 mL) and cooled to 0° C. NaBH$_4$ (56 mg, 1.482 mmol) was added portion-wise and the reaction mixture was stirred for 1 hour at 0 C. TLC analysis (EtOAc/Heptane 1:1) showed complete conversion of the starting material. The reaction mixture was concentrated under vacuum, EtOAc was added (15 mL) and a solution of NaHSO$_4$ (5%) was added dropwise until a pH of 3 to 4 was obtained. The acidified mixture was then washed with brine (10 mL), and the organic phase was dried over anhydrous MgSO$_4$. Volatiles were removed under reduced pressure to obtain yellow oil which was subjected to FCC (EtOAc/Heptane 3:7 to 1:1) to separate the 3 diasteroisomers (described herein in order of elution). Alternatively, the mixture was dissolved in methanol (8 mL) and purified by preparative HPLC (5-90% ACN in H$_2$O over 15 min).

Preparative Compound 3c: 2-benzyl 1-(tert-butyl) (2R,3R,4R)-3-fluoro-4-hydroxypyrrolidine-1,2-dicarboxylate

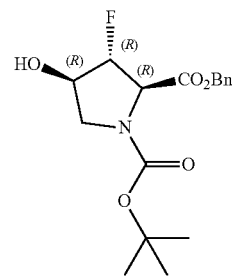

(11% by $^{19}$F-NMR, white solid, 8% isolated yield) $^1$H-NMR (CDCl$_3$) δ: 7.37-7.36 (m, 5H), 5.33-5.15 (m, 2H), 4.99 (d, J$_{H-F}$=49.1 Hz, 1H), 4.95* (d, J$_{H-F}$=49.0 Hz, 1H), 4.60* (d, J$_{H-F}$=24.8 Hz, 1H), 4.48 (d, J$_{H-F}$=24.8 Hz, 1H), 4.33-4.29 (m, 1H), 3.74-3.64 (m, 1H), 2.81* (d, J$_{H-H}$=9.3 Hz, 1H), 2.72 (d, J$_{H-H}$=9.5 Hz, 1H), 1.48* (s, 9H), 1.34 (s, 9H). $^{19}$F-NMR –179.71*, –180.11. $^{13}$C NMR: 170.5 (d, J$_{C-F}$=15.9 Hz), 154.3*, 153.6, 134.89*, 134.72, 128.83, 128.75, 128.71, 128.64, 128.56, 128.27, 96.96 (d, J$_{C-F}$ 191.1 Hz), 95.91* (d, J$_{C-F}$ 191.2 Hz), 80.98, 80.94*, 73.64* (d, J$_{C-F}$=27.8 Hz), 72.71 (d, J$_{C-F}$=29.0 Hz), 67.97, 64.67 (d, J$_{C-F}$=24.7 Hz), 64.41* (d, J$_{C-F}$=24.4 Hz), 53.31*, 52.87, 28.34*, 28.112. C$_{17}$H$_{22}$FNO$_5$, expected 339.2, found m/z=240.1, [M-Boc+H]$^+$.

Preparative Compound 3b: 2-benzyl 1-(tert-butyl) (2R,3R,4S)-3-fluoro-4-hydroxypyrrolidine-1,2-dicarboxylate

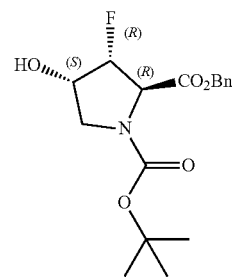

(30% by $^{19}$F-NMR, white solid, 25% isolated yield) $^1$H-NMR (CDCl$_3$) δ: 7.38-7.35 (m, 5H), 5.29-5.11 (m, 2H), 4.99-4.88 (m, 1H), 4.64-4.47 (m, 1H), 4.41-4.36 (m, 1H), 3.94-3.87 (m, 1H), 3.37-3.27 (m, 1H), 2.09 (d, J$_{H-H}$ 7.45 Hz), 1.47* (9H), 1.33 (9H). $^{19}$F-NMR δ: –199.74, –200.29*. $^{13}$C-NMR δ: 169.1 (d, J$_{C-F}$=13.1 Hz), 168.7* (d, J$_{C-F}$=12.9 Hz), 154.07*, 153.21, 135.10*, 134.9, 128.8, 128.6, 128.5, 128.2, 94.0 (d, J$_{C-F}$=190.0 Hz), 93.2* (d, J$_{C-F}$=189.6 Hz), 80.9, 70.3* (d, J$_{C-F}$=18.2 Hz), 69.6, J$_{C-F}$=17.0 Hz), 67.6, 63.7 (d, J$_{C-F}$=23.9 Hz), 63.5* (d, J$_{C-F}$=23.8 Hz), 49.8*, 49.3, 23.8*, 28.1. C$_{17}$H$_{22}$FNO$_5$, expected 339.2, found m/z=240.1, [M-Boc+H]$^+$.

Preparative Compound 3a: 2-benzyl 1-(tert-butyl) (2R,3S,4R)-3-fluoro-4-hydroxypyrrolidine-1,2-dicarboxylate

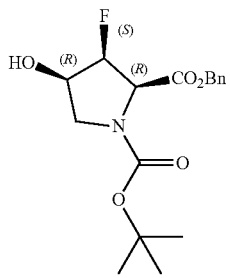

(58% by $^{19}$F-NMR, white solid, 50% isolated yield). $^1$H-NMR (CDCl$_3$) δ: 7.37-7.32 (m, 5H), 5.35-5.10 (m, 3H), 4.64* (dd, J$_{H-F}$=21.0 Hz, J$_{H-H}$ 5.9 Hz, 1H), 4.54 (dd, J-H—F=21.7 Hz, J$_{H-H}$ 5.9 Hz, 1H), 4.28 (br s, 1H), 3.87 (dd, J$_{H-H}$=11.2 Hz, J$_{H-H}$=6.6 Hz, 1H), 3.82* (dd, J$_{H-H}$=11.1 Hz, J$_{H-H}$=6.6 Hz, 1H), 3.48-3.41 (m, 1H), 2.75 (br s, 1H), 1.46* (s, 9H), 1.32 (s, 9H). $^{19}$F-NMR δ: −207.06, −207.67*. $^{13}$C-NMR δ: 168.3 (d, J$_{C-F}$=7.0 Hz), 167.9* (d, J$_{C-F}$=7.2 Hz), 153.9*, 153.2, 135.2*, 135.0, 128.6, 128.5, 128.4, 128.3, 128.2, 91.5 (d, J$_{C-F}$=189.6 Hz), 90.8* (d, J$_{C-F}$=188.6 Hz), 81.1, 70.6* (d, J$_{C-F}$=17.7 Hz), 70.1 (d, J$_{C-F}$=17.6 Hz), 67.6, 61.6 (d, J$_{C-F}$=21.9 Hz), 61.2* (d, J$_{C-F}$=22.0 Hz), 50.6*, 50.0, 28.3*, 28.1. C$_{17}$H$_{22}$FNO$_5$, expected 339.2, found m/z=240.1, [M-Boc+H]$^+$.

Mitsunobu Inversion, General Procedure in Accordance with Stage (iii) in Scheme 1 Process.

To a solution of fluoro-hydroxyproline (0.435 mmol), triphenylphosphine (342.0 mg, 1.306 mmol) and 4-nitrobenzoic acid (218.2 mg, 1.306 mmol) in THF (2 mL), diisopropyl azodicarboxylate (DIAD) was added dropwise at 0° C. The flask was left at 0° C. for 4 hr, then the ice bath was removed and the mixture was stirred at r.t. for 24 hr. Et$_2$O was added (10 mL) and the mixture was washed with saturated NaHCO$_3$ (5 mL). The mixture was washed with brine (10 mL), the organic phase was dried over anhydrous MgSO$_4$. Volatiles were removed under reduced pressure to obtain yellow oil which was subjected to FCC (EtOAc/Heptane 1:9 to 3:7) to isolate the desired product.

Preparative Compound 4a: 2-benzyl 1-(tert-butyl) (2R,3S,4S)-3-fluoro-4-((4-nitrobenzoyl)oxy) pyrrolidine-1,2-dicarboxylate

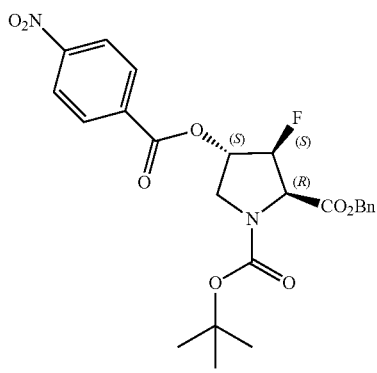

Preparative compound 4a was obtained from preparative compound 3a according to the general procedure for the Mitsunobu reaction as detailed hereinbefore (187 mg, 88% isolated yield), as a pale yellow wax. $^1$H-NMR (CDCl$_3$) δ: 8.31-8.29 (m, 2H), 8.17-8.15 (m, 2H), 7.38-7.35 (m, 5H), 5.57-5.54 (m, 1H), 5.45-5.33 (m, 1H), 5.31-5.16 (m, 2H), 4.84* (dd, J$_{H-F}$=23.3 Hz, J$_{H-H}$=5.7 Hz, 1H), 4.72 (dd, J$_{H-F}$=24.32 Hz, J$_{H-H}$=5.5 Hz, 1H), 4.05-4.00 (m, 1H), 3.90 (d, J$_{H-H}$=12.8 Hz, 1H), 3.76* (d, J$_{H-H}$=12.7 Hz), 1.46* (s, 9H), 1.36 (s, 9H). $^{19}$F-NMR δ: −192.43, −193.28*. C$_{24}$H$_{25}$FN$_2$O$_8$, rt=1.962 min, expected 488.1, found m/z=389.1, [M-Boc+H]$^+$.

Preparative Compound 4b: 2-benzyl 1-(tert-butyl) (2R,3R,4R)-3-fluoro-4-((4-nitrobenzoyl)oxy) pyrrolidine-1,2-dicarboxylate

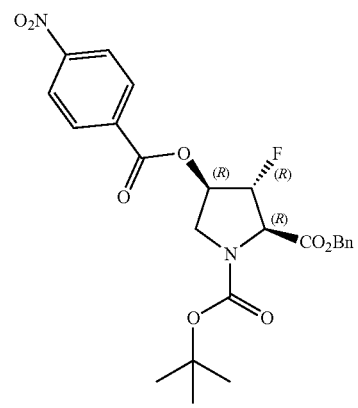

Preparative compound 4b was obtained from preparative compound 3b according to the general procedure for the Mitsunobu reaction as detailed hereinbefore (30 mg, 95% yield, light yellow wax). $^1$H NMR (500 MHz, CDCl$_3$) 8.22-8.18 (m, 2H), 8.02-7.95 (m, 2H), 7.26-7.22 (m, 5H), 5.57-5.54 (m, 1H), 5.34-5.06 (m, 3H), 4.89-4.67 (m, 1H), 4.03-3.96 (m, 1H), 3.88-3.74 (m, 1H), 1.50* (s, 9H), 1.40 (s. 9H). $^{19}$F-NMR δ: −182.16, −183.06*. C$_{24}$H$_{25}$FN$_2$O$_8$, rt=1.975 min, expected 488.1, found m/z=389.1, [M-Boc+H]$^+$.

Preparative Compound 3d: 2-benzyl 1-(tert-butyl) (2R,3S,4S)-3-fluoro-4-hydroxypyrrolidine-1,2-dicarboxylate

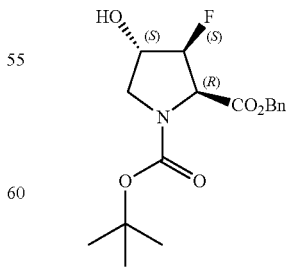

To a solution of the 4-nitrobenzonate ester, preparative compound 4a (24.4 mg, 0.05 mmol) in methanol (1.0 mL), sodium azide (10 mg, 0.15 mmol) was added under stirring.

The mixture was heated and stirred to 50° C. until TLC analysis (EtOAc/Heptane 4:6) showed complete conversion of the starting material (15-30 min). The mixture was cooled to 0° C., brine was added (1 mL) and extracted with EtOAc (3×5 mL). The organic phase was dried over anhydrous MgSO₄, the volatile components (solvent) were removed under reduced pressure, to obtain a yellow oil which was subjected to FCC (EtOAc/Heptane 1:1) to isolate the desired product (13.5 mg, 80% isolated yield) as a pale yellow wax. ¹H-NMR (CDCl₃) δ: 7.36-7.35 (m, 5H), 5.31-5.05 (m, 3H), 4.74* (dd, $J_{H-F}$=24.3 Hz, $J_{H-H}$ 5.1 Hz, 1H), 4.65 (dd, $J_{H-F}$=25.5 Hz, $J_{H-H}$ 5.2 Hz, 1H), 4.45-4.42 (m, 1H), 3.77-3.74 (m, 1H), 3.68-3.56 (m, 1H), 2.33 (br s, 1H), 1.46* (s, 9H), 1.33 (s, 9H). ¹⁹F-NMR δ: −192.30, −192.41*. ¹³C-NMR δ: 167.5 (d, $J_{C-F}$=8.3 Hz), 167.3* (d, $J_{C-F}$=10.8 Hz), 154.4*, 153.9, 135.4*, 135.3, 130.7, 128.6, 128.5, 123.2, 123.6, 95.5 (d, $J_{C-F}$=187.7 Hz), 94.8* (d, $J_{C-F}$=187.3 Hz), 80.9, 80.8*, 72.8* (d, $J_{C-F}$=28.0 Hz), 72.1 (d, $J_{C-F}$=27.0 Hz), 67.2, 62.4 (d, $J_{C-F}$=21.2 Hz), 61.9* (d, $J_{C-F}$=21.0 Hz), 52.1*, 51.8, 28.4*, 28.1. $C_{17}H_{22}FNO_5$, expected 339.2, found m/z=240.1, [M-Boc+H]⁺.

Preparative Compound 3c: 2-benzyl 1-(tert-butyl) (2R,3R,4R)-3-fluoro-4-hydroxypyrrolidine-1,2-dicarboxylate

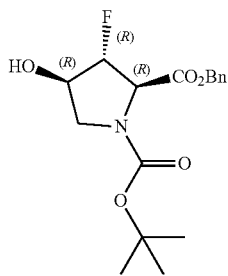

Preparative compound 3c, was obtained following the procedure as reported hereinbefore for preparative compound 3d. The desired product was obtained in 83% isolated yield as a transparent oil, analytical data matches with the product obtained from the direct reduction of the fluoroketone 3c.

General Procedure for the De-Benzylation of Benzylester Intermediate Preparative Compounds in Accordance with Stage (v) of Scheme 1 Process The selected benzyl ester 3a, 3b, 3c or 3d (85 mg, 0.250 mmol) was dissolved in a mixture of MeOH/THF 1:2 (15 mL), a catalytic amount of palladium over carbon (10%, dry) was added and the mixture was stirred under hydrogen atmosphere until TLC analysis (EtOAc/Heptane 1:1) showed complete conversion of the starting material. The mixture was then filtered on a celite pad and the solvents were removed in vacuum to obtain the de-benzylated product which was used directly in the next stage without further purification.

Preparative Compound 5d: (2R,3S,4S)-1-(tert-butoxycarbonyl)-3-fluoro-4-hydroxypyrrolidine-2-carboxylic Acid

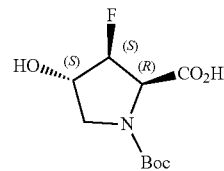

Starting from the corresponding preparative benzyl ester, 4d using the de-benzylation procedure detailed hereinbefore preparative compound 5d was obtained as a white solid (62 mg) in 99% isolated yield. ¹H-NMR (CD₃OD) δ: 5.13-4.99 (m, 1H), 4.61-4.50 (m, 1H), 4.30-7.27 (m, 1H), 3.61-3.54 (m, 2H), 1.476* (s, 9H), 1.44 (s, 9H). ¹⁹F-NMR δ: −191.59, −191.73*. ¹³C-NMR δ: 169.6 (d, $J_{C-F}$=8.5 Hz), 169.2* (d, $J_{C-F}$=8.4 Hz), 155.0*, 154.6, 95.5 (d, $J_{C-F}$=186.0 Hz), 95.2* (d, $J_{C-F}$=128.5 Hz), 80.6, 80.4*, 71.9* (d, $J_{C-F}$=26.6 Hz), 71.3 (d, $J_{C-F}$=26.7 Hz), 62.4 (d, $J_{C-F}$=21.3 Hz), 62.0* (d, $J_{C-F}$=21.6 Hz), 52.2*, 51.3, 27.3*, 27.0. $C_{10}H_{16}FNO_5$, expected 249.1, found m/z=150.1, [M-Boc+H]⁺.

Preparative Compound 5b: (2R,3R,4S)-1-(tert-butoxycarbonyl)-3-fluoro-4-hydroxypyrrolidine-2-carboxylic Acid

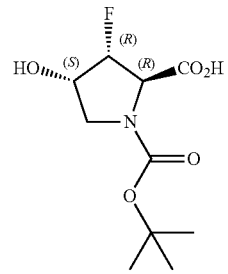

Starting from the corresponding preparative benzyl ester, 4b using the de-benzylation procedure detailed hereinbefore preparative compound 5b was obtained as a white solid (62 mg) in 99% isolated yield. ¹H-NMR (CD3OD) δ: 5.01-4.93 (m, 1H), 4.43-4.27 (m, 2H), 3.78-3.74 (m, 1H), 3.30-3.28 (m, 1H), 1.49* (s, 9H), 1.44 (s, 9H). ¹⁹F-NMR δ: −199.02, −199.10*. $C_{10}H_{16}FNO_5$, expected 249.1, found m/z=150.1, [M-Boc+H]⁺.

Preparative Compound 5e: (2R,3S,4S)-1-(((9H-fluoren-9-yl)methoxy)carbonyl)-3-fluoro-4-hydroxy-pyrrolidine-2-carboxylic Acid

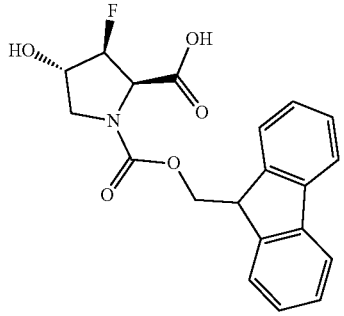 [SMILES: O=C(O)[C@@H]1[C@H](F)[C@@H](O)CN1C(=O)OCC1c2ccccc2-c2ccccc21]

Compound 5d ((2R,3S,4S)-1-(tert-butoxycarbonyl)-3-fluoro-4-hydroxypyrrolidine-2-carboxylic acid) (67 mg, 0.36 mmol) was BOC deprotected using a solution of 4 N HCl in Dioxane (2 mL) in DCM (2 mL). Solvents were evaporated and the crude product was dissolved in a mixture of water/dioxane (1:1, 4 mL). Sodium hydrogencarbonate (94 mg, 1.1.6 mmol) was added and the mixture was stirred at room temperature for 10 minutes. 9-Fluorenylmethyl N-succinimidyl carbonate (121 mg, 0.36 mmol) was added in small portions and the mixture was stirred at room temperature overnight). The reaction was cooled to 0° C. and treated with KHSO$_4$ (5%) to pH=3-4. The desired product was extracted with ethyl acetate (3×15 mL) and the organic phase was dried over MgSO4. Solvents were evaporated to obtain the crude product which can be further purified by column chromatography on silica using a gradient from 5% to 20% of MeOH in DCM. (Obtained 106 mg, 79% yield). MS analysis: C20H18FNO, expected 371.4, found 372.4 [M+H$^+$]

$^1$H NMR (500 MHz, CDCl3/MeOD 8:2) mixture of rotamers, δ: 7.73-7.69 (m, 2H), 7.59-7.52 (m, 2H), 7.37-7.31 (m, 2H), 7.29-7.24 (m, 2H), 5.18-5.02 (m, 1H), 4.75-4.61 (m, 1H), 4.38-4.14 (m, 4H), 3.79-3.57 (m, 4H). $^{19}$F-NMR δ: −188.40, −188.58. 13C NMR δ: 172.6, 155.3, 155.2, 143.7, 143.6, 143.5, 143.4, 141.0, 141.0, 140.9, 127.5, 127.5, 126.9, 124.9, 124.9, 119.7, 119.7, 96.2, 95.3, 94.7, 93.8, 71.9, 71.7, 71.2, 71.0, 68.0, 67.7, 66.8, 62.3, 62.1, 62.1, 57.5, 52.4, 52.1, Preparative Compound 5f: (2R,3R,4S)-1-(((9H-fluoren-9-yl)methoxy)carbonyl)-3-fluoro-4-hydroxy-pyrrolidine-2-carboxylic Acid

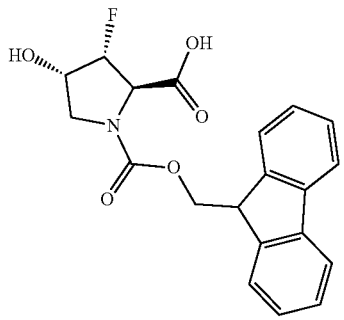 [SMILES: O=C(O)[C@@H]1[C@@H](F)[C@@H](O)CN1C(=O)OCC1c2ccccc2-c2ccccc21]

Compound 5b ((2R,3R,4S)-1-(tert-butoxycarbonyl)-3-fluoro-4-hydroxypyrrolidine-2-carboxylic acid) (67 mg, 0.36 mmol) was BOC deprotected using a solution of 4 N HCl in Dioxane (2 mL) in DCM (2 mL). Solvents were evaporated and the crude product was dissolved in a mixture of water/dioxane (1:1, 4 mL). Sodium hydrogencarbonate (94 mg, 1.1.6 mmol) was added and the mixture was stirred at room temperature for 10 minutes. 9-Fluorenylmethyl N-succinimidyl carbonate (121 mg, 0.36 mmol) was added in small portions and the mixture was stirred at room temperature overnight). The reaction was cooled to 0° C. and treated with KHSO$_4$ (5%) to pH=3-4. The desired product was extracted with ethyl acetate (3×15 mL) and the organic phase was dried over MgSO4. Solvents were evaporated to obtain the crude product which can be further purified by column chromatography on silica using a gradient from 5% to 20% of MeOH in DCM. (Obtained 100 mg, 82% yield). MS analysis: C20H18FNO, expected 371.4, found 372.4 [M+H$^+$]

$^1$H NMR (500 MHz, CDCl3) (mixture of rotamers) δ: 7.76-7.69 (m, 2H), 7.56-7.49 (m, 2H), 7.41-7.27 (m, 4H), 5.21-4.93 (m, 2H), 4.61 (d, J=18.6 Hz, 1H), 4.46-4.37 (m, 3H), 4.25-4.10 (m, 1H), 3.91-3.84 (m, 1H), 3.40 (t, J=9.3 Hz, 1H). 19F NMR δ: −199.35, −201.73. 13C NMR δ: 172.0, 171.9, 170.9, 170.8, 156.4, 154.6, 143.7, 143.6, 141.6, 141.6, 128.2, 127.4, 125.2, 125.2, 120.3, 93.8, 92.3, 70.2, 70.1, 69.7, 69.5, 68.8, 68.2, 64.0, 63.8, 63.6, 63.4, 49.6, 47.2, Preparatory Compounds for the Preparation of Stereoselective F-HYP in Accordance with Scheme 2 Starting Material, Ketone 6:

Starting ketone 6 was prepared in accordance with the method as described in Zanato et al, Org. Biomol. Chem., 2014, 12, 9638.

A solution of methyl (2S, 4R)-4-hydroxypyrrolidine-2-carboxylate hydrochloride (3.0 g, 16.5 mmol) and chlorotrimethylsilane (5.2 mL, 41.3 mmol) in DCM (40 mL) at 0° C. was treated with TEA under stirring (8.0 mL, 57.8 mmol) and allowed to reach r.t. The mixture was stirred at reflux for 1 h, cooled to 0° C., treated with MeOH (1.0 mL) in DCM (4.5 mL), allowed to warm to r.t. for 1 h and then treated with 9-bromo-9-phenylfluorene (6.9 g, 21.45 mmol) and Pb(NO3)2 (4.9 g, 14.9 mmol). The mixture was stirred at r.t. for 96 h, filtered and evaporated. The remaining solid was dissolved in MeOH (54 mL) and citric acid (5.5 g) was added. The solution was vigorously stirred for 1 additional hour, solvent was evaporated under reduce pressure. EtOAc (50 mL) was added and the mixture was carefully washed with saturated NaHCO$_3$ solution. The organic phase was dried over anhydrous MgSO$_4$, then solvent was removed under reduced pressure. The crude product was purified by flash chromatography (Heptane/EtOAc 1:1) to give the Pf protected compound (5.7 g, 90%) as a white foam. $^1$H NMR (400 MHz, CDCl3) δ: 1.79 (ddd, 1H, J=5.6, 8.9, 13.0 Hz), 1.98 (dt, 1H, J=5.6, 12.6 Hz), 2.92 (dd, 1H, J=4.8, 9.9 Hz), 3.24 (s, 3H), 3.29 (dd, 1H, J=5.3, 8.8 Hz), 3.57 (dd, 1H, J=5.3, 10.0 Hz), 4.43-4.58 (m, 1H), 7.16 (td, 1H, J=1.1, 7.5 Hz), 7.21-7.35 (m, 6H), 7.43 (td, 1H, J=1.1, 7.5 Hz), 7.50-7.59 (m, 3H), 7.65 (dd, 1H, J=0.7, 6.8 Hz), 7.74 (dd, 1H, J=0.8, 6.8 Hz); 13C NMR (100 MHz, CDCl3) δ: 40.0, 51.3, 56.8, 59.3, 70.4, 76.1, 119.8, 120.1, 126.4, 127.1, 127.2, 127.3 (×2), 127.6, 128.3 (×2), 128.4, 128.8, 139.9, 141.5, 142.7, 146.1, 147.2, 175.8.

Preparative Compound 7: Methyl (2R,3S)-3-fluoro-4-oxo-1-(9-phenyl-9H-fluoren-9-yl)pyrrolidine-2-carboxylate

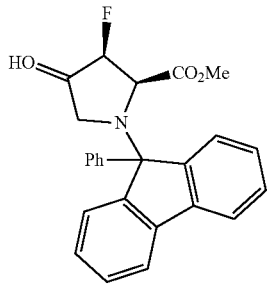 [SMILES: COC(=O)[C@@H]1[C@H](F)C(=O)CN1C1(c2ccccc2)c2ccccc2-c2ccccc21]

A solution of starting ketone 6 (600 mg, 1.57 mmol) in DCM (15 mL) was cooled to −30° C., and TEA (700 μL, 4.70 mmol) was added dropwise. Trimethylsilyltriflate (TMSOTf) (570 μL, 3.13 mmol) was then added dropwise at −30° C. The mixture was stirred for 2 hr and kept below −10° C. The solvent was then removed under vacuum and pentane (25 mL) was added. The mixture was poured into a saturated solution of NaHCO$_3$ (50 mL) and was vigorously shaken. The organic layer was separated, washed with brine, then dried over anhydrous MgSO$_4$. The solvent (volatiles) was removed under reduced pressure to obtain a light yellow oil, corresponding to a non-isolated intermediate trimethylsilylenolate, which was dissolved in acetonitrile (30 mL) and cooled to −40° C. Selectfluor (834 mg, 2.35 mmol) was added in one portion and the mixture was allowed to reach 10° C. overnight. TLC analysis (EtOAc/Heptane 2:8) showed complete conversion of the starting material. A saturated solution of NH$_4$Cl was added (30 ML), the resulting mixture was vigorously shaken and the organic layer was then separated. The aqueous layer was extracted with EtOAc (2×30 mL) and the organic phase was washed with brine, then dried over MgSO$_4$. Volatiles were removed under reduced pressure to obtain the crude product as yellow oil, which was purified by FCC (EtOAc/Heptane 1:9) to obtain the desired fluoroketone (346 mg, 55% yield) as a white solid. MS analysis do not show any informative result as the only ion detected corresponded to the 9-phenylfluorenyl carbocation m/z=241.1.

$^1$H-NMR (CDCl$_3$) δ: 7.76 (d, J$_{H-H}$=7.6 Hz, 1H), 7.71 (d, J$_{H-H}$=7.6 Hz, 1H), 7.46-7.325 (m, 11H), 5.07 (dd, J=H—F=51.0 Hz, J$_{H-H}$=7.9 Hz, 1H), 4.03 (d, J=8.1 Hz, 1H), 3.98 (d, J$_{H-H}$=17.9 Hz, 1H), 3.63 (d, J$_{H-H}$=17.9 Hz, 1H), 3.19 (s, 3H). 19F-NMR −206.52. $^{13}$C-NMR δ: 205.4 (d, J$_{C-F}$=12.7 Hz), 169.3, 124.2, 144.7, 141.2, 140.6, 139.9, 129.3, 129.2, 128.8, 123.3, 128.0, 127.7, 126.8, 126.6, 125.1, 120.5, 120.4, 89.1 (d, J$_{C-F}$=205.4 Hz), 75.1, 60.0 (d, J$_{C-F}$=20.3. Hz), 51.8 (d, J$_{C-F}$=22.8 Hz).

Preparative Compound 8: Methyl (2R,3S,4R)-3-fluoro-4-hydroxy-1-(9-phenyl-9H-fluoren-9-yl)pyrrolidine-2-carboxylate

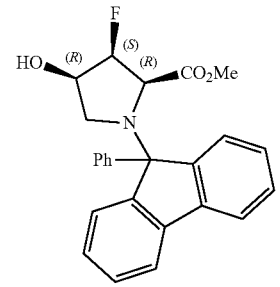

Preparative fluoroketone compound 7 (638 mg, 1.59 mmol) was dissolved in THF/EtOH 1:1 (20 mL) at 0° C. NaBH$_4$ (63 mg, 1.67 mmol) was added portion-wise and the reaction mixture was stirred for 1 hour at 0 C. TLC analysis (EtOAc/Heptane 3:7) showed complete conversion of the starting material. The reaction mixture was concentrated under vacuum, EtOAc was added (30 mL) and a solution of NaHSO$_4$ (5%) was added dropwise until a pH of 3 to 4 was obtained. The acidified mixture was washed with brine (10 mL), and the organic phase was dried over anhydrous MgSO$_4$. Volatiles were removed under reduced pressure to obtain the title compound as a white solid in quantitative yield.

$^1$H-NMR (CDCl$_3$) δ: 7.79 (d, J$_{H-H}$=7.6 Hz, 1H), 7.65 (d, J$_{H-H}$=7.5 Hz, 1H), 7.55-7.53 (m, 2H), 7.49-7.48 (m 1H), 7.44-7.42 (m, 1H), 7.36-7.33 (m, 1H), 7.30-7.26 (m, 5H), 7.15-7.12 (m, 1H), 4.76-4.64 (m, 1H), 4.15 (br s, 2H), 3.45 (dd, J$_{H-H}$=10.6 Hz, J$_{H-H}$=5.0 Hz, 1H), 3.39 (s, 3H), 3.27 (dd, J$_{H-F}$=8.8 Hz, J$_{H-H}$=6.3 Hz, 1H), 3.05 (d, J$_{H-H}$=10.6 Hz, 1H). $^{19}$F-NMR δ: −205.26. $^{13}$C-NMR δ: 173.8 (d, J$_{C-F}$=4.6 Hz), 147.4, 144.6, 141.9, 140.8, 139.2, 129.1, 128.7, 128.6, 127.9, 127.7, 127.4, 126.0, 126.3, 120.4, 120.1, 90.7 (d, J$_{C-F}$=197.6 Hz), 75.6, 70.8 (d, J$_{C-F}$=16.1 Hz), 60.8 (d, J$_{C-F}$=21.8 Hz), 52.9 (d, J c$_F$=3.5 Hz), 52.2, 29.7.

Preparative Compound 10: Methyl (2R,3S,4S)-3-fluoro-4-((4-nitrobenzoyl)oxy)-1-(9-phenyl-9H-fluoren-9-yl)pyrrolidine-2-carboxylate

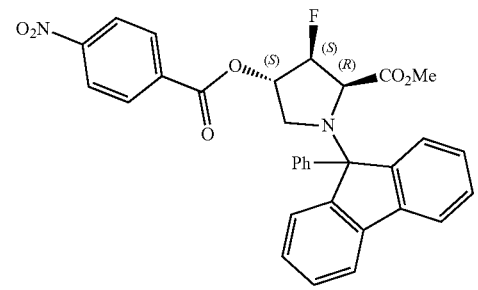

Preparative compound 10 was prepared from preparative compound 8 according to the general procedure for the Mitsunobu inversion as detailed hereinbefore. Compound 10 was obtained in 87% yield.

$^1$H-NMR (CDCl$_3$) δ: 8.30-8.28 (m, 2H), 8.14-8.12 (m, 2H), 7.74-7.73 (m, 1H), 7.69-7.68 (m, 1H), 7.52-7.50 (m, 2H), 7.40-7.38 (m, 4H), 7.28-7.18 (m, 5H), 5.75-5.68 (m, 1H), 5.06 (ddd, J H-F+53.5 Hz, $J_{H-H}$=8.0 Hz, $J_{H-H}$=5.5 Hz, 1H), 4.04 (dd, $J_{H-F}$=10.2 Hz, $J_{H-H}$=6.8 Hz, 1H), 3.67 (dd, $J_{H-F}$=7.9 Hz, $J_{H-H}$=6.7 Hz, 1H), 3.36 (s, 3H), 3.08 (dd, $J_{H-H}$=10.5 Hz, $J_{H-H}$=5.6 Hz, 1H). $^{19}$F-NMR δ: −196.44. $^{13}$C-NMR δ: 170.3 (d, $J_{C-F}$=4.5 Hz), 163.9, 150.8, 146.1, 145.6, 141.1, 140.1, 134.7, 130.9, 129.0, 128.6, 127.9, 127.8, 127.4, 127.1, 126.0, 123.6, 120.3, 120.1, 93.3 (d, $J_{C-F}$=195.3 Hz), 75.4, 61.9 (d, $J_{C-F}$=21.7 Hz), 51.7, 49.7 (d, $J_{C-F}$=5.6 Hz).

Preparative Compound 11: Methyl (2R,3S,4S)-3-fluoro-4-hydroxy-1-(9-phenyl-9H-fluoren-9-yl)pyrrolidine-2-carboxylate

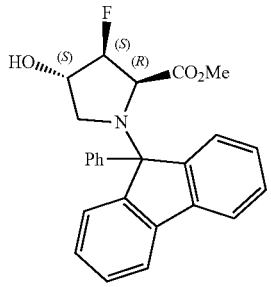

To a stirred solution of the 4-nitrobenzoate ester of preparative compound 10 (217 mg, 0.391 mmol) in THF (8 mL) at 0° C., LiOH (19 mg, 0.469 mmol) dissolved in water (2 mL) was added dropwise. The mixture was stirred at 0° C. for 2 hours. TLC analysis (EtOAc/Heptane 3:7) showed complete conversion of the starting material. The reaction mixture was concentrated under vacuum, water (5 mL) was added and the mixture was extracted with EtOAc (3×15 mL). The organic phase was washed with brine (5 mL), dried over anhydrous MgSO$_4$ and the volatiles were removed under reduced pressure. The crude product was purified by FCC (EtOAc/Heptane 1:9) to obtain the title compound as white foam in quantitative yield.

$^1$H-NMR (CDCl$_3$) δ: 7.75 (d, $J_{H-H}$=7.5 Hz, 1H), 7.65 (d, $J_{H-H}$=7.5 Hz, 1H), 7.54-7.52 (m, 2H), 7.49 (d, $J_{H-H}$=7.6 Hz, 1H), 7.46-7.43 (m, 1H), 7.35-7.23 (m, 6H), 7.18-7.15 (m, 1H), 4.71-4.53 (m, 2H), 3.61-3.58 (m, 1H), 3.47-3.44 (m, 1H), 3.38 (s, 3H), 2.29-2.84 (m, 1H). $^{19}$F-NMR δ: −197.63.

Preparative Compound 9a: (2R,3S,4R)-3-fluoro-4-hydroxy-2-(methoxycarbonyl)pyrrolidin-1-ium 2,2,2-trifluoroacetate

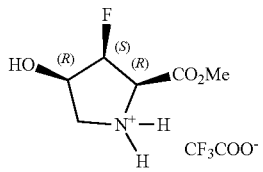

Preparative compound 8 (100 mg, 0.248 mmol) was dissolved in DCM (10 mL). Triisopropylsilane (TIPS) (760 μL) and trifluoroacetic acid (TFA) (500 μL) were added, and the resultant yellow mixture was left to react at room temperature for 2 h. Water 5 mL was added, the mixture was vigorously shaken and the aqueous phase was separated, washed with 2 mL of Et$_2$O and freeze-dried to afford the title compound in 80% yield.

$^1$H-NMR (D$_2$O) δ: 5.46-5.34 (m, 1H), 4.83 (dd, J H-F=32.1 Hz, $J_{H-H}$=2.9 Hz, 1H), 4.70-4.61 (m, 1H), 3.85 (s, 3H), 3.76-3.72 (m, 1H), 3.32-3.28 (m, 1H). $^{19}$F-NMR δ: −75.56 (3F), −208.8 (1F).

Preparative Compound 9b: (2R,3S,4S)-3-fluoro-4-hydroxy-2-(methoxycarbonyl)pyrrolidin-1-ium 2,2,2-trifluoroacetate

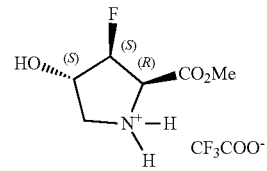

Prepared as described for compound 9a from preparative compound 11 in 82% yield. 1H-NMR (D2O) δ: 5.38 (d, J H—F=48.9 Hz, 1H), 4.95 (dd, J H—F=33.3 Hz, $J_{H-H}$=2.3 Hz, 1H), 4.67 (br s, 1H), 3.86 (s, 3H), 3.75-3.72 (m, 1H), 3.47 (d, $J_{H-H}$=1301 Hz, 1H). $^{19}$F-NMR δ: −75.56 (3F), −192.27 (1F). $^{13}$C-NMR δ: 165.9 (d, $J_{C-F}$=5.6 Hz), 162.3 (d, $J_{C-F}$=35.5 Hz), 116.3 (d, $J_{C-F}$=291.7 Hz), 94.4 (d, $J_{C-F}$=185.6 Hz), 71.6 (d, $J_{C-F}$=27.2 Hz), 62.7 (d, $J_{C-F}$=21.3 Hz), 54.1, 51.4.

Scheme 3—General Procedure for Synthesis of Compounds of Formula I, IA or IB (A-Groups)

Any compounds of formula I as defined herein can be prepared in accordance with the general methodology in Scheme 3 by selection of the appropriate reagents at the following stages: choice of C- or N-5 membered ring and selection of the desired $R^{2a}$, $R^{2b}$, $R^x$, substituents thereon as the start-point; selection of the desired $R^3$, $R^4$ and $R^5$ groups to determine the appropriate reagent for utility in stage (i); selection of the desired Y group ($Y_A$, $Y_B$, $Y_C$) to determine the appropriate reagents at stages (ii) and (iii); and finally selection of the desired $R^1$ group in the final stages to provide the compound of formula I, IA or IB.

Scheme 3

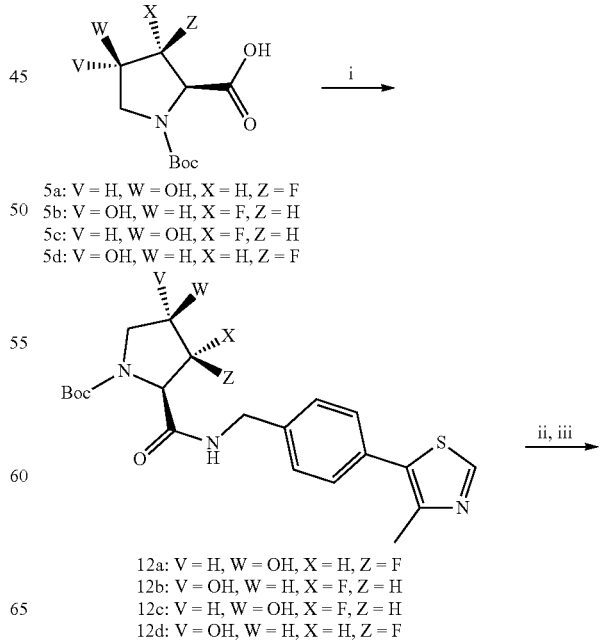

5a: V = H, W = OH, X = H, Z = F
5b: V = OH, W = H, X = F, Z = H
5c: V = H, W = OH, X = F, Z = H
5d: V = OH, W = H, X = H, Z = F

12a: V = H, W = OH, X = H, Z = F
12b: V = OH, W = H, X = F, Z = H
12c: V = H, W = OH, X = F, Z = H
12d: V = OH, W = H, X = H, Z = F

Preparation of Compounds of General Formula I, IA or IB in Accordance with Scheme 3

Preparative Compound 12b: tert-butyl (2R,3R,4S)-3-fluoro-4-hydroxy-2-((4-(4-methylthiazol-5-yl)benzyl)carbamoyl)pyrrolidine-1-carboxylate

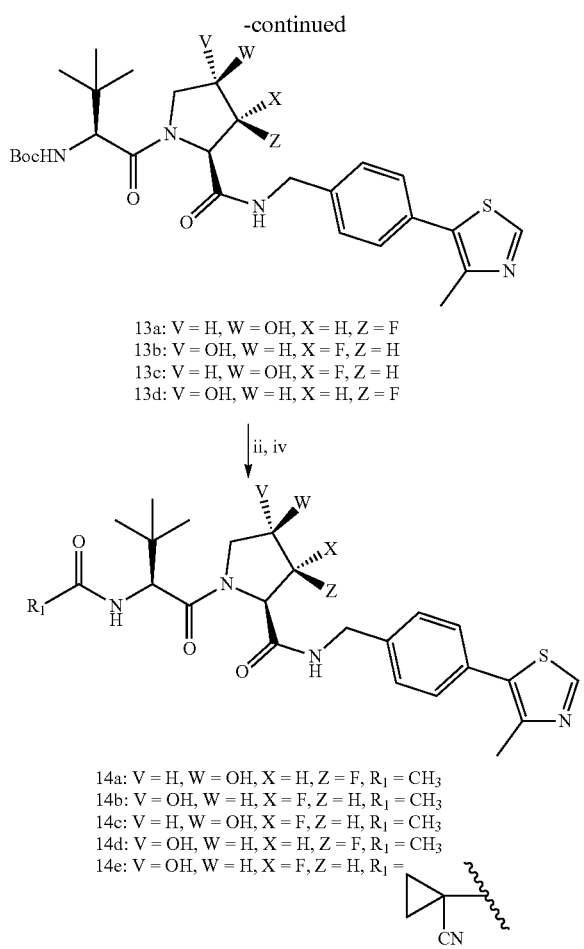

13a: V = H, W = OH, X = H, Z = F
13b: V = OH, W = H, X = F, Z = H
13c: V = H, W = OH, X = F, Z = H
13d: V = OH, W = H, X = H, Z = F ii, iv

14a: V = H, W = OH, X = H, Z = F, R₁ = CH₃
14b: V = OH, W = H, X = F, Z = H, R₁ = CH₃
14c: V = H, W = OH, X = F, Z = H, R₁ = CH₃
14d: V = OH, W = H, X = H, Z = F, R₁ = CH₃
14e: V = OH, W = H, X = F, Z = H, R₁ =

The conditions used for exemplary preparations in Scheme 3 are as follows: (i) (4-(4-methylthiazol-5-yl)phenyl)methanamine, DIPEA, HATU, HOAT in DMF, rt; (ii) HCl 2M in Dioxane/DCM 1:1, rt; (iii) Boc-L-tert- leucine, DIPEA, HATU, HOAT, in DMF, rt; (iv) acetic anhydride, TEA, in DCM, 0° C. for 14a-d,or 1-cyanocyclopropane-1-carboxylic acid, DIPEA, HATU, HOAT, in DMF, rt for 14e.

As will be appreciated by the skilled chemist, using the general procedures indicated in Scheme 3, and via selection of the appropriate starting materials (5a-d) and using the methodology provided for the preparation of Boc-protected compounds (13a-d) and compounds of formula IA (14a-e) any Boc-protected amine suitable for use in the preparation of compounds of formula I, or any compound of formula IA or IB as defined herein can be prepared.

In particular in step (i) the use of alternative starting materials, provides alternative final compounds having different $R^{2a}$ and/or $R^{2b}$ groups, to that provided in the above examples, or compounds where X=C, as opposed to N as illustrated in the above examples. Exemplary commercially available materials suitable for such use include: 2-trifluoromethyl; 2-fluoroproline; 2,2-difluoroproline; and 2-aminoproline. As will also be appreciated further starting reagents suitable for use in step (i) can be readily prepared from hydroxyproline, or from one or other commercially available alternatives, for example, 2-aminoproline (where $R^{2a}$ is —NH₂ and $R^{2b}$ is H) in the final compound (where X=N) can be made starting from hydroxyproline via suitable modification of the synthetic routes provided herein for synthesis of F-HYP starting materials.

A general method for Boc-deprotection is provided in Scheme 7 herein.

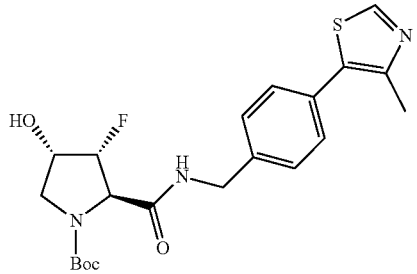 [SMILES: Cc1ncsc1-c1ccc(CNC(=O)[C@@H]2[C@@H](F)[C@@H](O)CN2C(=O)OC(C)(C)C)cc1]

To a solution of (4-(4-methylthiazol-5-yl)phenyl)methanamine (32.7 mg, 0.160 mmol) in DMF (1 mL), a mixture of N-Boc-fluoro-hydroxyproline 5b (40.0 mg, 0.160 mmol), HATU (61.0 mg, 0.106 mmol), 1-hydroxy-7-azabenzotriazole (HOAT) (22.0 mg, 0.160 mmol) and N,N-Diisopropylethylamine, also called Hünig's base (DIPEA) (85 μL, 0.480 mmol) in DMF (0.5 mL) was added dropwise under stirring at r.t. After one hour, HPLC analysis showed complete conversion of the starting material and formation of the desired product (METHOD 1, rt=1.451 min, m/z=436.2, [M+H]⁺). The reaction was diluted with DCM (10 mL), washed with water (2 mL), the organic phase was extracted and then dried over anhydrous MgSO₄ and the solvents were then removed under vacuum. Purification by preparative HPLC (acidic method) afforded the title compound as a white solid (60 mg) in 86% yield.

¹H-NMR (MeOD) δ: 9.10-9.07 (m, 1H), 7.47-7.46 (m, 4H), 4.97-4.85 (overlapped with signal of residual water in the solvent, m, 1H), 4.52-4.33 (m, 4H), 3.81-3.76 (m, 1H), 2.51 (s, 3H), 1.49* (s, 9H), 1.33 (s, 9H). ¹⁹F-NMR δ: −198.50, −199.21*.

The starting material, 4-(4-methylthiazol-5-yl)phenyl) methanamine was prepared in accordance with the methodology in unpublished international patent application PCT/GB2016/050691, preparative compound (2).

Preparative Compound 12d: tert-butyl (2R,3S,4S)-3-fluoro-4-hydroxy-2-((4-(4-methylthiazol-5-yl)benzyl)carbamoyl)pyrrolidine-1-carboxylate

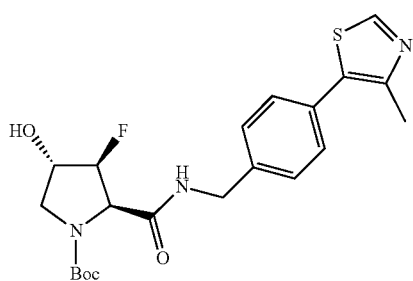 [SMILES: Cc1ncsc1-c1ccc(CNC(=O)[C@@H]2[C@H](F)[C@@H](O)CN2C(=O)OC(C)(C)C)cc1]

Preparative compound 12d, was obtained in accordance with the methodology as described for preparative compound 12b, and starting from compound 5d, HPLC analysis (METHOD 2) rt=3.007 min, m/z=436.2, [M+H]⁺. (82% yield, white solid). ¹H-NMR (CD3OD) δ: 8.79 (s, 1H), 7.48-7.44 (m, 4H), 5.12-5.01 (m, 1H), 4.63-4.39 (m, 3H), 4.34-4.32 (m, 1H), 3.76-3.62 (m, 2H), 2.49 (s, 3H), 1.50* (s, 9H), 1.34 (s, 9H). $^{19}$F-NMR δ: −193.81, −194.03*

Preparative Compound 13b: tert-butyl ((S)-1-((2R, 3R, 4S)-3-fluoro-4-hydroxy-2-((4-(4-methylthiazol-5-yl)benzyl)carbamoyl)pyrrolidin-1-yl)-3,3-dimethyl-1-oxobutan-2-yl)carbamate

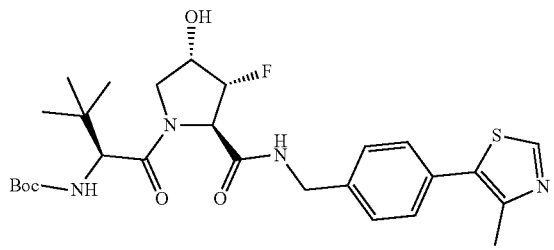 [SMILES: Cc1ncsc1-c1ccc(CNC(=O)[C@@H]2[C@@H](F)[C@@H](O)CN2C(=O)[C@@H](NC(=O)OC(C)(C)C)C(C)(C)C)cc1]

To a solution of preparative compound 12b (22.0 mg, 0.05056 mmol) in DCM/MeOH 9:1 (1.0 mL), HCl in dioxane (4M, 1.0 mL) was added and mixture was stirred for 4 hours at room temperature. The volatiles were removed under vacuum, and the residue was dissolved in water and freeze-dried to afford the deprotected amine as the corresponding hydrochloride salt form in quantitative yield as a light yellow powder. This salt was used without any further purification, and was suspended in DMF (1 mL) and DIPEA (22 µL, 0.126 mmol) was added. To the resulting solution, a mixture of (S)-2-((tert-butoxycarbonyl)amino)-3,3-dimethylbutanoic acid (11.7 mg, 0.0506 mmol), HATU (19.0 mg, 0.0506 mmol), HOAT (6.9 mg, 0.05056 mmol) and DIPEA (22 µL, 0.126 mmol) in DMF (0.5 mL) was added under stirring at r.t. After 3 hours, HPLC analysis (METHOD 1, rt=1.646 min, m/z=493.2, [M-tBu+H]$^+$) showed complete conversion of the starting material and the formation of the desired product. DCM (10 ml) was added and the mixture was washed with water (1 mL) and NaHSO$_4$ solution (5%, 1 mL). The organic layer was dried over anhydrous MgSO$_4$ and the solvents were removed under reduced pressure. The crude product was obtained as a yellow wax (25 mg, 90% yield) and was used directly in the next step without any further purification.

$^1$H NMR (500 MHz, MeOD) δ: 8.94 (s, 1H), 7.48-7.42 (m, 4H), 5.05-4.92 (m, 1H), 4.71-4.63 (m, 1H), 4.59-4.47 (m, 2H), 4.41-4.35 (m, 1H), 4.30 (s, 1H), 4.08-4.03 (m, 1H), 3.79-3.72 (m, 1H), 2.49 (s, 3H), 1.46* (s, 9H), 1.02 (s, 9H). $^{19}$F-NMR δ: −200.36.

Preparative Compound 13d: tert-butyl ((S)-1-((2R, 3S,4S)-3-fluoro-4-hydroxy-2-((4-(4-methylthiazol-5-yl)benzyl)carbamoyl)pyrrolidin-1-yl)-3,3-dimethyl-1-oxobutan-2-yl)carbamate

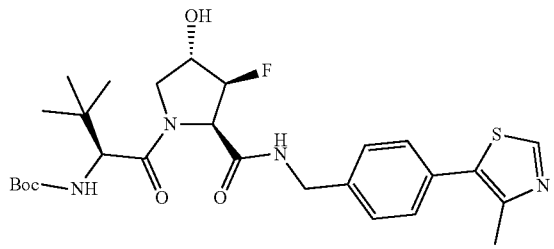 [SMILES: Cc1ncsc1-c1ccc(CNC(=O)[C@@H]2[C@H](F)[C@@H](O)CN2C(=O)[C@@H](NC(=O)OC(C)(C)C)C(C)(C)C)cc1]

Preparative compound 13d, was obtained in accordance with the methodology as described for preparative compound 13b, and starting from preparative compound 12d. The crude product was obtained as a yellow wax in 88% yield. HPLC analysis (METHOD 1): rt=1.639 min, m/z=493.2, [M M-tBu+H]$^+$. $^1$H-NMR (MeOD) δ: 8.93 (s, 1H), 8.63-8.61 (m, 1H), 7.47-7.42 (m, 4H), 5.14-5.02 (m, 1H), 4.79 (dd, J H—F=26.0 Hz, J H—H=5.3 Hz, 1H), 4.54-4.43 (m, 3H), 4.30 (s, 1H), 3.97-3.91 (m, 2H), 2.49 (s, 3H), 1.44 (cis BOC rotmer, s, 9H), 1.06 (s, 9H). $^{19}$F-NMR δ: −193.39.

Preparative Compound 14b: tert-butyl ((S)-1-((2R, 3R,4S)-3-fluoro-4-hydroxy-2-((4-(4-methylthiazol-5-yl)benzyl)carbamoyl)pyrrolidin-1-yl)-3,3-dimethyl-1-oxobutan-2-yl)carbamate

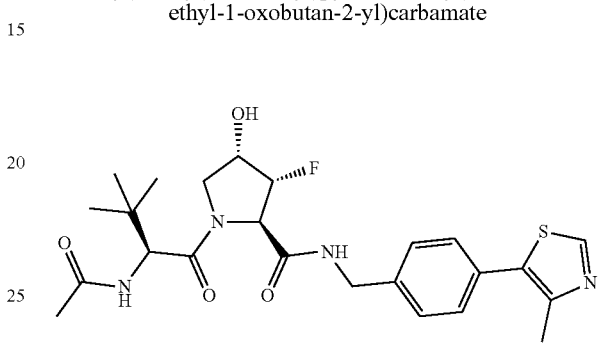

To a solution of preparative compound 13b (25.0 mg, 0.0455 mmol) in DCM/MeOH 9:1 (1.0 mL), HCl in dioxane (4M, 1.0 mL) was added and the resultant mixture was stirred for 4 hours at room temperature. The volatiles were removed under vacuum, the residue was dissolved in water and freeze-dried to afford the deprotected amine as a light yellow powder in quantitative yield in the form of the corresponding hydrochloride salt. This salt was used directly without any further purification and was suspended in DCM (1 mL), TEA (12.7 µL, 0.091 mmol) was added, followed by acetic anhydride (4.3 µL, 0.0455 mmol) was added at 0° C., and the resultant mixture was stirred at 0° C. for two hours. HPLC analysis showed complete conversion of the starting material and the formation of the desired product (METHOD 2 rt=2.819 min, m/z=491.2, [M+H]$^+$). The volatile solvents were removed and the crude was purified by preparative HPLC to obtain the title compound as a white solid (17.0 mg, 75% yield).

$^1$H NMR (500 MHz, MeOD) δ: 8.89 (s, 1H), 7.47-7.41 (m, 4H), 5.03-4.91 (m, 1H), 4.65 (dd, J H—F=21.4 Hz, J H—H=2.8 Hz, 1H), 4.60 (s, 1H), 4.58-4.35 (m, 3H), 4.06-4.03 (m, 1H), 3.79-3.75 (m, 1H), 2.48 (s, 3H), 2.01 (s, 3H), 1.04 (s, 9H). $^{19}$F-NMR δ: −199.02 (cis rotmer) −200.31.

Preparative Compound 14d: tert-butyl ((S)-1-((2R, 3S,4S)-3-fluoro-4-hydroxy-2-((4-(4-methylthiazol-5-yl)benzyl)carbamoyl)pyrrolidin-1-yl)-3,3-dimethyl-1-oxobutan-2-yl)carbamate

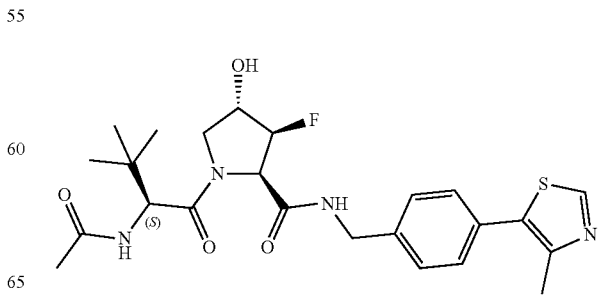

Preparative compound 14d, was obtained in accordance with the methodology as described for preparative compound 14b, and starting from preparative compound 13d. The product was obtained in 76% yield as a white solid. HPLC analysis (METHOD 2) rt=2.901 min, m/z=491.2, [M+H]$^+$. $^1$H NMR (500 MHz, MeOD) δ: 8.88 (s, 1H), 7.47-7.41 (m, 4H), 5.14-5.00 (m, 1H), 4.77 (dd, J H—F=26.15 Hz, J H—H=5.2 Hz, 1H), 4.63 (s, 1H), 4.55-4.32 (m, 3H), 4.00-3.91 (m, 2H), 2.48 (s, 3H), 2.01 (s, 3H), 1.08 (s, 9H). $^{19}$F-NMR δ: −193.12.

Preparative Compound 14e: 2R,3R,4S)-1-((S)-2-(1-cyanocyclopropane-1-carboxamido)-3,3-dimethylbutanoyl)-3-fluoro-4-hydroxy-N-(4-(4-methylthiazol-5-yl)benzyl)pyrrolidine-2-carboxamide

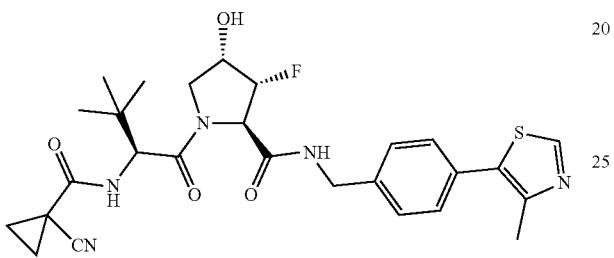

To a solution of preparative compound 13d (10.0 mg, 0.0206 mmol) in DMF (0.3 mL), DIPEA (8.8 µL, 0.0515 mmol) was added under stirring at r.t. To the resulting solution, a mixture of 1-cyanocyclopropane-1-carboxylic acid (2.3 mg, 0.0206 mmol), HATU (8.0 mg, 0.0206 mmol), HOAT (2.8 mg, 0.0206 mmol) and DIPEA (8.8 µL, 0.0515 mmol) in DMF (0.3 mL) was added dropwise under stirring at r.t. After 2 hours, HPLC analysis showed complete conversion of the starting material and the formation of the expected product (METHOD 1, rt=1.532 min, m/z=542.2, [M+H]$^+$). DCM (10 ml) was added and the mixture was washed with water (1 mL). The organic layer was dried over anhydrous MgSO$_4$ and the solvents were removed under reduced pressure. The crude was purified by preparative HPLC to obtain the title compound as a white solid (8 mg, 72% yield). $^1$H NMR (400 MHz, MeOD) δ: 8.90 (s, 1H), 7.49-7.44 (m, 4H), 5.08-4.93 (m, 1H), 4.67 (dd, J$_{H-F}$=20.9, dd, J$_{H-F}$=3.2 Hz, 1H), 4.66 (s, 1H), 4.61-4.35 (m, 3H), 4.04 (dd, J=6.0, 10.2 Hz, 1H), 3.75-3.69 (m, 1H), 2.50 (s, 3H), 1.70-1.55 (m, 4H), 1.07 (s, 9H). $^{19}$F-NMR δ: −198.8*, −200.71.

Scheme 4—General Process for Coupling A to Az-L to Provide Azide of Structure Az-L-A Scheme 4 illustrates the synthetic methodology for the provision of azide intermediate compounds of structure Az-L-A suitable for use in the preparation of F-HYP containing PROTACs of structure A-L-B. As outlined in Scheme 4, the starting protected amines, for example preparative compounds (13a-d), are firstly de-protected to furnish amine intermediates, for example preparative compounds (15a-d) by using HCl in dioxane, in stage (i), with subsequent treatment with the desired linker, for example Az-PEG-linkers (A6) or (A7) in the presence of HATU and HOAT and the pH being adjusted to >9 by addition of DIPEA. After stirring for 4 h at 25° C. the reaction mixture was extracted with water. The organic phase was dried over Magnesium sulfate and evaporated to dryness. The crude product was purified by flash column chromatography using a gradient of 0%-6% of methanol in dichloromethane to furnish the desired intermediate azide of structure Az-L-A.

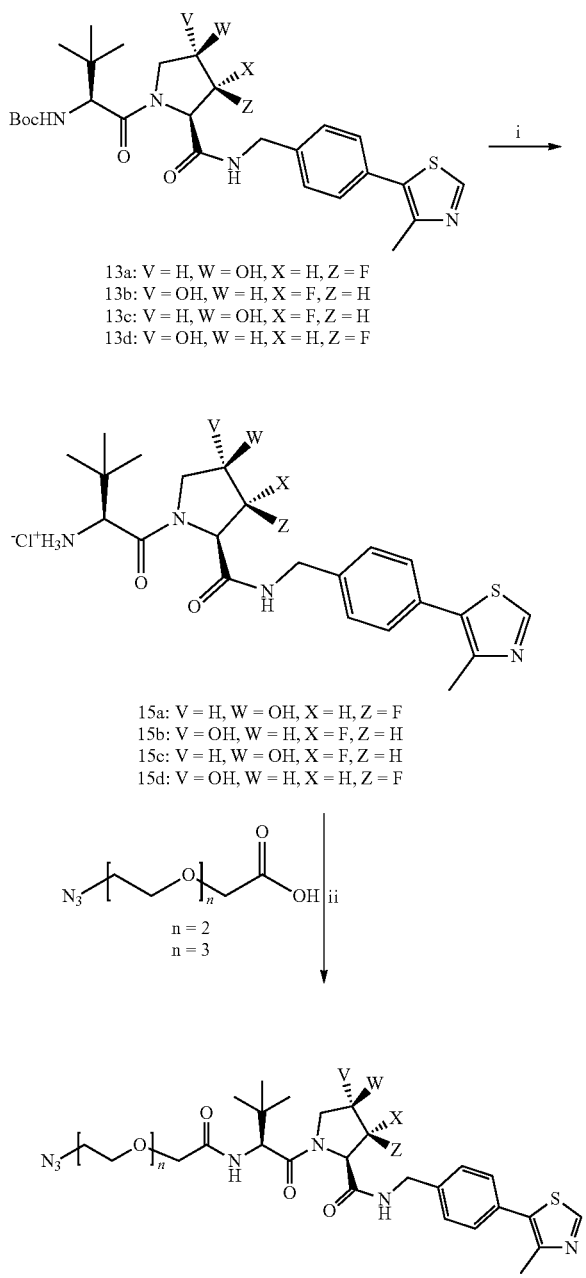

13a: V = H, W = OH, X = H, Z = F
13b: V = OH, W = H, X = F, Z = H
13c: V = H, W = OH, X = F, Z = H
13d: V = OH, W = H, X = H, Z = F

15a: V = H, W = OH, X = H, Z = F
15b: V = OH, W = H, X = F, Z = H
15c: V = H, W = OH, X = F, Z = H
15d: V = OH, W = H, X = H, Z = F n = 2
n = 3

16a: V = H, W = OH, X = H, Z = F, n = 3
16b: V = OH, W = H, X = F, Z = H, n = 3
16c: V = H, W = OH, X = F, Z = H, n = 3
16d: V = OH, W = H, X = H, Z = F, n = 3
16e: V = OH, W = H, X = H, Z = F, n = 2

The conditions used for exemplary preparation in Scheme 4 are as follows: (i) HCl 2M in Dioxane/DCM 1:1, rt; (ii) linker—COOH, DIPEA, HATU, HOAT, in DMF, rt.

Preparatory Compounds for Preparing Intermediate Azides Az-L-A in Accordance with Scheme 4

Preparative Compound 16d: (2R,3S,4S)-1-((S)-14-azido-2-(tert-butyl)-4-oxo-6,9,12-trioxa-3-azatetradecanol)-3-fluoro-4-hydroxy-N-(4-(4-methylthiazol-5-yl)benzyl)pyrrolidine-2-carboxamide

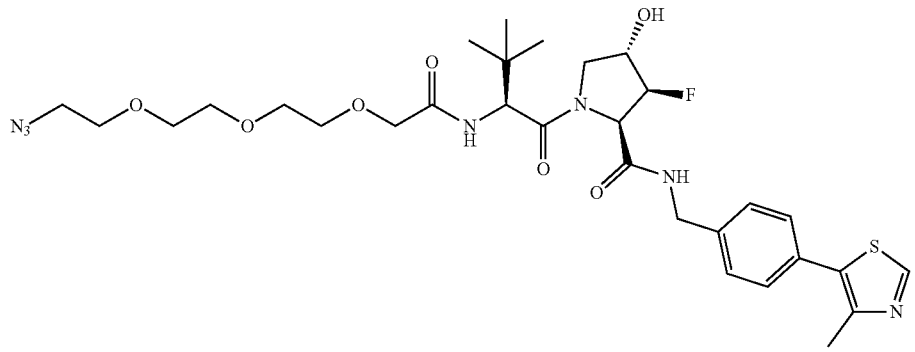 [SMILES: Cc1ncsc1-c1ccc(CNC(=O)[C@@H]2[C@H](F)[C@@H](O)CN2C(=O)[C@@H](NC(=O)COCCOCCOCCN=[N+]=[N-])C(C)(C)C)cc1]

To a solution of preparative compound 13d (15 mg, 0.034 mmol) in DCM (0.5 mL), HCl in dioxane (4M, 0.5 mL) was added. Methanol (0.2 mL) was added to solubilize the precipitate which formed after few minutes. After 2 hours, HPLC analysis showed complete conversion of the starting material and formation of the desired free amine 15d (METHOD 2 rt=2.403 min, m/z=449.2, [M+H]$^+$). The volatile components were removed under reduced pressure and the crude product was suspended in DMF (1 mL). DIPEA (10 µL, 0.051 mmol) was added, followed by a mixture of 2-(2-(2-(2-azidoethoxy)ethoxy)ethoxy)acetic acid (A6) (8.0 mg, 0.034 mmol), HATU (13.0 mg, 0.034 mmol), HOAT (4.6 mg, 0.034 mmol) and DIPEA (10 µL, 0.051 mmol). The resulting mixture was stirred at room temperature for one hour. HPLC analysis showed complete conversion of the starting material and formation of the desired product (METHOD 2 rt=3.241 min, m/z=664.3, [M+H]$^+$). The crude mixture was diluted with EtOAc (10 mL), washed with brine (2 mL) and solvents were removed under reduced pressure. The crude product was purified by preparative HPLC to obtain the desired compound as transparent oil (11.2 mg, 50% yield).

Preparative Compound 16e: (2R,3S,4S)-1-((S)-2-(2-(2-(2-azidoethoxy)ethoxy)acetamido)-3,3-dimethylbutanoyl)-3-fluoro-4-hydroxy-N-(4-(4-methylthiazol-5-yl)benzyl)pyrrolidine-2-carboxamide

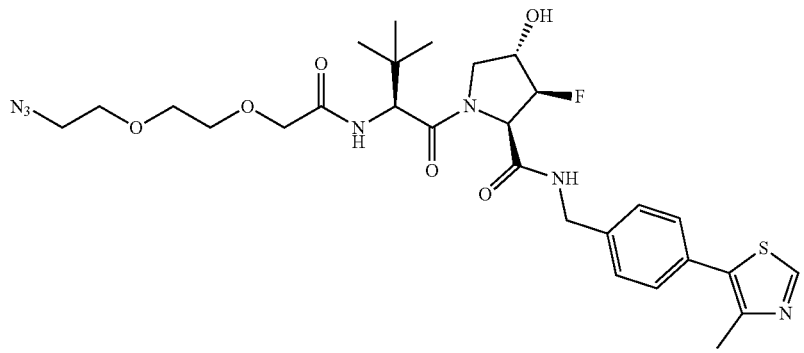 [SMILES: Cc1ncsc1-c1ccc(CNC(=O)[C@@H]2[C@H](F)[C@@H](O)CN2C(=O)[C@@H](NC(=O)COCCOCCN=[N+]=[N-])C(C)(C)C)cc1]

Preparative compound 16e, was obtained in accordance with the methodology as described for preparative compound 16d, and starting from preparative compound 15e. The product was obtained in 55% yield, transparent oil. HPLC analysis (METHOD 2) rt=3.226 min, m/z=620.3, [M+H]$^+$.

Scheme 5—General Process for Making A-~L-B PROTACs from De-Protected Intermediates Scheme 5 illustrates the process for the preparation of PROTACs of structure A-L-B from preparative intermediate azide compounds of structure Az-L-A. The starting azide, of structure Az-L-A, such as for example preparatory intermediate compound (16a) (40 μmol) was dissolved in methanol (5 ml). A catalytic amount of palladium on charcoal (10 wt %, dry) was added and the reaction mixture was then stirred under an atmosphere of hydrogen gas for about 1 h at 25° C. The reaction mixture was then filtered through a syringe filter and the resulting solution evaporated to dryness to obtain the desired intermediate amine, corresponding to the starting azide was then linked to the desired B-group without further purification. The intermediate amine, structure NH$_2$-L-A in this general example, the amine equivalent of intermediate compound (17a) and the desired B-group, in this general example suitable B-groups include the: free acid of JQ1 (11.4 mg, 25 μmol, 1 eq.), or I-BET726 (10.9 mg, 25 μmol, 1 eq.), or free acid of I-BET762 (9.92 mg, 25 μmol, 1 eq.), were then dissolved in DMF (0.5 ml) CM (2 ml). HATU (14.3 mg, 37.5 μmol, 1.5 eq.) was then added and the pH of the resultant mixture was adjusted to >9 by adding DIPEA (17.5 μl, 100 μmol, 4 eq.). After stirring the reaction mixture at 25° C. for 3 h the solvent was removed in vacuum. Purification of the crude product was achieved by preparative HPLC as described in the general information in order to furnish the desired PROTAC.

For the avoidance of doubt, such intermediate amines are prepared from the corresponding de-protected azides by any suitable methods, and in particular, via reduction over palladium, with the resultant amines being utilized directly without further purification.

Any PROTAC compound of structure A-L-B can be prepared in accordance with the general procedure outlined starting from intermediate compounds (13), by use of the appropriate starting Az-L-A compound and the desired B-group, as outlined in Scheme 2.

The PROTAC compounds of Examples 18d and 18e as detailed herein after were prepared in accordance with the above general methodology from the appropriate starting preparatory azide and B-group.

SCHEME 5

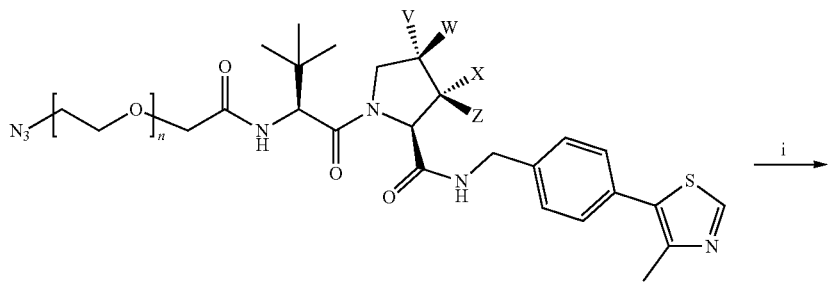

16a: V = H, W = OH, X = H, Z = F, n = 3
16b: V = OH, W = H, X = F, Z = H, n = 3
16c: V = H, W = OH, X = F, Z = H, n = 3
16d: V = OH, W = H, X = H, Z = F, n = 3
16e: V = OH, W = H, X = H, Z = F, n = 2

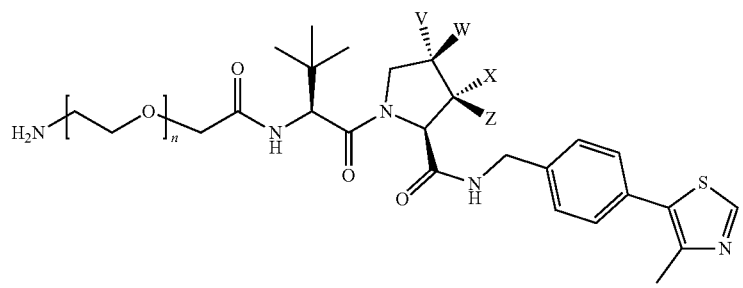

17a: V = H, W = OH, X = H, Z = F, n = 3
17b: V = OH, W = H, X = F, Z = H, n = 3
17c: V = H, W = OH, X = F, Z = H, n = 3
17d: V = OH, W = H, X = H, Z = F, n = 3
17e: V = OH, W = H, X = H, Z = F, n = 2

↓ ii

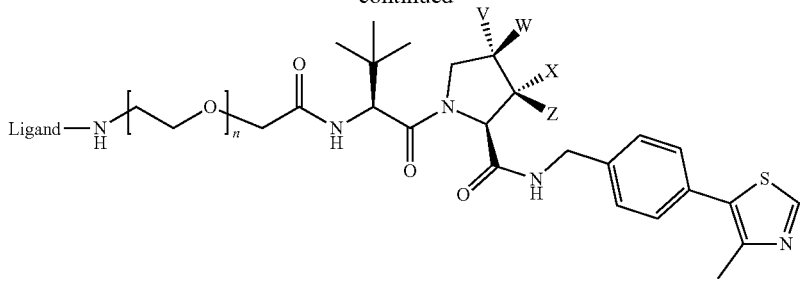

18a: V = H, W = OH, X = H, Z = F, n = 3, Ligand = (+)-JQ1
18b: V = OH, W = H, X = F, Z = H, n = 3, Ligand = (+)-JQ1
18c: V = H, W = OH, X = F, Z = H, n = 3, Ligand = (+)-JQ1
18d: V = OH, W = H, X = H, Z = F, n = 3, Ligand = (+)-JQ1
18e: V = OH, W = H, X = H, Z = F, n = 2, Ligand = iBET726

The conditions used for exemplary preparation in Scheme 5 are as follows: (i) H₂, Pd/C, MeOH, rt; (ii) ligand—COOH, DIPEA, HATU, HOAT, in DMF, rt.

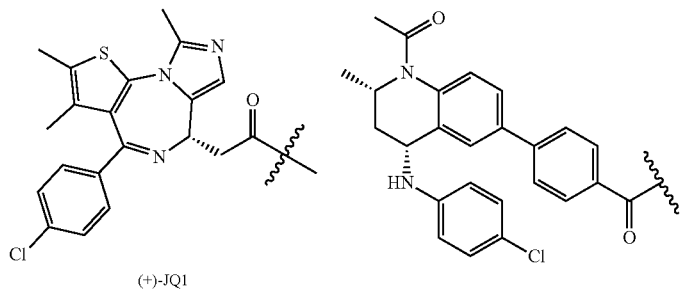

(+)-JQ1

Exemplary PROTACs Prepared in Accordance with the Process of Scheme 5

Example Compound 18d: 2R,3S,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-3-fluoro-4-hydroxy-N-(4-(4-methylthiazol-5-yl)benzyl)pyrrolidine-2-carboxamide To a solution of preparative compound 16d (7.0 mg, 0.0105 mmol) in methanol (2.0 mL), a catalytic amount of Pd/C (10% dry) was added. The mixture was stirred under hydrogen atmosphere for one hour. HPLC analysis showed complete conversion of the starting material and formation of the desired intermediate amine 17d ((METHOD 2, rt=2.674 min, m/z=638.3, [M+H]⁺). The mixture was filtered through a syringe filter and the solvent was removed. The crude amine intermediate was then dissolved in DMF (0.5 mL), and added to a solution of JQ1-COOH (4.2 mg, 0.0105 mmol), HATU (4.0 mg, 0.0105 mmol), HOAT (1.5 mg, 0.0105 mmol) and DIEPA (5.4 μL, 0.0315 mmol) in DMF (0.05 mL). The resultant mixture was stirred at room temperature for 3 hr. HPLC analysis (METHOD 2 rt=3.532 min, m/z=1020.3, [M+H]⁺) showed complete conversion of the starting material and formation of the desired PROTAC product. Purification by preparative HPLC afforded the pure product, 7.5 mg, 70% yield, as white solid.

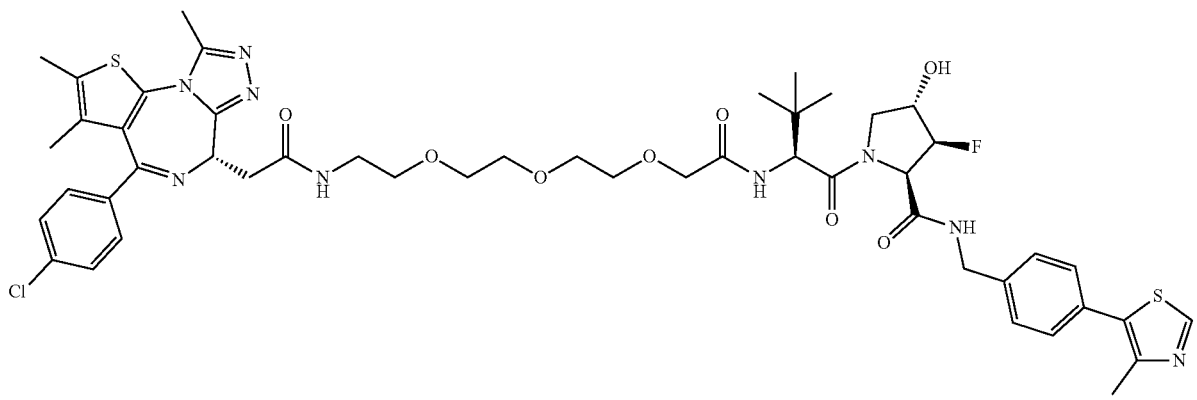 [SMILES: Cc1ncsc1-c1ccc(CNC(=O)[C@@H]2[C@H](F)[C@@H](O)CN2C(=O)[C@@H](NC(=O)COCCOCCOCCNC(=O)C[C@@H]2N=C(c3ccc(Cl)cc3)c3c(sc(C)c3C)-n3c(C)nnc32)C(C)(C)C)cc1]

$^1$H NMR (400 MHz, MeOD) δ: 8.93 (s, 1H), 7.48-7.39 (m, 8H), 5.15-4.99 (m, 1H), 4.83-4.72 (m, 2H), 4.67-4.63 (m, 1H), 4.51-4.41 (m, 3H), 4.12-4.03 (m, 2H), 3.96-3.93 (m, 2H), 3.74-3.59 (m, 11H), 3.49-3.43 (m, 3H), 2.71 (s, 3H), 2.48 (s, 6H), 2.46 (s, 6H), 1.71 (s, 3H), 1.08 (s, 9H). $^{19}$F-NMR δ: −195.32

Example Compound 18b: (2R,3R,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-3-fluoro-4-hydroxy-N-(4-(4-methylthiazol-5-yl)benzyl)pyrrolidine-2-carboxamide

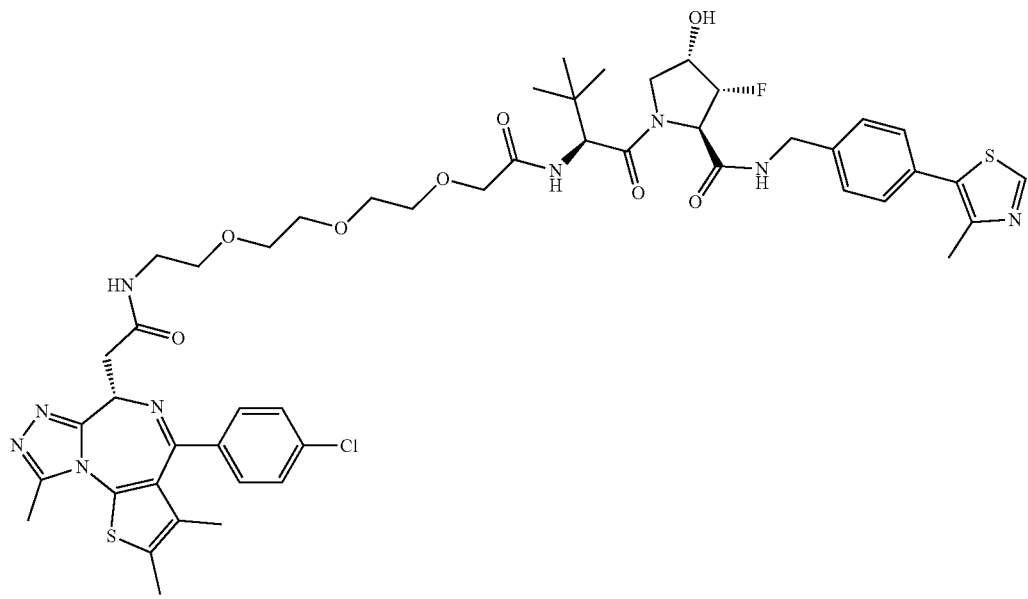 [SMILES: Cc1ncsc1-c1ccc(CNC(=O)[C@@H]2[C@@H](F)[C@@H](O)CN2C(=O)[C@@H](NC(=O)COCCOCCOCCNC(=O)C[C@@H]2N=C(c3ccc(Cl)cc3)c3c(sc(C)c3C)-n3c(C)nnc32)C(C)(C)C)cc1]

Prepared as described for preparative compound 18d, 72% yield, white solid. HPLC analysis (METHOD 2 rt=3.554 min, m/z=1020.3, [M+H]$^+$)
$^1$H NMR (400 MHz, MeOD) δ: 8.88 (s, 31367398H), 7.48-7.39 (m, 9H), 5.06-4.90 (m, 1H), 4.71-4.68 (m, 1H), 4.66-4.48 (m, 4H), 4.36 (d, J=16.1 Hz, 1H), 4.10-4.05 (m, 3H), 3.77-3.66 (m, 10H), 3.61 (t, J=5.8 Hz, 2H), 3.49-3.43 (m, 3H), 2.70 (s, 3H), 2.48 (s, 3H), 2.46 (s, 3H), 1.71 (s, 3H), 1.06 (s, 9H). $^{19}$F-NMR δ: −200.23.

Example Compound 18e: (2R,3S,4S)-1-((S)-1-(4-((2S,4R)-1-acetyl-4-(4-chlorobenzyl)-2-methyl-1,2,3,4-tetrahydroquinolin-6-yl)phenyl)-12-(tert-buytl)-1,10-dioxo-5,8-dioxa-2,11-diazatridecan-13-oyl)-3-fluoro-4-hydroxy-N-(4-(4-methylthiazol-5-yl)benzyl)pyrrolidine-2-carboxamide

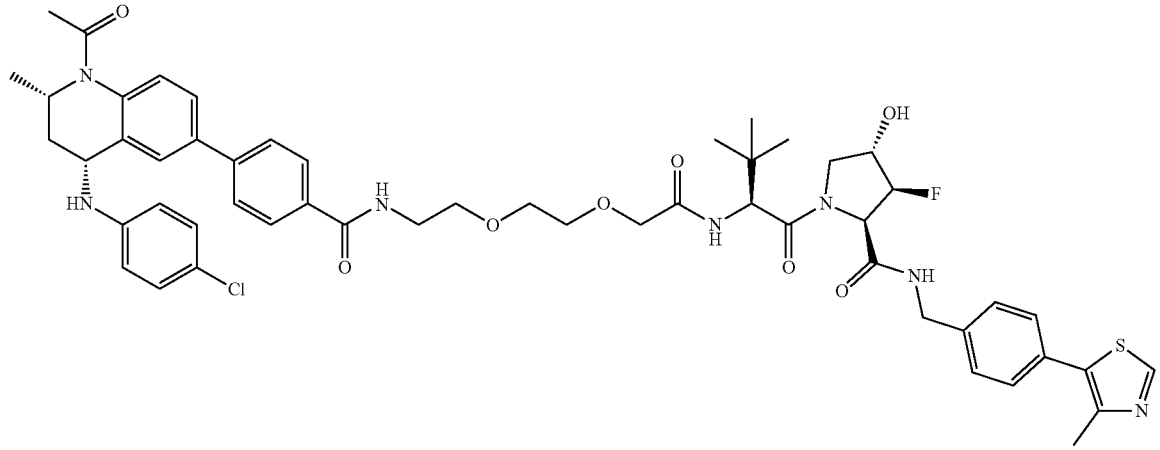 [SMILES: CC(=O)N1c2ccc(-c3ccc(C(=O)NCCOCCOCC(=O)N[C@H](C(=O)N4C[C@H](O)[C@@H](F)[C@H]4C(=O)NCc4ccc(-c5scnc5C)cc4)C(C)(C)C)cc3)cc2[C@H](Nc2ccc(Cl)cc2)C[C@@H]1C]

Example compound 18e, was obtained in accordance with the methodology as described for preparative compound 18d, and starting from preparative compound 16e. The product was obtained in 75% yield as a white solid. HPLC analysis (METHOD 2) rt=3.662 min, m/z=883.4, [M-para-chloroaniline]+.

$^1$H NMR (400 MHz, MeOD) δ: 8.87 (s, 1H), 8.60 (t, J=5.7 Hz, 1H), 7.90-7.75 (m, 3H), 7.64-7.56 (m, 4H), 7.44-7.36 (m, 5H), 7.12-7.09 (m, 2H), 6.73-6.68 (m, 2H), 5.15-5.00 (m, 1H), 4.84-4.75 (m, 2H), 4.46-4.41 (m, 3H), 4.26 (dd, J=4.8, 12.6 Hz, 1H), 4.10-3.94 (m, 4H), 3.76-3.60 (m, 8H), 2.74-2.66 (m, 1H), 2.44 (s, 3H), 2.25 (s, 3H), 1.37-1.29 (m, 1H), 1.19 (d, J=6.5 Hz, 3H), 1.05 (s, 9H). $^{19}$F-NMR δ: −192.18

Scheme 6—Synthesis of Azide-Linker Groups (Az-L)

45 min. Bromoacetic acid (10 mmol, 1 eq.) in anhydrous THF (25 ml) was then added and the reaction mixture allowed to warm to room temperature and stirred for 18 h. The solvent was removed in vacuo, the residue acidified to pH 2 with 1 M hydrochloric acid and the aqueous phase extracted for three times with dichloromethane. The combined organic layers were dried over magnesium sulphate and then purified by flash column chromatography using 10% methanol in dichloromethane to obtain the title compound (A6).

Compound (A7) was synthesized in accordance with the method provided for compound (A6) and starting from tetraethylene glycol.

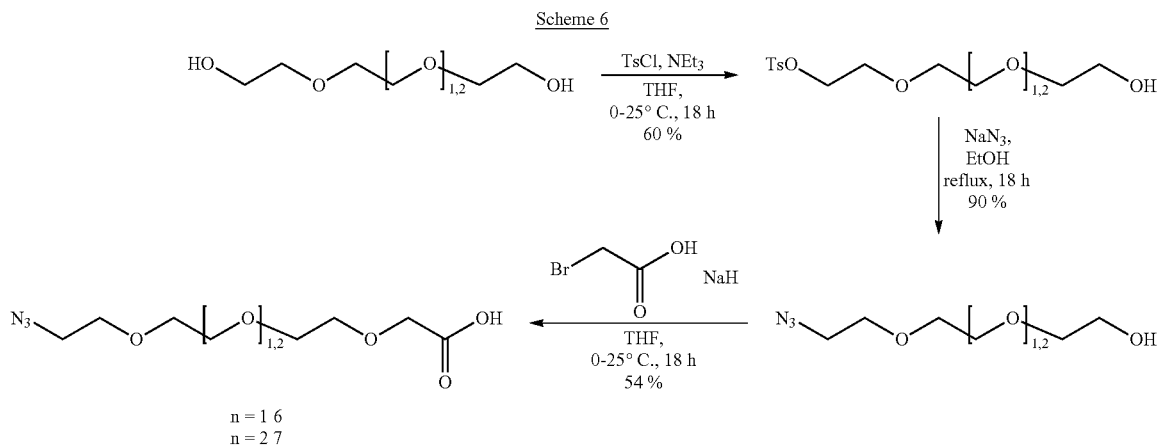

Scheme 6 n = 1 6
n = 2 7

Any azide-linker suitable for use in the preparation of an intermediate compound of structure Az-L-A as defined herein can be prepared in accordance with the general methodology outlined in Scheme 6 for the preparation of azide-linker compounds (A6) and (A7) by selection of the appropriate starting material.

Compound (A6) was Synthesized Starting from Triethylene Glycol.

Tri-ethylene glycol (120 mmol, 3 eq.) was dissolved in anhydrous THF (80 ml) and triethylamine (80 mmol, 2 eq.) was added. At 0° C. p-toluenesulfonyl chloride (40 mmol, 1 eq.) in anhydrous THF (10 ml) was added dropwise over 45 min. The reaction mixture was allowed to warm to room temperature and stirred overnight. The solvent was then removed in vacuo and the crude mixture purified by flash column chromatography using a gradient from 30%-90% Ethyl acetate in heptane.

The tosylates (20 mmol, 1 eq.) were dissolved in ethanol, sodium azide (40 mmol, 2 eq.) was added and the reaction mixture heated to reflux for 18 h. After cooling to room temperature the solvent was removed in vacuo and the residue dissolved in water. The aqueous phase was extracted three times with dichloromethane. The organic phase was then dried over magnesium sulphate and then the solvent removed in vacuo.

At 0° C. to the solution of the azides (10 mmol, 1 eq.) dissolved in anhydrous THF (25 ml) sodium hydride (20 mmol, 2 eq.) was added and the reaction mixture stirred for (S)-2-(4-(4-chlorophenyl)-2,3,9-trimethyl-6H-thieno [3,2-f][1,2,4]triazolo[4,3-a][1,4]diazepin-6-yl)acetic Acid (19)

17

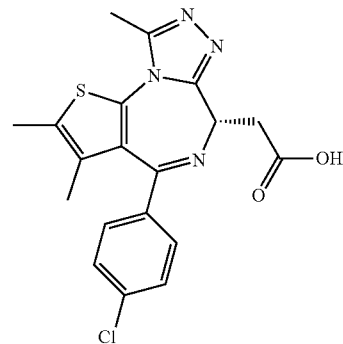

(+)-JQ-1 (50 mg, 109 μmol) was dissolved in formic acid (3 ml) and stirred for 18 h at 25° C. After addition of water the reaction mixture was extracted three times with dichloromethane. The combined organic layers were dried over magnesium sulfate and evaporated to dryness to obtain the title compound which was directly used for the next reaction step. HPLC analysis (METHOD 2): rt=3.314 min, m/z=401.0, [M+H]+. Yield 42.1 mg (96%).

Preparation of Compounds of General Formula I, IA or IB in Accordance with General Scheme C (2R,3R,4S)-1-((R)-2-amino-3-methyl-3-(tritylthio)butanoyl)-3-fluoro-4-hydroxy-N-(4-(4-methylthiazol-5-yl)benzyl)pyrrolidine-2-carboxamide (20)

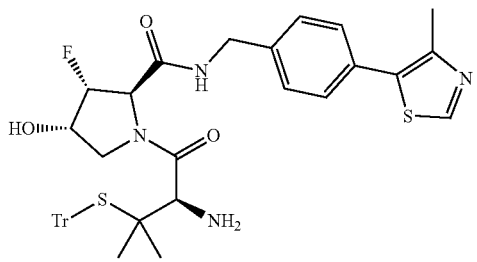

To a solution of 12b (100 mg, 0.230 mmol) in DCM/MeOH 9:1 (1 mL), 4N HCl in dioxane (1 mL) was added and mixture was stirred for 4 hours at room temperature. Volatiles were removed under vacuum, the residue was dissolved in water and freeze-dried to afford (2R,3R,4S)-3-fluoro-4-hydroxy-2-((4-(4-methylthiazol-5-yl)benzyl)carbamoyl)pyrrolidin-1-ium chloride (85 mg, 99%) as a light yellow powder which was used without any further purification.

To a solution of Fmoc-S-trityl-L-penicillamine (141.8 mg, 0.230 mmol) in DMF (1 mL), HATU (87.5 mg, 0.230 mmol) and HOAT (31 mg, 0.230 mmol) were added, followed by DIPEA (99 μL, 0.575 mmol). The bright yellow solution was then added to a mixture of (2R,3R,4S)-3-fluoro-4-hydroxy-2-((4-(4-methylthiazol-5-yl)benzyl)carbamoyl)pyrrolidin-1-ium chloride (85 mg, 0.230 mmol) and DIPEA (99 μL, 0.575 mmol) in DMF (1.5 mL). After 2 hours complete conversion of the starting materials was observed by HPLC-MS (basic method), water was added (10 mL) and the mixture was extracted with AcOEt (3×25 mL). The organic phase was washed with brine (10 mL) and dried over anhydrous MgSO₄. Solvents were removed under vacuum to afford compound 11 which was dissolved in DCM (2 mL). Piperidine (400 μL~4 mmol) was added and the reaction mixture was stirred for 1 hour. Volatiles were removed under vacuum and the crude was purified by FCC (from 5 to 15% of 0.7 M NH₃ in MeOH in DCM) to afford the title compound 12 as a white solid (122 mg, 75% yield). MS analysis: C40H41FN4O3S2 expected 708.3, found 709.3 [M+H⁺].

¹H NMR (500 MHz, CDCl₃) δ: 8.63 (s, 1H), 7.85 (t, J=5.3 Hz, 1H), 7.27-7.11 (m, 19H), 5.50 (d, J=2.9 Hz, 1H), 5.04-4.90 (m, 1H), 4.57 (dd, J=7.0, 15.1 Hz, 1H), 4.53-4.44 (m, 2H), 4.35-4.27 (m, 1H), 3.30 (d, J=12.0 Hz, 1H), 2.99-2.93 (m, 1H), 2.44 (s, 3H), 1.11 (s, 3H), 1.08 (s, 3H). 19F NMR δ: -204.48.

(2R,3R,4S)-1-((R)-2-acetamido-3-methyl-3-(tritylthio)butanoyl)-3-fluoro-4-hydroxy-N-(4-(4-methylthiazol-5-yl)benzyl)pyrrolidine-2-carboxamide (21)

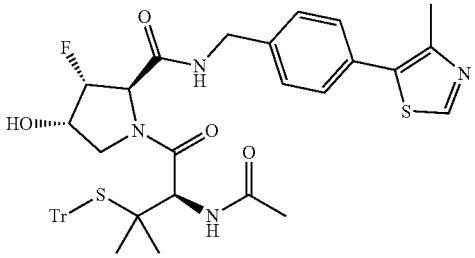

To a solution of (2R,3R,4S)-1-((R)-2-amino-3-methyl-3-(tritylthio)butanoyl)-3-fluoro-4-hydroxy-N-(4-(4-methylthiazol-5-yl)benzyl)pyrrolidine-2-carboxamide (30 mg, 0.042 mmol) in DCM (0.5 mL) at 0° C., TEA (7 μL, 0.050 mmol) and acetic anhydride (5 μL, 0.050 mmol) were added. The mixture was let to react at room temperature for 2 hours. The mixture was diluted with DCM (1 mL), washed with water (1 mL) and brine (1 mL), dried over MgSO₄ and the solvent was removed under reduced pressure to afford the title compound (31 mg, 98% yield) which was used without further purification. MS analysis: C42H43FN4O4S2, expected 750.3 found 751.3 [M+H⁺].

(2R,3R,4S)-3-fluoro-1-((R)-2-(1-fluorocyclopropane-1-carboxamido)-3-methyl-3-(tritylthio)butanoyl)-4-hydroxy-N-(4-(4-methylthiazol-5-yl)benzyl)pyrrolidine-2-carboxamide (22)

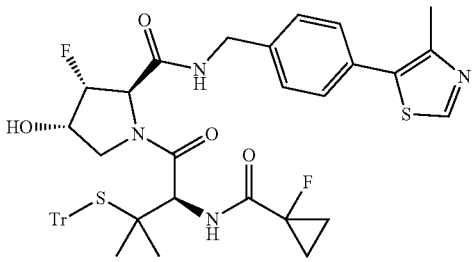

To a solution of compound (2R,3R,4S)-1-((R)-2-amino-3-methyl-3-(tritylthio)butanoyl)-3-fluoro-4-hydroxy-N-(4-(4-methylthiazol-5-yl)benzyl)pyrrolidine-2-carboxamide (30 mg, 0.042 mmol), HATU (16 mg, 0.042 mmol), HOAT (5.71 mg, 0.042 mmol) 1-fluorocyclopropane-1-carboxylic acid (4.3 mg, 0.042 mmol) in DMF (1 mL), DIPEA (25 μL, 0.141 mmol) was added. The reaction mixture was stirred at room temperature for 2 hours, then water (1 mL) was added and the resulting mixture was extracted with DCM (3×5 mL). After drying the organic phase over MgSO₄ and the solvent was removed under reduced pressure to afford the title compound (28.3 mg, 85% yield) which was used without further purification.

101

(2R,3R,4S)-1-((R)-2-acetamido-3-mercapto-3-methylbutanoyl)-3-fluoro-4-hydroxy-N-(4-(4-methylthiazol-5-yl)benzyl)pyrrolidine-2-carboxamide (23)

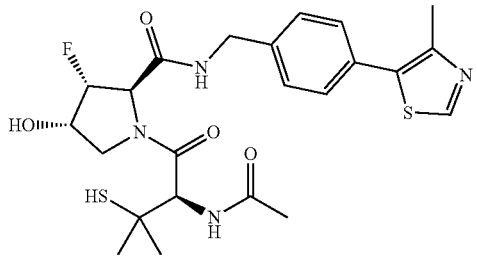 [SMILES: CC(=O)N[C@H](C(=O)N1C[C@H](O)[C@H](F)[C@H]1C(=O)NCc1ccc(-c2scnc2C)cc1)C(C)(C)S]

Compound 22 (30 mg, 0.04 mmol) was dissolved in 1.8 mL of DCM. TIPS (0.1 mL) and TFA (0.1 mL) were added, and the yellow mixture was let to react at room temperature for 2 h. HPLC analysis (acidic method) showed complete conversion of the starting material. Volatiles were removed and the crude was dissolved in MeOH, filtered and purified by preparative HPLC and freeze-dried to give pure deprotected compound as white solid (16 mg, 79% yield). MS analysis: C23H29FN4O4S2 expected 508.2, found 509.2 [M+H$^+$].

$^1$H NMR (500 MHz, MeOD) δ: 8.88 (s, 1H), 8.84 (t, J=6.0 Hz, 0H), 8.14 (d, J=8.9 Hz, 1H), 7.47-7.42 (m, 4H), 5.05-4.92 (m, 1H), 4.91 (d, J=8.8 Hz, 1H), 4.65 (dd, J=2.5, 21.5 Hz, 1H), 4.57-4.37 (m, 3H), 4.29 (dd, J=6.4, 10.3 Hz, 1H), 3.75-3.70 (m, 1H), 2.49 (s, 3H), 2.03 (s, 3H), 1.43 (s, 3H), 1.40 (s, 3H). 19F NMR δ: −199.94 13C NMR: 173.3, 171.5, 170.5, 153.0, 149.2, 140.0, 133.4, 131.8, 130.5, 129.1, 95.3, 93.8, 71.1, 70.9, 66.2, 66.0, 59.4, 52.2, 46.8, 43.9, 29.8, 28.8.

(2R,3R,4S)-3-fluoro-1-((R)-2-(1-fluorocyclopropane-1-carboxamido)-3-mercapto-3-methylbutanoyl)-4-hydroxy-N-(4-(4-methylthiazol-5-yl)benzyl)pyrrolidine-2-carboxamide (24)

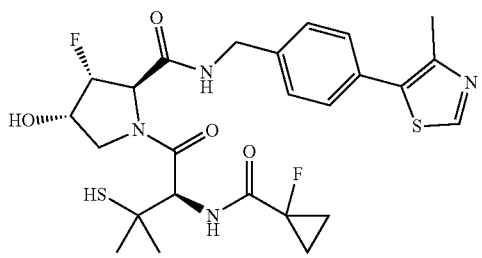 [SMILES: Cc1ncsc1-c1ccc(CNC(=O)[C@@H]2[C@@H](F)[C@@H](O)CN2C(=O)[C@@H](NC(=O)C2(F)CC2)C(C)(C)S)cc1]

Prepared as described for compound 23, obtained 14 mg, 74% yield.

$^1$H NMR (500 MHz, MeOD) δ: 8.88 (s, 1H), 7.48-7.43 (m, 4H), 5.06-4.92 (m, 2H), 4.68 (dd, J=2.9, 21.2 Hz, 1H), 4.59-4.37 (m, 3H), 4.27 (dd, J=6.4, 10.0 Hz, 1H), 3.77-3.72 (m, 1H), 2.49 (s, 3H), 1.46 (s, 3H), 1.42-1.32 (m, 7H). 19F NMR δ: −200.07, −198.33. 13C NMR: 171.8, 171.7, 171.0, 170.4, 170.4, 152.9, 149.2, 140.0, 133.4, 131.8, 130.5, 129.6, 129.0, 95.3, 93.8, 80.1, 78.3, 71.1, 70.9, 66.1, 66.0, 58.4, 52.3, 47.4, 44.0, 30.1, 29.0, 15.9, 14.3, 14.2.

102

(2R,3R,4S)-1-((R)-2-acetamido-3-((6-aminohexyl)thio)-3-methylbutanoyl)-3-fluoro-4-hydroxy-N-(4-(4-methylthiazol-5-yl)benzyl)pyrrolidine-2-carboxamide (25)

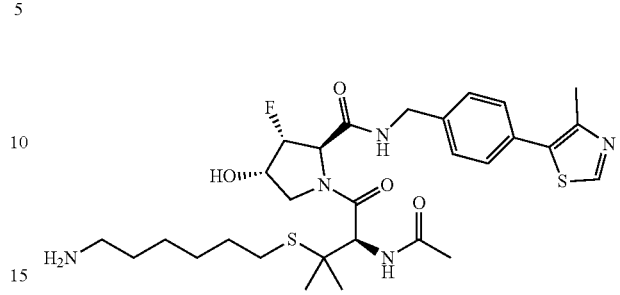

Under nitrogen and at 0° C., a solution of compound 23 (10 mg, 0.020 mmol) in DMF (0.5 mL) was treated with DBU (3.3 μL, 0.022 mmol) followed by N-(4-Bromohexyl) phthalimide (6.6 mg, 0.022 mmol). The reaction mixture was let to react at room temperature until complete conversion of the starting material was observed by HPLC (acidic method, 1-3 h). The reaction was cooled to 0° C. and treated with few drops of KHSO$_4$ (5%) to pH=3-4. The solvent was removed under vacuum and the crude was dissolved in MeOH, filtered and purified by preparative HPLC to obtain 11.5 mg (80% yield) of alkylated product. MS analysis: C37H44FN5O6S2 expected 737.3, found 738.3 [M+H$^+$]. The alkylated product was then dissolved in ethanol (0.5 mL) and treated with hydrazine monohydrate (24 μL, 0.32 mmol) at 60° C. for two hours. The reaction mixture was cooled to room temperature, filtered and purified by preparative HPLC to give the expected amine MS analysis: C29H42FN5O4S2 expected 607.3, found 608.3[M+H$^+$], which was used as crude.

(2R,3R,4S)-1-((R)-3-((6-aminohexyl)thio)-2-(1-fluorocyclopropane-1-carboxamido)-3-methylbutanoyl)-3-fluoro-4-hydroxy-N-(4-(4-methylthiazol-5-yl)benzyl)pyrrolidine-2-carboxamide (26)

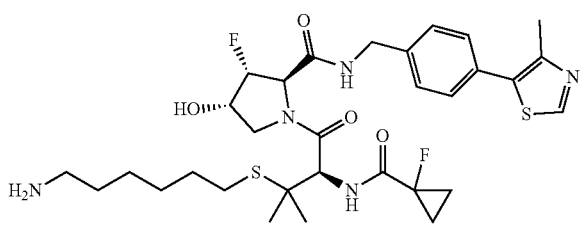 [SMILES: Cc1ncsc1-c1ccc(CNC(=O)[C@@H]2[C@@H](F)[C@@H](O)CN2C(=O)[C@@H](NC(=O)C2(F)CC2)C(C)(C)SCCCCCCN)cc1]

Prepared according to the procedure described for compound 25, used as crude.

(2R,3R,4S)-1-((R)-2-acetamido-3-((6-(2-((S)-4-(4-chlorophenyl)-2,3,9-trimethyl-6H-thieno[3,2-f][1,2,4]triazolo[4,3-a][1,4]diazepin-6-yl)acetamido)hexyl)thio)-3-methylbutanoyl)-3-fluoro-4-hydroxy-N-(4-(4-methylthiazol-5-yl)benzyl)pyrrolidine-2-carboxamide (27)

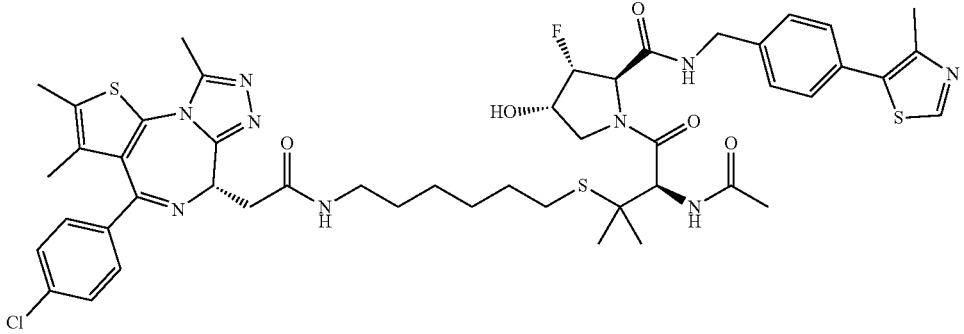 [SMILES: CC(=O)N[C@H](C(=O)N1C[C@H](O)[C@H](F)[C@H]1C(=O)NCc1ccc(-c2scnc2C)cc1)C(C)(C)SCCCCCCNC(=O)C[C@@H]1N=C(c2ccc(Cl)cc2)c2c(sc(C)c2C)-n2c(C)nnc21]

Crude (2R,3R,4S)-1-((R)-2-acetamido-3-((6-aminohexyl)thio)-3-methylbutanoyl)-3-fluoro-4-hydroxy-N-(4-(4-methylthiazol-5-yl)benzyl)pyrrolidine-2-carboxamide (assumed 0.0108 mmol) was dissolved in DMF (0.25 mL) and added to a solution of (S)-2-(4-(4-chlorophenyl)-2,3,9-trimethyl-6H-thieno[3,2-f][1,2,4]triazolo[4,3-a][1,4]diazepin-6-yl)acetic acid (+)-JQ1-COOH (4.32 mg, 0.0108 mmol), HATU (4.1 mg, 0.0108 mmol), HOAT (1.5 mg, 0.0108 mmol) and DIPEA (5.5 µl, 0.0324 mmol) in DMF (0.5 mL). After stirring at room temperature for 1 h, the reaction was quenched with water (0.1 mL) and the mixture of water/DMF was removed under high vacuum at room temperature (overnight). The crude mixture was dissolved in MeOH, filtered and purified by preparative HPLC to give the title compound. Obtained 5 mg, 45% yield. MS analysis: C48H57ClFN9O5S3 expected 989.3, found 990.3 [M+H$^+$].

$^1$H NMR (500 MHz, MeOD) δ 8.91 (s, 1H), 8.62 (t, J=5.9 Hz, 1H), 8.19 (d, J=8.8 Hz, 1H), 7.47-7.41 (m, 9H), 5.07-4.94 (m, 1H), 4.92-4.90 (m, 1H), 4.70-4.63 (m, 2H), 4.55-4.39 (m, 3H), 4.13 (dd, J=6.8, 9.9 Hz, 1H), 3.79-3.75 (m, 1H), 3.45-3.39 (m, 1H), 3.31-3.18 (m, 4H), 2.71 (s, 3H), 2.56 (t, J=7.4 Hz, 2H), 2.48 (s, 3H), 2.45 (s, 3H), 2.02 (s, 3H), 1.70 (s, 3H), 1.56-1.35 (m, 14H). 19F NMR=−200.10. 13C NMR: 171.7, 171.1, 164.9, 155.6, 151.6, 150.8, 147.5, 138.5, 136.7, 136.6, 132.1, 132.0, 132.0, 130.7, 130.2, 129.9, 129.0, 128.4, 127.6, 93.8, 69.6, 69.5, 55.5, 53.8, 50.6, 38.9, 37.3, 29.1, 28.9, 28.4, 27.8, 26.2, 24.5, 24.2, 20.8, 14.3, 13.0, 11.5, 10.1.

(2R,3R,4S)-1-((R)-3-((6-(2-((S)-4-(4-chlorophenyl)-2,3,9-trimethyl-6H-thieno[3,2-f][1,2,4]triazolo[4,3-a][1,4]diazepin-6-yl)acetamido)hexyl)thio)-2-(1-fluorocyclopropane-1-carboxamido)-3-methylbutanoyl)-3-fluoro-4-hydroxy-N-(4-(4-methylthiazol-5-yl)benzyl)pyrrolidine-2-carboxamide (28)

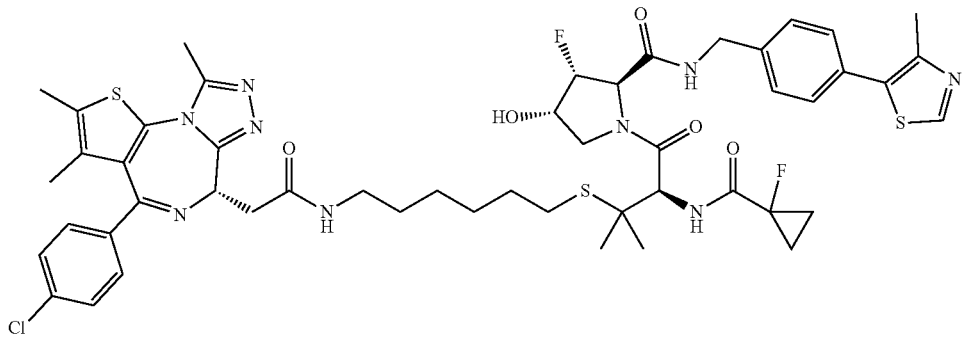 [SMILES: Cc1ncsc1-c1ccc(CNC(=O)[C@@H]2[C@@H](F)[C@@H](O)CN2C(=O)[C@@H](NC(=O)C2(F)CC2)C(C)(C)SCCCCCCNC(=O)C[C@@H]2N=C(c3ccc(Cl)cc3)c3c(sc(C)c3C)-n3c(C)nnc32)cc1]

Prepared according to the procedure described for compound 28, 4 mg, 38% yield. MS analysis: C50H58ClF2N9O5S3 expected 1033.3, found 1034.3 [M+H⁺].

¹H NMR (500 MHz, MeOD) δ: 8.88 (s, 1H), 8.31 (t, J=5.7 Hz, 1H), 7.76-7.73 (m, 1H), 7.47-7.40 (m, 9H), 5.07-4.95 (m, 1H), 4.92-4.90 (m, 1H), 4.69 (dd, J=2.8, 21.5 Hz, 1H), 4.65-4.61 (m, 1H), 4.59-4.37 (m, 3H), 4.14 (dd, J=6.4, 10.1 Hz, 1H), 3.78-3.73 (m, 1H), 3.44-3.39 (m, 1H), 3.30-3.18 (m, 3H), 2.70 (s, 3H), 2.61-2.53 (m, 2H), 2.49 (s, 3H), 2.45 (s, 3H), 1.55-1.31 (m, 18H). 19F NMR: −200.22, −198.08.

Comparative Compounds with Pyrrolidine Ring not Comprising the Fluor Substituent (2S,4R)-1-((R)-2-amino-3-methyl-3-(tritylthio)butanoyl)-4-hydroxy-N-(4-(4-methylthiazol-5-yl)benzyl)pyrrolidine-2-carboxamide (29)

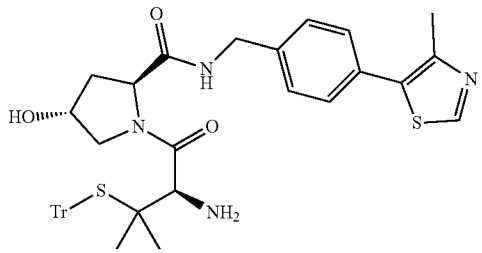

Prepared according to the procedure described for compound 20.

¹H-NMR (400 MHz, CD₃OD, 25° C.) δ: 8.90 (s, 1H), 7.63-7.60 (m, 6H), 7.40-7.33 (m, 4H), 7.31-7.29 (m, 6H), 7.24-7.19 (m, 3H), 4.46 (t, J=8.2 Hz, 1H), 4.37 (br s, 1H), 4.31 (m, 2H), 3.35 (s, 1H), 3.24 (dd, J=11.1 Hz, J=4.1 Hz, 1H), 3.07-3.04 (m, 1H), 2.70 (s, 1H), 2.47 (s, 3H), 2.16-2.11 (m, 1H), 1.99-1.92 (m, 1H), 1.26 (s, 3H), 1.19 (s, 3H).

¹³C-NMR (101 MHz, CD₃OD, 25° C.) δ: 172.9, 171.4, 151.5, 147.7, 144.9, 138.7, 132.0, 129.7, 129.0, 127.5, 127.4, 126.5, 69.3, 67.7, 59.4, 57.6, 57.3, 56.7, 42.1, 37.4, 24.6, 24.1, 14.4.

(2S,4R)-1-((R)-2-acetamido-3-methyl-3-(tritylthio)butanoyl)-4-hydroxy-N-(4-(4-methylthiazol-5-yl)benzyl)pyrrolidine-2-carboxamide (30)

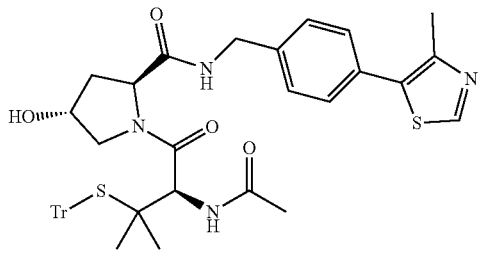

Prepared according to the procedure described for compound 21.

MS analysis: C₄₂H₄₄N₄O₄S₂ expected 732.3, found 733.3 [M+H⁺].

¹H-NMR (400 MHz, CDCl₃, 25° C.) δ: 8.71 (s, 1H), 7.52-7.49 (m, 6H), 7.39-7.31 (m, 3H), 7.25-7.20 (m, 11H), 6.25 (d, J=5.2 Hz, 1H), 4.64 (t, J=8.1 Hz, 1H), 4.37 (br s, 1H), 4.31-4.18 (m, 2H), 3.61 (d, J=5.3 Hz, 1H), 3.52-3.49 (m, 1H), 3.30-3.29 (m, 1H), 3.22 (dd, J=11.5 Hz, J=3.6 Hz, 1H), 2.52 (s, 3H), 2.36-2.30 (m, 1H), 2.16-2.11 (m, 1H), 1.95 (s, 3H), 1.76 (br s, 1H), 1.18 (s, 3H), 0.97 (s, 3H).

¹³C-NMR (101 MHz, CDCl₃, 25° C.) δ: 170.7, 170.5, 170.3, 150.3, 148.5, 144.2, 138.2, 131.7, 130.8, 129.7, 129.6, 129.4, 127.9, 127.0, 77.2, 70.1, 68.5, 58.5, 57.1, 56.6, 53.6, 42.8, 36.4, 26.1, 25.4, 22.9, 16.2.

(2S,4R)-1-((R)-2-(1-fluorocyclopropane-1-carboxamido)-3-methyl-3-(tritylthio)butanoyl)-4-hydroxy-N-(4-(4-methylthiazol-5-yl)benzyl)pyrrolidine-2-carboxamide (31)

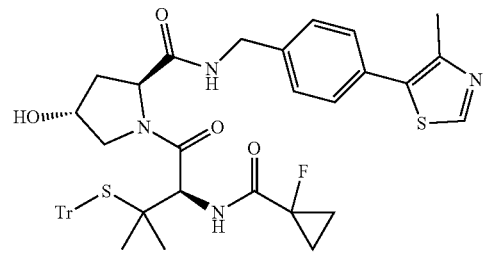

Prepared according to the procedure described for compound 22.

MS analysis: C44H45FN4O4S2 expected 776.3 found 777.3 [M+H⁺].

¹H NMR (400 MHz, CDCl3) δ: 8.71 (s, 1H), 7.54-7.51 (m, 6H), 7.34-7.31 (m, 3H), 7.25-7.19 (m, 12H), 4.69-4.64 (m, 1H), 4.38-4.36 (m, 1H), 4.32-4.19 (m, 2H), 3.66 (d, J=4.2 Hz, 1H), 3.50 (d, J=11.6 Hz, 1H), 3.26 (dd, J=3.9, 11.6 Hz, 1H), 3.09 (d, J=5.9 Hz, 1H), 2.41-2.33 (m, 1H), 2.14-2.07 (m, 1H), 1.38-1.21 (m, 7H), 0.97 (s, 3H). 19F NMR: −197.41.

(2S,4R)-1-((R)-2-(1-cyanocyclopropane-1-carboxamido)-3-methyl-3-(tritylthio)butanoyl)-4-hydroxy-N-(4-(4-methylthiazol-5-yl)benzyl)pyrrolidine-2-carboxamide (32)

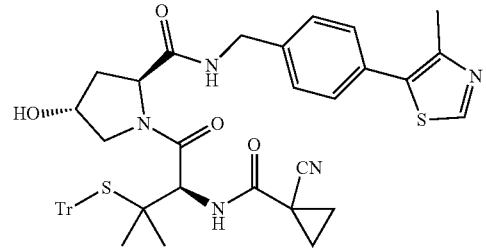

Prepared as described for compound 22. 72% yield.
MS analysis: C45H45N5O4S2, 784.0, found 785.0.
¹H NMR (400 MHz, CDCl3) d 8.71 (s, 1H), 7.57-7.53 (m, 6H), 7.34-7.32 (m, 2H), 7.25-7.16 (m, 13H), 4.64 (t, J=8.1 Hz, 1H), 4.38 (t, J=3.5 Hz, 1H), 4.29 (d, J=5.6 Hz, 2H), 3.66 (d, J=5.1 Hz, 1H), 3.47 (d, J=11.8 Hz, 1H), 3.24 (dd, J=3.6, 11.7 Hz, 1H), 2.79 (d, J=6.1 Hz, 1H), 2.53 (s, 3H), 2.50-2.36 (m, 1H), 2.12-2.06 (m, 1H), 1.69-1.62 (m, 2H), 1.58-1.46 (m, 3H), 1.20 (s, 3H).

(2S,4R)-1-((R)-2-acetamido-3-mercapto-3-methylbutanoyl)-4-hydroxy-N-(4-(4-methylthiazol-5-yl)benzyl)pyrrolidine-2-carboxamide (33)

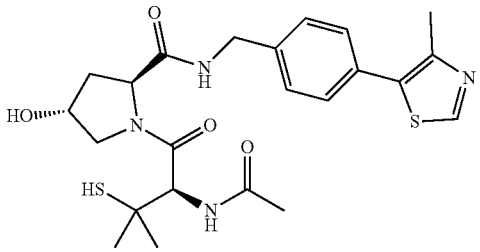 [SMILES: CC(=O)N[C@H](C(=O)N1C[C@H](O)C[C@H]1C(=O)NCc1ccc(-c2scnc2C)cc1)C(C)(C)S]

Prepared according to the procedure described for compound 23. (62 mg, 79% yield). MS analysis: $C_{23}H_{30}N_4O_4S_2$ expected 490.2, found 491.1 [M+H$^+$].

$^1$H-NMR (400 MHz, CDCl$_3$, 25° C.) δ: 8.68 (s, 1H), 7.39-7.33 (m, 4H), 7.20-7.17 (m, 1H), 6.55 (d, 1H), 4.68 (t, J=8.0 Hz, 1H), 4.59-4.52 (m, 3H), 4.35 (dd, J=14.9 Hz, J=5.2 Hz, 1H), 4.19-4.16 (m, 1H), 3.70 (dd, J=11.2 Hz, J=3.6 Hz, 1H), 3.15 (br s, 1H), 2.29 (br s, 1H), 2.52 (s, 3H), 2.48-2.42 (m, 1H), 2.20-2.15 (m, 1H), 2.01 (s, 3H), 1.36 (s, 3H), 1.31 (s, 3H).

$^{13}$C-NMR (101 MHz, CDCl$_3$, 25° C.) δ: 170.9, 170.7, 170.6, 150.4, 148.6, 137.9, 131.5, 131.1, 129.6, 128.1, 70.1, 58.9, 57.5, 56.6, 46.1, 43.3, 36.5, 30.7, 28.7, 23.0, 16.1.

(2S,4R)-1-((R)-2-acetamido-3-((6-aminohexyl)thio)-3-methylbutanoyl)-4-hydroxy-N-(4-(4-methylthiazol-5-yl)benzyl)pyrrolidine-2-carboxamide (34)

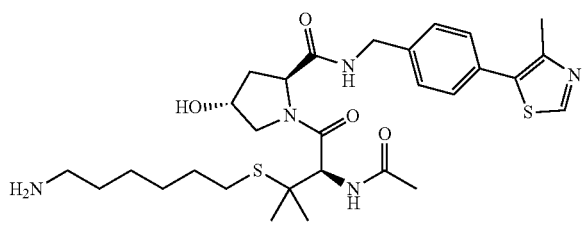 [SMILES: CC(=O)N[C@H](C(=O)N1C[C@H](O)C[C@H]1C(=O)NCc1ccc(-c2scnc2C)cc1)C(C)(C)SCCCCCCN]

Prepared according to the procedure described for compound 25.

(6.4 mg, 68% yield). MS analysis: $C_{29}H_{43}N_5O_4S_2$ expected 589.3, found 590.2 [M+H$^+$].

$^1$H NMR (400 MHz, CD$_3$OD, 25° C.) δ: 8.88 (s, 1H), 7.46-7.41 (m, 4H), 4.92 (s, 1H), 4.58 (t, J=8.3 Hz 1H), 4.52-4.38 (m, 3H), 3.93-3.84 (m, 1H), 3.85 (dd, J=10.8 Hz, J=4.0 Hz, 1H), 2.64 (t, J=7.3 Hz, 2H), 2.56 (t, J=7.4 Hz, 2H) 2.48 (s, 3H), 226-2.23 (m, 1H), 2.14-2.10 (m, 1H), 2.00 (s, 3H), 1.49-1.28 (m, 16H).

$^{13}$C-NMR (101 MHz, CD$_3$OD, 25° C.) δ: 174.4, 173.2, 171.6, 153.0, 149.2, 140.3, 133.5, 131.8, 130.6, 129.2, 71.1, 61.1, 58.0, 57.3, 43.7, 42.3, 39.2, 32.8, 30.7, 30.1, 29.3, 27.6, 26.3, 25.7, 22.5, 16.0.

(2S,4R)-1-((R)-2-acetamido-3-((6-(2-((S)-4-(4-chlorophenyl)-2,3,9-trimethyl-6H-thieno[3,2-f][1,2,4]triazol[4,3-a][1,4]diazepin-6-yl)acetamido)hexyl)thio)-3-methylbutanoyl)-4-hydroxy-N-(4-(4-methylthiazol-5-yl)benzyl)pyrrolidine-2-carboxamide (35)

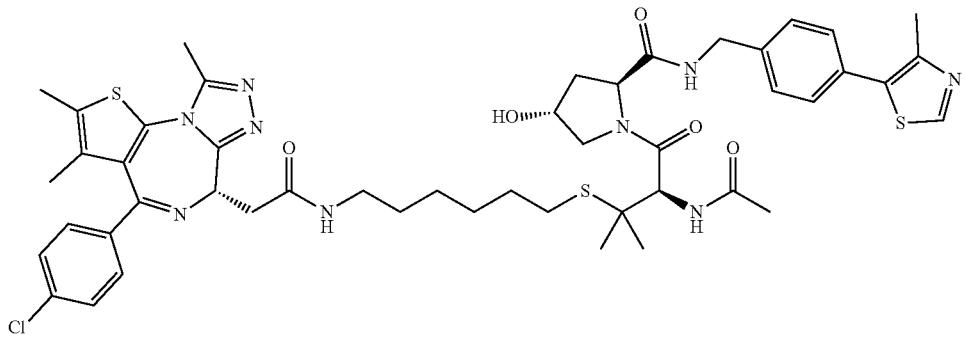 [SMILES: CC(=O)N[C@H](C(=O)N1C[C@H](O)C[C@H]1C(=O)NCc1ccc(-c2scnc2C)cc1)C(C)(C)SCCCCCCNC(=O)C[C@@H]1N=C(c2ccc(Cl)cc2)c2c(sc(C)c2C)-n2c(C)nnc21]

Prepared accordingly to procedure 27. Obtained 7.3 mg, 70% yield. MS analysis: $C_{48}H_{58}N_9ClO_5S_3$ expected 971.3, found 972.3 [M+H$^+$].

$^1$H-NMR (400 MHz, CD$_3$OD, 25° C.) δ: 8.99 (s, 1H), 8.43 (t, J=5.9 Hz, 1H exch.), 8.12 (d, J=9.4 Hz, 1H exch.), 8.07 (s, 1H exch.), 7.47-7.40 (m, 8H), 4.93-4.91 (m, 1H), 4.69-4.65 (m, 1H), 4.58 (t, J=8.3 Hz, 1H), 4.52-4.38 (m, 3H), 3.93-3.91 (m, 1H), 3.85 (dd, J=10.8 Hz, J=3.96 Hz, 1H), 3.45-3.39 (m, 1H), 3.27-3.16 (m, 3H), 2.72 (s, 3H), 2.26 (t, J=7.0 Hz, 2H), 2.49 (s, 3H), 2.45 (s, 3H), 2.25-2.22 (m, 1H), 2.14-2.07 (m, 1H), 2.00 (s, 3H), 1.70 (s, 3H), 1.54-1.36 (m, 14H).

$^{13}$C-NMR (101 MHz, CD$_3$OD, 25° C.) δ: 174.4, 173.2, 172.6, 171.6, 166.7, 157.1, 153.4, 152.6, 148.5, 140.5, 138.4, 137.9, 133.9, 133.6, 132.3, 132.2, 131.6, 131.4, 130.6, 130.0, 129.7, 129.3, 71.0, 61.2, 58.1, 57.4, 55.2, 43.7, 40.5, 39.2, 38.7, 30.7, 30.5, 30.0, 29.3, 27.7, 26.2, 25.9, 22.5, 15.7, 14.6, 13.1, 11.7.

The invention claimed is:
1. A compound having the structure:

A-L-B, or a pharmaceutically acceptable salt, enantiomer, stereoisomer, hydrate, solvate, or polymorph thereof, wherein
A is an E3 ubiquitin ligase protein binding ligand compound of formula I:

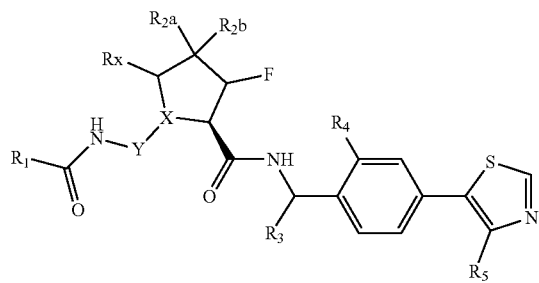

I wherein L is a group which is directly bonded to the compound of formula I and wherein L is —$(CH_2)_nL^1$ $(CH_2O)_p$—, wherein $L^1$ is a covalent bond, a 5 or 6 membered heterocyclic or heteroaromatic ring containing 1, 2 or 3 nitrogen atoms, phenyl, —$(C_2-C_4)$alkyne, —$SO_2$—, or —NH—, or wherein L is a —$(CH_2CH_2O)_b$— group wherein b is 1 to 10 and wherein L is directly bonded to the compound of formula I, wherein n and p are independently 0 to 10, wherein X is C or N, wherein $R_1$ is a covalent C-linked bond to L, a —$(CH_2)_m$ $Q_v$ group with a covalent C-linked bond to L, a $(C_1-C_4)$ alkyl group, or a C-linked $(C_3-C_4)$ heterocyclic group, wherein m is 0, 1 or 2 and v is 0 or 1, wherein Q is a $(C_3-C_4)$cyclic or $(C_3-C_4)$—C—linked nitrogen containing heterocyclic group, wherein one of the ring atoms in the Q group is optionally substituted with a —NHC(O) group or a —C(O) group, wherein said $R_1$ groups may be optionally substituted by one or more groups independently selected from F, CN, C(O) or C(O)($C_1-C_3$)alkyl, wherein $R_{2a}$ is OH, —$CHF_2$, —$CF_3$, or $NH_2$, wherein $R_{2b}$ is H, $^2H$, $^3H$, a —$(C_1-C_3)$ alkyl group, an aryl group, a heteroaryl group, —$CF_3$, —$CF_2H$, or a —$CF_2$—$(C_1-C_2)$ alkyl group, wherein $R_x$ is H, OH, —$CHF_2$, —$CF_3$, $NH_2$ or F, wherein $R_3$ and $R_4$ are independently selected from H, a covalent C-linked, a covalent O-linked, or a covalent C(O)-linked bond to L, $R_5$ is a —$(C_1-C_3)$ alkyl group or a covalent C-linked bond to L, wherein Y is

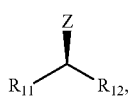

wherein Z is $CR_6R_7R_8$ or $SR_6R_7R_8R_9R_{10}$, wherein $R_{11}$ is a covalent C-linked bond or a

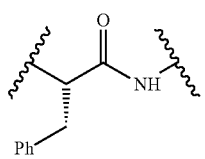

group, wherein $R_{12}$ is —C(O)— or a -C(=)-$R_{13}$ group, wherein when Z is $CR_6R_7R_8$, $R_6$ and $R_7$ are each independently —$(C_1-C_3)$ alkyl groups, or wherein $R_6$ and $R_7$ together with the C-atom to which they are attached form a —$(C_3-C_4)$ cycloalkyl group, wherein when Z is $CR_6R_7R_8$, $R_8$ is a —$(C_1-C_3)$ alkyl group, a —$(CH_2)_qR_{8*}$ group wherein q is 0, 1 or 2, a —C(O)—$R_{8*}$ group, or a —N(H)—$R_{8*}$ group, and wherein $R_{8*}$ is a covalent C-, S-, or N-linked bond to L, or H, or wherein when Z is $SR_6R_7R_8R_9R_{10}$, $R_6$, $R_7$, $R_8$, $R_9$ and $R_{10}$ are each independently selected from: F; or —$(C_1-C_3)$ alkyl groups, wherein $R_{13}$ is H, F or a—$(C_1-C_3)$ alkyl group, wherein the —$(C_1-C_3)$ alkyl groups, or —$(C_3-C_4)$ cycloalkyl groups where present in a Y group are optionally substituted by one or more substituents independently selected from: methyl; OH; or F, wherein B is a ligand which binds to a target protein or polypeptide which is to be degraded by ubiquitin ligase and is linked to A through a —C- linkage to the L group and B is independently selected from:

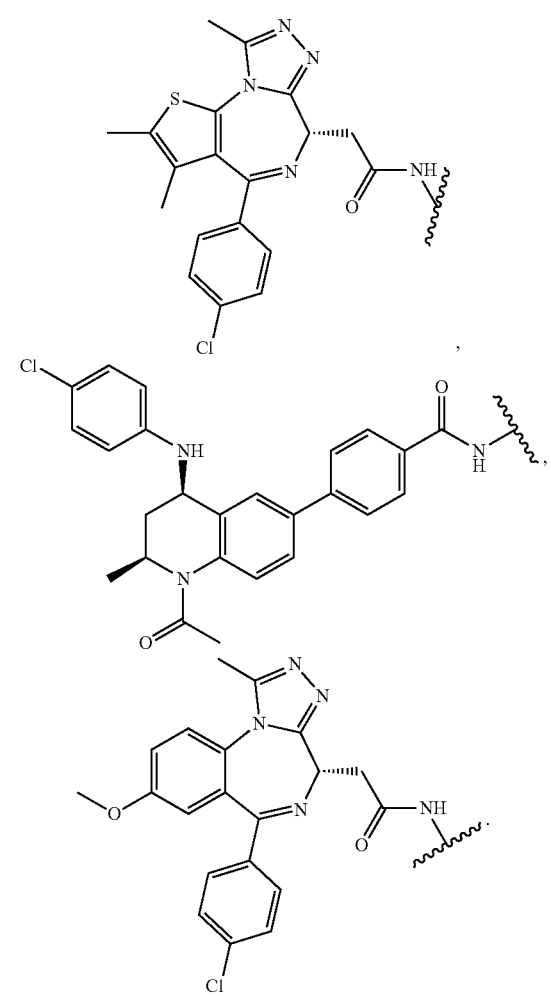

2. The compound according to claim 1 having the structure A-L-B wherein A is an E3 ubiquitin ligase protein binding ligand compound of formula IA:

IA

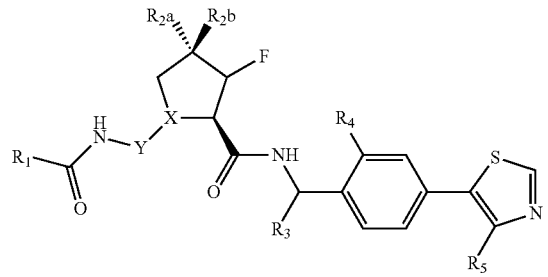

wherein X is N;
wherein L is a —(CH$_2$CH$_2$O)$_{b-}$ group wherein b is 1 to 10 and wherein L is directly bonded to the compound of formula IA, wherein R$_1$ is a covalent C-linked bond to L, a —(CH$_2$)$_m$Q$_v$ group with a covalent C-linked bond to L, a (C$_1$-C$_4$) alkyl group, or a C-linked (C$_3$-C$_4$) heterocyclic group, wherein m is 0, 1 or 2 and v is 0 or 1, and wherein when m is 0, v is 1;
wherein Q is a (C$_3$-C$_4$)cyclic or (C$_3$-C$_4$)-C-linked nitrogen containing heterocyclic group, wherein one of the ring atoms in the Q group is optionally substituted with a —NHC(O) group or a —C(O) group,
wherein said R$_1$ groups may be optionally substituted by one or more groups independently selected from F, CN, C(O) or C(O)CH$_3$,
wherein R$_{2a}$ is OH,
wherein R$_{2b}$ is H,
wherein R$_3$ and R$_4$ are independently selected from H, a covalent C-linked, a covalent O-linked, or a covalent C(O)-linked bond to L,
R$_5$ is a —(C$_1$-C$_3$) alkyl group or a covalent C-linked bond to L, wherein Y is

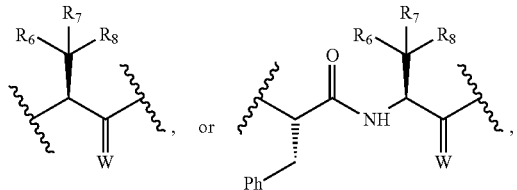

wherein W is O,
wherein R$_6$ and R$_7$ are each independently —(C$_1$-C$_3$) alkyl groups, or wherein R$_6$ and R$_7$ together with the C-atom to which they are attached form a —(C$_3$-C$_4$) cycloalkyl group,
wherein R$_8$ is a —(C$_1$-C$_3$) alkyl group, a —(CH$_2$)$_q$R$_{8*}$ group wherein q is 0, 1 or 2, a —C(O)—R$_{8*}$ group, or a —N(H)—R$_{8*}$ group, and wherein R$_{8*}$ is a covalent C-, S-, or N-linked bond to L, or H,
wherein the —(C$_1$-C$_3$) alkyl groups, or —(C$_3$-C$_4$) cycloalkyl groups where present in a Y group are optionally substituted by one or more substituents independently selected from: methyl; OH; or F,
and wherein B is
linked to A though a -C-linkage to the L group; and
B is a ligand which binds to a target protein or polypeptide which is to be degraded by ubiquitin ligase and is linked to A though a -C-linkage to the L group and B is independently selected from:

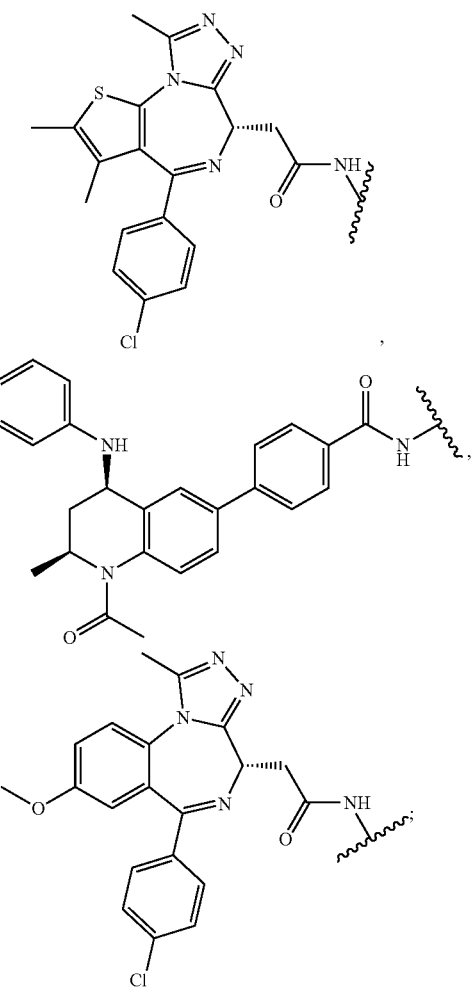

or a pharmaceutically acceptable salt, enantiomer, stereoisomer, hydrate, solvate, or polymorph of the compound.

3. The compound according to claim 2 having the structure A-L-B wherein A is an E3 ubiquitin ligase protein binding ligand compound of formula IA wherein R$_1$, R$_3$, R$_4$, and R$_5$, are as indicated in formula IA:
wherein L is directly bonded to the compound of formula IA at the R$_1$ position,
wherein R$_1$ is an optionally substituted cyclopropyl group with a covalent C-linked bond to L or R$_1$ is a covalent C-Linked bond to L,
wherein X is N,
wherein R$_{2a}$ is OH,
wherein R$_{2b}$, R$_x$, R$_3$ and R$_4$ are all H,
wherein R$_5$ is a —CH$_3$ group,
wherein Y is

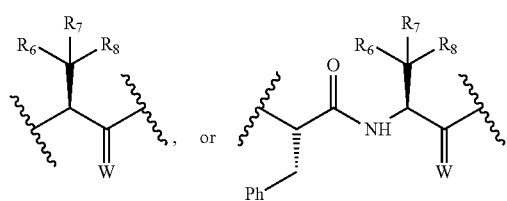

wherein W is O, and
   wherein B is independently selected from:

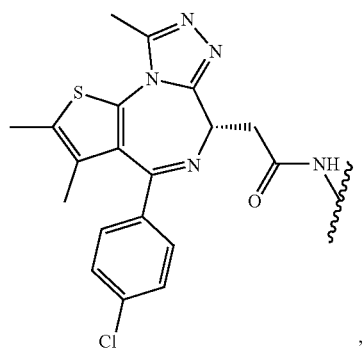

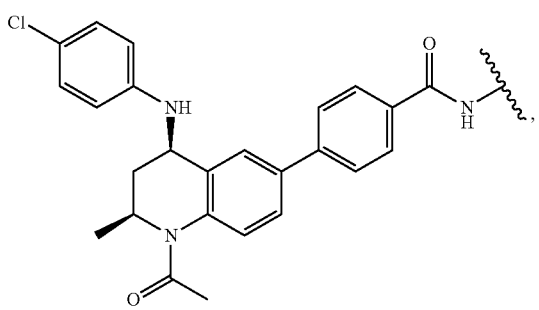

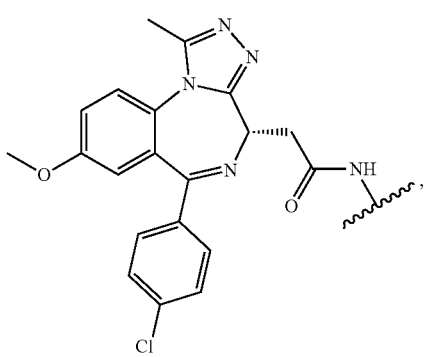

or a pharmaceutically acceptable salt, enantiomer, stereoisomer, hydrate, solvate, or polymorph thereof.

4. The compound according to claim 2 having the structure A-L-B wherein one of:
   (i) A is a compound of formula IA wherein L is directly bonded to the compound of formula IA at the $R_3$ position,
   wherein L is a —(CH$_2$CH$_2$O)$_b$— group wherein b is 1 to 10,
   wherein $R_{2a}$ is OH,
   wherein $R_{2b}$, $R_x$, and $R_4$ are all H,
   wherein $R_3$ is a covalent C-linked, a covalent O-linked, or a covalent —C(O)-linked bond to L, wherein $R_5$ is a —CH$_3$ group, wherein Y is

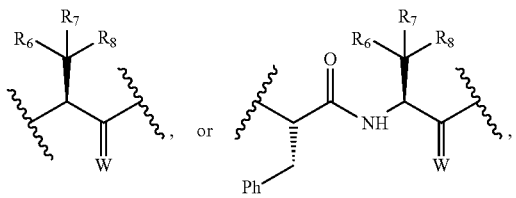

wherein W is O, and
or a pharmaceutically acceptable salt, enantiomer, stereoisomer, hydrate, solvate, or polymorph thereof; or
   (ii) A is a compound of formula IA wherein L is directly bonded to the compound of formula IA at the $R_4$ position,
   wherein L is a —(CH$_2$CH$_2$O)$_b$— group wherein b is 1 to 10,
   wherein $R_{2a}$ is OH,
   wherein $R_{2b}$, $R_x$, and $R_3$ are all H,
   wherein $R_4$ is a covalent C-linked, a covalent O-linked, or a covalent —C(O)-linked bond to L,
   wherein $R_5$ is a —CH$_3$ group,
   wherein Y is

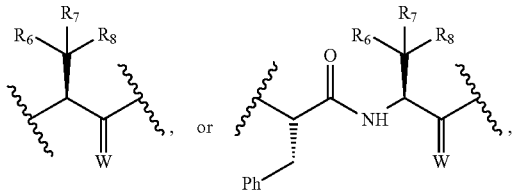

wherein W is O, and
   wherein B is independently selected from:

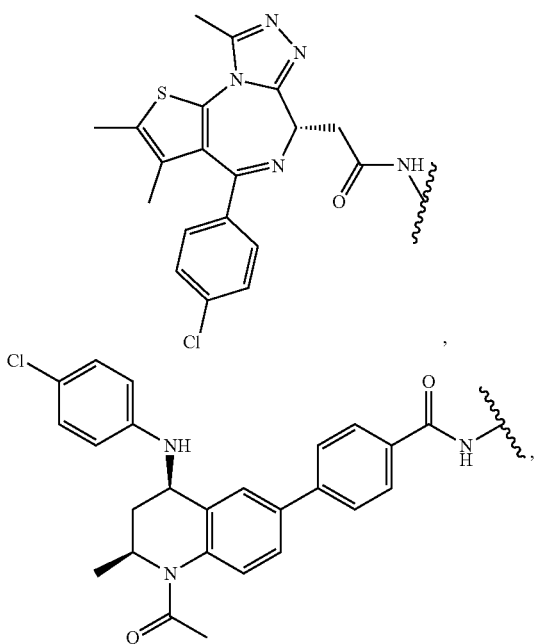

115
-continued

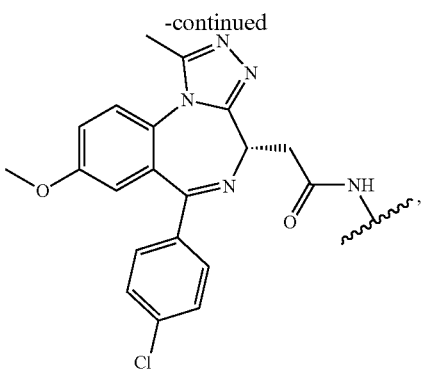

or a pharmaceutically acceptable salt, enantiomer, stereoisomer, hydrate, solvate, or polymorph thereof; or (iii) A is a compound of formula IA wherein L is directly bonded to the compound of IA at the $R_5$-position,
wherein $R_{2a}$ is OH,
wherein $R_{2b}$, $R_x$, $R_3$ and $R_4$ are all H,
wherein $R_5$ is a covalent C-linked bond to L,
wherein L is a —$(CH_2CH_2O)_b$— group wherein b is 1 to 10,
wherein Y is

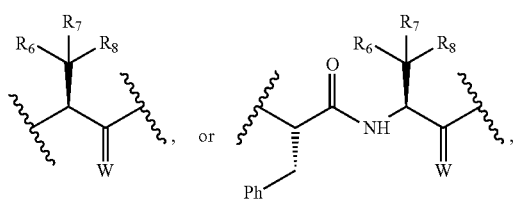

wherein W is O, and
wherein B is independently selected from:

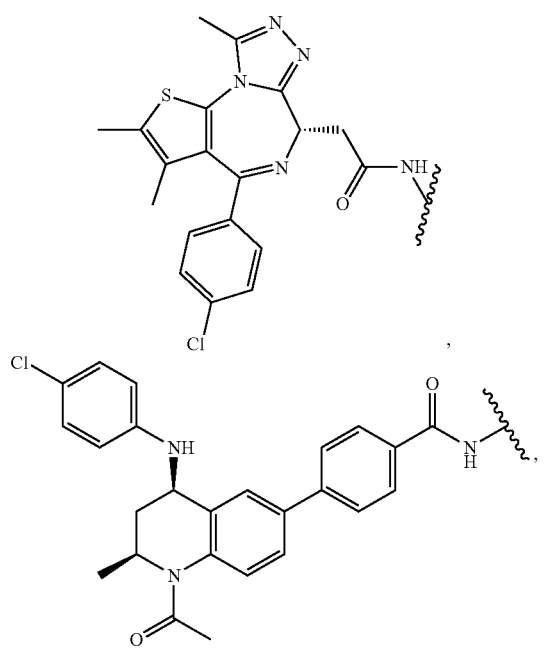

116
-continued

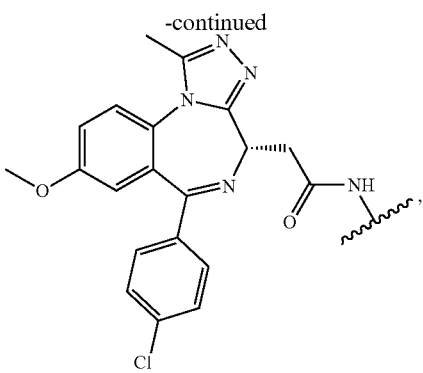

or a pharmaceutically acceptable salt, enantiomer, stereoisomer, hydrate, solvate, or polymorph thereof; or (iv) A is a compound of formula IA wherein L is directly bonded to the compound of formula IA at the $R_{8*}$ position,
wherein L is a —$(CH_2CH_2O)_b$— group wherein b is 1 to 10,
wherein $R_{2a}$ is OH,
wherein $R_{2b}$, $R_3$, and $R_4$ are all H,
wherein $R_5$ is a —$CH_3$ group,
wherein Y is

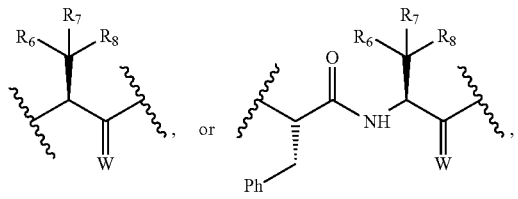

wherein W is O,
wherein $R_8$ is a —$(CH_2)_q R_{8*}$ group wherein q is 0, 1 or 2, and wherein $R_{8*}$ is a covalent C-, S-, or N-linked bond to L, and
wherein B is independently selected from:

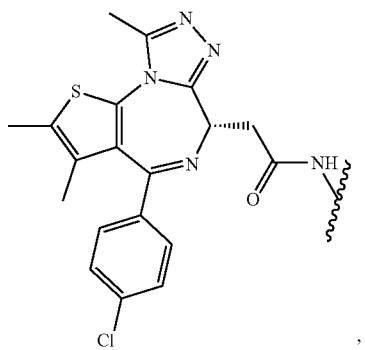

117

-continued

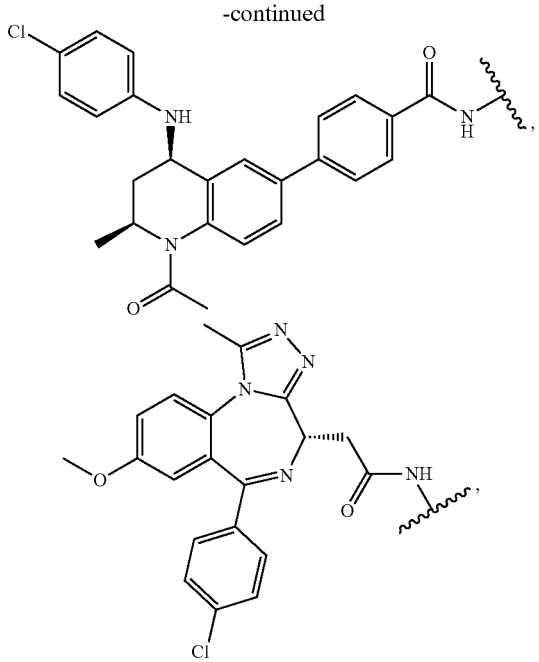

or a pharmaceutically acceptable salt, enantiomer, stereoisomer, hydrate, solvate, or polymorph thereof.

5. The compound according to claim 1 independently selected from:

(2R,3R,4S)-1-((S)-2-(tert-butyl)-17-((S)-4-(4-chlorophenyl)-2,3,9-trimethyl-6H-thieno[3,2- f][1,2,4]triazolo[4,3-a][1,4]diazepin-6-yl)-4,16-dioxo-6,9,12-trioxa-3,15-diazaheptadecanoyl)-3-fluoro-4-hydroxy-N-(4-(4-methylthiazol-5-yl)benzyl)pyrrolidine-2-carboxamide;

(2R,3S,4S)-1-((S)-2-(tert-butyl)-17-((S)-4-(4-chlorophenyl)-2,3,9-trimethyl-6H-thieno[3,2- f][1,2,4]triazolo[4,3-a][1,4]diazepin-6-yl)-4,16-dioxo-6,9,12-trioxa-3,15-diazaheptadecanoyl)-3-fluoro-4-hydroxy-N-(4-(4-methylthiazol-5-yl)benzyl)pyrrolidine-2-carboxamide;

(2R,3R,4S)-1-((S)-1-(4-((2S,4R)-1-acetyl-4-(4-chlorobenzyl)-2-methyl-1,2,3,4-tetrahydroquinolin-6-yl)phenyl)-12-(tert-butyl)-1, 10-dioxo-5,8-dioxa-2, 11-diazatridecan-13-oyl)-3-fluoro-4-hydroxy-N-(4-(4-methylthiazol-5-yl)benzyl)pyrrolidine-2-carboxamide;

(2R,3S,4S)-1-((S)-1-(4-((2S,4R)-1-acetyl-4-(4-chlorobenzyl)-2-methyl-1,2,3,4-tetrahydroquinolin-6-yl)phenyl)-12-(tert-butyl)-1, 10-dioxo-5,8-dioxa-2, 11-diazatridecan-13-oyl)-3-fluoro-4-hydroxy-N-(4-(4-methylthiazol-5-yl)benzyl)pyrrolidine-2-carboxamide;

(2R,3R,4S)-1(R)-3-(6-(2-((S)-4-(4-chlorophenyl)-2,3,9-trimethyl-6H-thieno[3,2-f][1,2,4]triazolo[4,3-a][1,4]diazepin-6-yl)acetamido)hexyl)thio)-2-(1-fluorocyclopropane-1-carboxamido)-3-m ethylbutanoyl)-3-fluoro-4-hydroxy-N-(4-(4-methylthiazol-5-yl)benzyl)pyrrolidine-2-carboxamide;

(2R,3R,4S)-1-((S)-2-acetamido-3,3-dimethylbutanoyl)-3-fluoro-4-hydroxy-N-(4-(4-methylthiazol-5-yl)benzyl)pyrrolidine-2-carboxamide;

(2R,3S,4S)-1-((S)-2-acetamido-3,3-dimethylbutanoyl)-3-fluoro-4-hydroxy-N-(4-(4-methylthiazol-5-yl)benzyl)pyrrolidine-2-carboxamide;

(2R,3R,4S)-3-fluoro-1(S)-2-(1-fluorocyclopropane-1-carboxamido)-3,3-dimethylbutanoyl)-4-hydroxy-N-(4-(4-methylthiazol-5-yl)benzyl)pyrrolidine-2-carboxamide;

(2R,3S,4S)-3-fluoro-1-((S)-2-(1-fluorocyclopropane-1-carboxamido)-3,3-dimethylbutanoyl)-4-hydroxy-N-(4-(4-methylthiazol-5-yl)benzyl)pyrrolidine-2-carboxamide;

(2R,3R,4 S)-1-((S)-2-(1-cyanocyclopropane-1-carboxamido)-3,3-dimethylbutanoyl)-3-fluoro-4-hydroxy-N-(4-(4-methylthiazol-5-yl)benzyl)pyrrolidine-2-carboxamide; and (2R,3S,4S)-1-((S)-2-(1-cyanocyclopropane-1-carboxamido)-3,3-dimethylbutanoyl)-3-fluoro-4-hydroxy-N-(4-(4-methylthiazol-5-yl)benzyl)pyrrolidine-2-carboxamide;

or a pharmaceutically acceptable salt, enantiomer, stereoisomer, hydrate, solvate, or polymorph thereof.

6. A pharmaceutical composition comprising an effective amount of a compound according to claim 1 in combination with a pharmaceutically acceptable carrier, additive or excipient.

7. A method for the prophylaxis or treatment of a disease or condition associated with deregulation of protein activity of one or more proteins within the Bromo- and Extra-terminal (BET) family of proteins BRD2, BRD3 and BRD4, the method comprising the administration of the compound of structure A-L-B of claim 1 to a subject suffering from or likely to be exposed to said disease or condition;
wherein:
the disease or condition is selected from a disease or condition associated with selective degradation of the BRD4 protein within the bromodomain of the BET family of proteins; or
the disease or condition is independently selected from: cancer; benign proliferative disorders; infection or non-infectious inflammatory events; autoimmune diseases; inflammatory diseases; systemic inflammatory response syndromes; viral infections and diseases; ophthalmological conditions.

8. A PROTAC compound having the structure A-L-B according to the compound of A-L-B underlaying the pharmaceutical composition according to claim 6, wherein said target protein is selected from one of:
the group consisting of structural proteins, receptors, enzymes, cell surface proteins, proteins pertinent to the integrated function of a cell, proteins involved in catalytic activity, aromatase activity, motor activity, helicase activity, metabolic processes, antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity, receptor activity, cell motility, membrane fusion, cell communication, regulation of biological processes, development, cell differentiation, response to stimulus, behavioral proteins, cell adhesion proteins, proteins involved in cell death, proteins involved in protein transporter activity, proteins involved in nuclear transport, proteins involved in ion transporter activity, proteins involved in channel transporter activity, proteins involved in carrier activity, proteins involved in permease activity, proteins involved in secretion activity, proteins involved in electron transporter activity, proteins involved in pathogenesis, proteins involved in chaperone regulator activity, proteins involved in nucleic acid binding activity, proteins involved in transcription regulator activity, proteins involved in extracellular organization and proteins involved in biogenesis activity and translation regulator activity; or the group consisting of B7.1 and B7, TI FRIm, TNFR2, NADPH oxidase, BcIIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCRI, CXCR2, nitric oxide synthase, cyclo-oxygenase 1, cyclo-oxygenase 2, 5HT receptors, dopamine receptors, G Proteins, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, Retinoid X Receptor, HIV 1 protease, HIV 1 integrase, influenza, neuraminidase, hepatitis B reverse transcriptase, sodium channel, multi drug resistance, protein P-glycoprotein and MRP, tyrosine kinases, CD23, CD 124, tyrosine kinase p56 Ick, CD4, CD5, IL-2 receptor, IL-1 receptor, TNF-alphaR, ICAM1, Cat+channels, VCAM, VLA-4 integrin, selectins, CD40/CD40L, newokinins and receptors, inosine monophosphate dehydrogenase, p38 MAP Kinase, RasIRafIMEWERK pathway, interleukin-1 converting enzyme, caspase, HCV, NS3 protease, HCV NS3 RNA helicase, glycinamide ribonucleotide formyl transferase, rhinovirus, 3C protease, herpes simplex virus- 1, protease, cytomegalovirus protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors P2Y1, P2Y2, P2Y4, P2Y6, and P2X1-7, farnesyltransferases, geranylgeranyl transferase, TrkA a receptor for NGF, beta-amyloid, tyrosine kinase FIk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, and chloride channels; acetyl-CoA carboxylase, adenylosuccinate synthetase, protoporphyrinogen oxidase, and enolpyruvylshikimate-phosphate synthase.

9. A PROTAC compound having the structure A-L-B according to claim 1 wherein one of:
B is an Hsp90 inhibitor; a kinase inhibitor, a phosphatase inhibitor, an MDM2 inhibitor, a compound which targets human BET Bromodomain-containing proteins, an HDAC inhibitor, a human lysine methyltransferase inhibitor, a compound targeting RAF receptor, a compound targeting FKBP, an angiogenesis inhibitor, an immunosuppressive compound, a compound targeting an aryl hydrocarbon receptor, a compound targeting an androgen receptor, a compound targeting an estrogen receptor, a compound targeting a thyroid hormone receptor, a compound targeting HIV protease, a compound targeting HIV integrase, a compound targeting HCV protease or a compound targeting acyl protein thioesterase 1 and/or 2.

10. A method of regulating protein activity of a target protein in a patient in need comprising administering to said patient an amount of a compound according to claim 1.

11. The compound of formula I, suitable for use in a PROTAC compound of structure A-L-B according to claim 1 wherein the compound of formula I, can be modified for covalent bonding to a B group as defined in claim 1, via a linker group L, or a pharmaceutically acceptable salt, stereoisomer, solvate or polymorph thereof.

12. A composition comprising a pharmaceutical intermediate compound of general formula II:

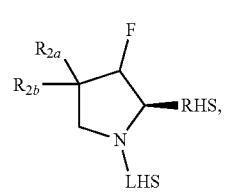

II wherein said compound comprises one of the following embodiments:

(i) $R_{2a}$ is OH, $R_{2b}$ is H, and wherein LHS is a 9-phenyl-9-fluorenyl group, a fluoroenylmethyloxycarbonyl group, a tert-butyloxycarbonyl protecting group (BOC group), or an acetamide group and wherein RHS is, —$CO_2CH_3$ or —$CO_2Bn$; or (ii) $R_{2a}$ is OH, $R_{2b}$ is H, LHS is a BOC group and RHS is a —$CO_2Bn$ group having the structural formulae II-A, II-B and/or II-C:

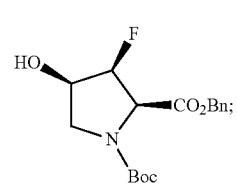

II-A

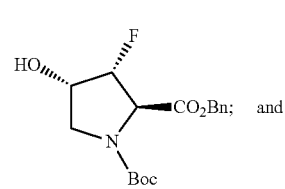

II-B and

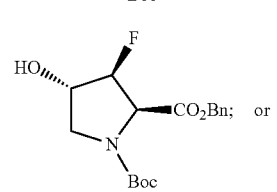

II-C or (iii) $R_{2a}$ is OH, $R_{2b}$ is H, LHS is a BOC group and RHS is a —$CO_2H$ group having the structural formulae II-E, II-F, II-G and/or II-H:

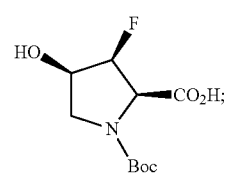

II-E

-continued

II-F
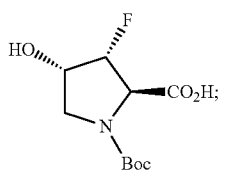

II-G
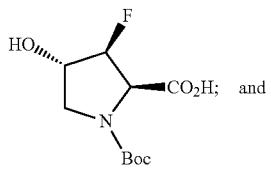
and

II-H
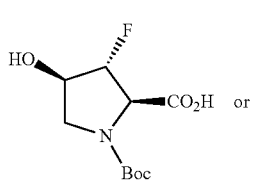
or (iv) $R_{2a}$ is OH, $R_{2b}$ is H, wherein LHS is an acetamide group and RHS is a —CO$_2$Me group having the structural formulae II-I, II-J, II-K and/or II-L:

II-I
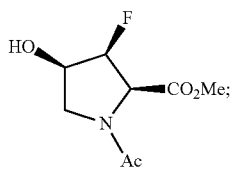

II-J
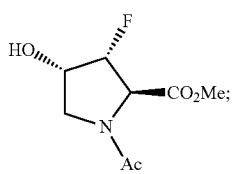

II-J
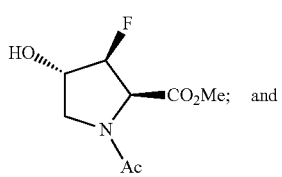
and

II-L
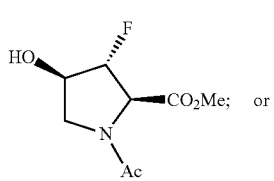
or (v) $R_{2a}$ is OH, $R_{2b}$ is H, LHS is a 9-phenyl-9-fluorenyl group and RHS is —CO$_2$H, —CO$_2$CH$_3$ or —CO$_2$D, where D is an alternative alkyl ester or a benzyl ester, having the structural formulae II-M, II-N, II-P and/or II-O:

II-M
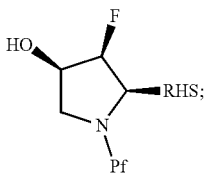

II-N

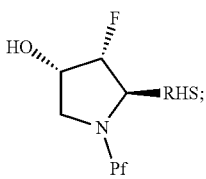

II-O

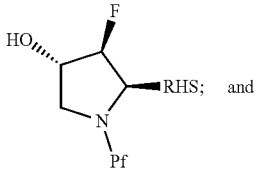
and

II-P

HO
F
RHS.
N
Pf

13. A process for the preparation of compounds of general formula II:

II $R_{2a}$, $R_{2b}$, F, RHS, LHS structure wherein $R_{2a}$ is OH, —CHF$_2$, —CF$_3$, or NH$_2$, wherein $R_{2b}$ is H, $^2$H, $^3$H, a —(C$_1$-C$_3$) alkyl group, an aryl group, a heteroaryl group, —CF$_3$, —CF$_2$H, or a —CF$_2$—(C$_1$-C$_2$) alkyl group, wherein LHS is: H; an amine protecting group selected from: a 9-phenyl-9-fluorenyl, a fluoroenylmethyloxycarbonyl protecting group (Fmoc), a tert-butyloxycarbonyl protecting group (BOC group), or an acetamide group; or a suitable alternative amine protecting group for the ring-N, wherein RHS is —C(O)OH, —C(O)OCH$_3$ or —C(O)OD where D is an alternative alkyl ester or a benzyl ester, wherein the compound of formula II is not

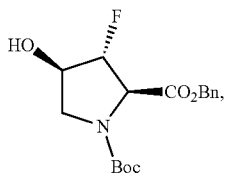
II-D from intermediate compounds of general formula III, wherein the LHS is H; an amine protecting group selected from: a 9-phenyl-9-fluorenyl group, a fluoroenylmethyloxycarbonyl group, a BOC group, or an acetamide group; or a suitable alternative amine protecting group for the ring-N:

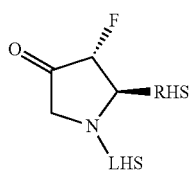
III and wherein said compounds of general formula III are converted to compounds of general formula II via treatment with a suitable reducing agent.

14. A process for the preparation of intermediate compounds of structural formulae II-A II-B, and II-C as defined in claim 12 from intermediate compounds of structural formulae III-A or III-B:

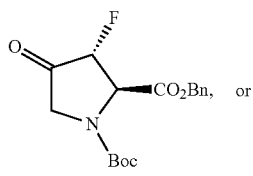
III-A

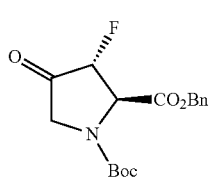
III-B wherein said intermediate compounds of structural formulae III-A or III-B are converted into structural formulae II-A, II-B, and II-C by treatment with a suitable reducing agent.

15. A process for the preparation of intermediate compounds of general formula III, via conversion of starting compounds of formula V to intermediate compounds of general formula IV with subsequent transformation into compounds of general formula III:

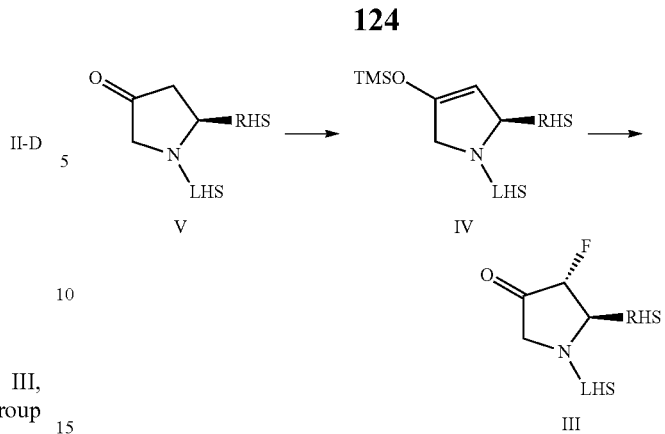

wherein said compounds of general formula V are converted to compounds of general formula IV via a 2-step approach with protection using a TMSO- group followed by fluorination of the protected intermediate compound IV to provide the desired 3-fluoro-compounds, wherein RHS is: —C(O)OH, —C(O)OCH$_3$ or —C(O)OD where D is an alternative alkyl ester or a benzyl ester, and wherein LHS is: H; an amine protecting group selected from: a 9-phenyl-9-fluorenyl, a fluoroenylmethyloxycarbonyl protecting group (Fmoc), a tert-butyloxycarbonyl protecting group (BOC group), or an acetamide group; or a suitable alternative amine protecting group for the ring-N.

16. A process for the preparation of intermediate compounds of structural formula III-A and III-B, via conversion of compound of structural formula V to an intermediate compound of structural formula IV with subsequent transformation into compounds of formulae III-A and III-B:

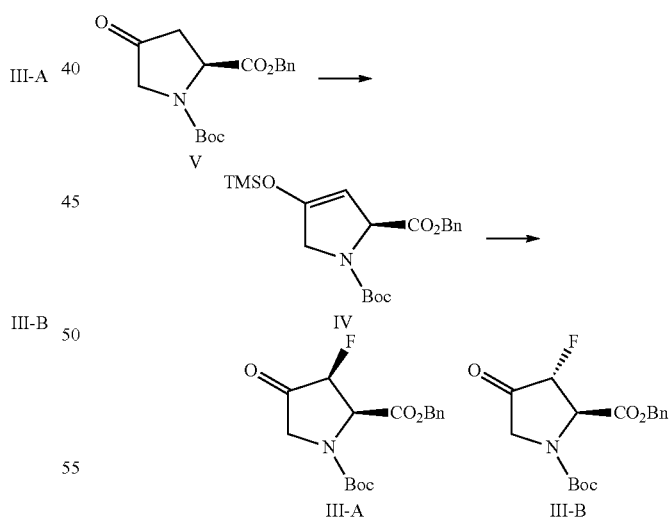

wherein compound formula V is converted to compounds III-A and III-B via a 2-step approach, with protection using a TMSO- group followed by fluorination of the protected intermediate compound IV to provide the desired 3-fluoro-compounds of formulae III-A and III-B.

17. The compound of claim 1, of structure A-L-B wherein A is a compound of formula I, wherein $R_{2a}$ is OH, $R_{2b}$ is H, and $R_x$ is H and wherein L is a group which is directly bonded to the compound of formula I and wherein L is —$(CH_2)_nL^1(CH_2O)_p$—, wherein $L^1$ is a covalent bond, a 5 or 6 membered heterocyclic or heteroaromatic ring containing 1, 2 or 3 nitrogen atoms, phenyl, —$(C_2$-$C_4)$alkyne, —$SO_2$—, or —NH—.

18. The compounds of general formula II according to claim 12 wherein LHS is a 9-phenyl-9-fluorenyl group and RHS is —$C(O)OCH_3$ having the structural formulae II-Q, II-R, II-S and II-T:

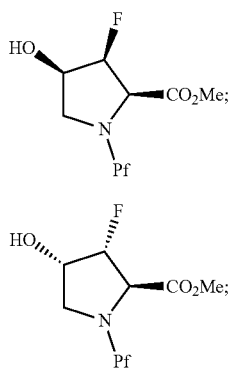

II-Q

II-R

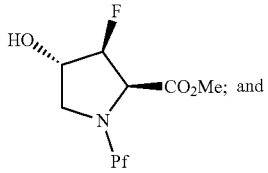

II-S

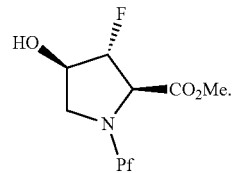

II-T

19. The pharmaceutical composition of claim 6, further comprising an additional bioactive agent independently selected from one or more agents for the treatment of: cancer; benign proliferative disorders; infection or non-infectious inflammatory events; autoimmune diseases; inflammatory diseases; systemic inflammatory response syndromes; viral infections and diseases; and ophthalmological conditions.

* * * * *